US010077302B2

(12) United States Patent
Grabulovski et al.

(10) Patent No.: US 10,077,302 B2
(45) Date of Patent: Sep. 18, 2018

(54) METHOD OF INHIBITING HUMAN IL-1 BETA BY ADMINISTERING AN ANTIBODY TO HUMAN IL-1 BETA

(71) Applicant: Cell Medica Switzerland AG, Schlieren (CH)

(72) Inventors: Stefanie Grabulovski, Zürich (CH); Titus Kretzschmar, Steinhausen (CH); Simone Schmitt, Schlieren (CH); Abdijapar Shamshiev, Zürich (CH); Thorsten Alexander Schafer, Lörrach (DE)

(73) Assignee: Cell Medica Switzerland AG, Schlieren (CH)

( * ) Notice: Subject to any disclaimer, the term of this patent is extended or adjusted under 35 U.S.C. 154(b) by 0 days.

(21) Appl. No.: 15/202,982

(22) Filed: Jul. 6, 2016

(65) Prior Publication Data

US 2017/0051054 A1 Feb. 23, 2017

Related U.S. Application Data

(62) Division of application No. 14/072,165, filed on Nov. 5, 2013, now Pat. No. 9,404,930.

(60) Provisional application No. 61/722,532, filed on Nov. 5, 2012.

(30) Foreign Application Priority Data

Nov. 5, 2012 (EP) ..................................... 12007503

(51) Int. Cl.
*A61K 39/395* (2006.01)
*C07K 16/24* (2006.01)
*G01N 33/68* (2006.01)
*A61K 39/00* (2006.01)

(52) U.S. Cl.
CPC ........ *C07K 16/245* (2013.01); *A61K 39/3955* (2013.01); *G01N 33/6869* (2013.01); *A61K 2039/505* (2013.01); *C07K 2317/24* (2013.01); *C07K 2317/35* (2013.01); *C07K 2317/565* (2013.01); *C07K 2317/622* (2013.01); *C07K 2317/76* (2013.01); *C07K 2317/94* (2013.01); *G01N 2333/545* (2013.01)

(58) Field of Classification Search
CPC ................................................ A61K 39/3955
See application file for complete search history.

(56) References Cited

U.S. PATENT DOCUMENTS

2003/0026806 A1 2/2003 Witte et al.
2007/0065439 A1 3/2007 Green et al.

FOREIGN PATENT DOCUMENTS

| JP | 2008-543340 A | 12/2008 |
|---|---|---|
| RU | 2286351 C2 | 10/2006 |
| WO | 0216436 A2 | 2/2002 |
| WO | 03097697 A2 | 11/2003 |
| WO | 2004067568 A2 | 8/2004 |
| WO | 2006081139 A2 | 8/2006 |
| WO | 2006131013 A2 | 12/2006 |
| WO | 2007002261 A2 | 1/2007 |
| WO | WO 2007/002261 A2 | 1/2007 |
| WO | 2009149370 A1 | 12/2009 |
| WO | 2009156725 A1 | 12/2009 |
| WO | 2009156726 A2 | 12/2009 |
| WO | WO 2009/149370 A1 | 12/2009 |
| WO | 2010028273 A1 | 3/2010 |
| WO | 2012034039 A2 | 3/2012 |

OTHER PUBLICATIONS

Office Action corresponding to Japanese Application No. 2015-54015 dated Sep. 8, 2017.
Office Action corresponding to Chinese Application No. 201380064089.1 dated Sep. 19, 2017.
Office Action corresponding to Chinese Application No. 201380064089.1 dated May 17, 2016.
Brown et al. "Tolerance to Single, but Not Multiple, Amino Acid Replacements in Antibody $V_H$ CDR2", *The Journal of Immunology* 156:3285-3291 (1996).
Office Action corresponding to European Application No. 13786473.2 dated Jun. 21, 2016.
Amit et al, "Three-Dimensional Structure of an Antigen-Antibody Complex at 2.8 A Resolution", *Science* 233(4765):747-753 (1986).
Eshhar Z. "The T-Body Approach: Redirecting T Cells with Antibody Specificity", *Handbook of Exp. Pharmacol*, 181:329-42 (2008).
Lederman et al, "A Single Amino Acid Substitution in a Common African Allele of the CD4 Molecule Ablates Binding of the Monoclonal Antibody, OKT4", *Molecular Immunology* 28(11):1171-1181 (1991).
Li et al, "Temporal associations between interleukin 22 and the extracellular domains of IL-22R and IL-10R2", *International Immunopharmacology* 4:683-708 (2004).
Panka et al. "Variable region framework differences result in decreased or increased affinity of variant anti-digoxin antibodies" *Proc. Natl. Acad. Sci. USA* 85:3080-3084 (1988).

(Continued)

*Primary Examiner* — Prema Mertz

(74) *Attorney, Agent, or Firm* — Myers Bigel, P.A.

(57) ABSTRACT

The present invention relates to anti-IL-1 beta binding members and in particular to monovalent high potency IL-1 beta-binding antibody fragments being highly stable and soluble. Such binding members may be used in the treatment of inflammatory and other diseases as well as in diagnostics. Also provided are related nucleic acids, vectors, cells, and compositions.

24 Claims, 5 Drawing Sheets

Specification includes a Sequence Listing.

(56) References Cited

OTHER PUBLICATIONS

Rudikoff et al. "Single amino acid substitution altering antigen-binding specificity", *Proc. Natl. Aced. Sci. USA* 79:1979-1983 (1992).
Office Action corresponding to Russian Application No. 2015120450/10 dated Oct. 17, 2017.
Alten, R., et. al., "The human, anti-IL-1β monoclonal antibody ACZ885 is effective in joint inflammation models in mice and in a proof-of-concept study in patients with rheumatoid arthritis", Arthrins Research and Therapy, Biomed Central, London, GB, vol. 10, No. 3, Jun. 5, 2008.
Owyang, A. M. et al., "XOMA 052, a potent, high-affinity monoclonal antibody for the treatment of IL-1 beta-mediated dise,ases", MABS, vol. 3, No. 1, Jan. 2011 (Jan. 2011), pp. 49-60.
Bhaskar, V., et al., Monoclonal antibodies targeting IL-1 beta reduce biomarkers of atherosclerosis in vitro and inhibit atheroscierotic plaque formation in Apolipoprotein E-deficient mice', Atherosclerosis, Elsevier Ireland Ltd, IE, vol. 216, No. 2, Feb. 16, 2011 (Feb. 16, 2011), pp. 313-320.
Owyang, A. M., et al., "XOMA 052, an Anti-IL-1 beta Monoclonal Antibody, Improves Glucose Control and beta-Cell Function in the Diet-induced Obesity Mouse Modsi", Endocrinology, Endocrine' Society, US, vol. 151, No. 6, Jun. 1, 2010 (Jun. 1, 2010), pp. 2515-2527.
Jackson, J. R., et al., "In Vitro Antibody Maturation Improvement of a High Affinity, Neutralizing Antibody Against IL-1Beta", The Journal of Immunology, The American Association of Immunologists, US, vol. 154, No. 7, Apr. 1, 1995 (Apr. 1, 1995), pp. 3310-3319.
Holliger, P., et al., "Engineered antibody fragments and the rise of single domains", Nature Biotechnology vol. 23, No. 9, 2005, pp. 1126-1136.
Pasut, G., "State of the art in PEGylation; the great versatility achieved after forty years of research", Journal or Controlled Release, vol. 161, No. 2, 2012, pp. 461-472.
Hossler, P., "Optimal and consistent protein glycosylation in mammalian cell culture", Glycobiology, vol. 19, No. 9, 2009, pp. 936-949.
Gilbreth, R. N., et al., "Structural insights for engineering binding proteins based on nonantibody scaffolds", Current Opinion in Structural Biology, vol. 22, 2012, pp. 413-420.
Gundluru, M. K., et al., "Design, synthesis arid initial bioiogical evaluation of a novel pladlenolide analog scaffold", Medchemcomm., vol. 2(9), 2011, pp. 904-908.
Paterson, I., et al., "Total synthesis and biological evaluation of a series of macrocyclic hybrids and analogues of the antimitotic natural products dictyostatin, discodermolide and taxol", Chem Asian J., vol. 6(2), 2011, pp. 459-1473.
Morita, H., et al., "Synthesis of unnatural alkaloid scaffolds by exploiting plant polyketide synthase", PNAS, vol. 108 (33), 2011, pp. 13504-13509.
Hoshino, Y., et al., "Recognition, neutralization and clearance of target peptides in the blood stream of living mice by molecular imprinted polymer nanoparticles: a plastic antibody", Journal of the American Chemical Society, vol. 132(19), 2010, pp. 8684-6645.
Strehlitz, B., et al "Aptamers for pharmaceuticals and their application in environmental analytics", Bioanalytical Reviews, vol. 4, 2012, pp. 1-30.
Ye, M., et al., "Generating Aptamers by Cell-SELEX for Applications in Molecular Medicine", International Journal of Molecular Sciences, vol. 13, 2012, pp. 3341-3353.
Maasch, C., et al., "Polyethylenimine-Polyplexes of Spiegeimer NOX-A50 directed against intracellular high mobility group protein A1 (HMGA1) reduce tumor growth in vivo:", JBC, vol. 285(51), 2010, pp. 40012-40018.
Gould, A., et al., "Cyclotides, a novel ultrastable polypeptide scaffold for drug discovery", Curr Pharm Des., vol. 17(38), 2011, pp. 4294-4307.
Cheng, Y., et al., "Relationship between the inibition constant (KI) and the concentration of inhibitor which causes 50 per cent inhibition (I50) of an enzymatic reaction", Biochemical Pharmacology, vol. 22, 1975, pp. 3009-3108.
Rammes, G., et al., "Identification of a domain which affects kinetics and antagonistic potency of clozapine at 5-HT3 receptors", PLOS ONE, vol. 4, 2009, pp. 1-14.
Zhen, J., et al., "Concentration of receptor and ligand revisited in a modified receptor binding protocol for high-affinity radiollgands: [3H] spiperone binding to D2 and D3 dopamine receptors", Journal of Neuroscience Methods, vol. 188, 2010, pp. 32-38.
Dinarello, C. A. "Treating inflammation by blocking interleukin-1 in a broad spectrum of disease", Nature Reviews, vol. 11, 2012, pp. 633-652.
Nicholls, P. J., et al., "Characterization of single-chain antibody (sFv)-toxin fusion proteins produced in vitro in rabbit reticulocyte lysate", Journal of Biological Chemistry, vol. 268(7), 1993, pp. 5302-5308.
Holliger, P., et al., "Diabodies: small bivalent and bispecific antibody fragments", PNAS, vol. 90, No. 14, 1993, pp. 6444-6448.
Honegger, A. et al., "Yet another numbering scheme for immunoglobulln variable domains: An automatic modelling and analysis too", Journal of Molecular Biology, vol. 309, 2001, pp. 657-670.
Needleman, S. B., et al., "A general method applicabie to the search for similarities in the amino acid sequence of two proteins", Journal of Molecular Biology, vol. 48, 1970, pp. 443-453.
Borras, L., et al., "Generic approach for the generation of stable humanized single-Chain Fv fragments from rabbit monoclonal antibodies", Journal of Biological Chemistry, vol. 285, No. 12, 2010, pp. 9054-906.
Alfthan, K., et al., "Properties of a single-chain antibody containing different linker peptides", Protein Engineering, vol. 8, No. 7, 1995, pp. 725-731.
Niesen, F. H. et al., "The use of differential scanning fluorimetry to detect ligand interactions that promote protein stability", Nature Protocols, vol. 2(9), 2007, pp. 2212-2221.
Hou, J., et al., "Design of a superior cytokine antagonist for to loal ophthalmic use," PNAS, 110(10): 3913-3918 (2013).
Ruperto, N., et el., "Two Randomized Trials of Canakinumab in Systemic Juvenile Idiopathic Arthritis," N. Engl. J. Med., 367(25): 2396-2406 (2012).
Kahn, P. J., at al, "Higher-dose Anakinra Is Effective in a Case of Medically Refractory Macrophage Activation Syndrome," The Journal of Rheumatology, 40(5): 743-744 (2013).
Launay, D., et al., "Effect of in Vitro and in Vivo Anakinra on Cytokinas Production in Schnitzler Syndrome," PLOS ONE, 8(3): e59327 (2013).
Soriano, A., et al., "IL-1β biological treatment of familial Mediterranean fever," Clin Rev Allergy Immunol., 45(1):117-30 (2013).
Vanderschueren, S., et al., "Canakinumab in Schnitzler syndrome," Semin Arthritis Rheum., 42(4):413-8 (2013).
Vitale, A., et al., "Biological Treatments: New Weapons in the Management of Monogenic Autoinflammatory Disorders," Mediators of inflammation, vol. 2013, Hindawi Publishing Corporation (2013).
Contassot, E., et al., "Interleukin-1, inflammasomes, autoinflammation and the skin," Swiss Med Wkly., 142: w13590 pp. 1-10 (2012).
Dinarello, C. A., "How interleukin-1β Induces Gouty Arthritis," Arthritis Rheum., 62(11): 3140-3144 (2010).
Dinarello, C. A,. "Blocking Interleukin-1β in Acute and Chronic Autoinflammatory Diseases," J Intern Med., 269(1): 16-28 (2011).
Chinese Office Action corresponding to Chinese Application No. 201380064089.1 dated Jun. 27, 2018.

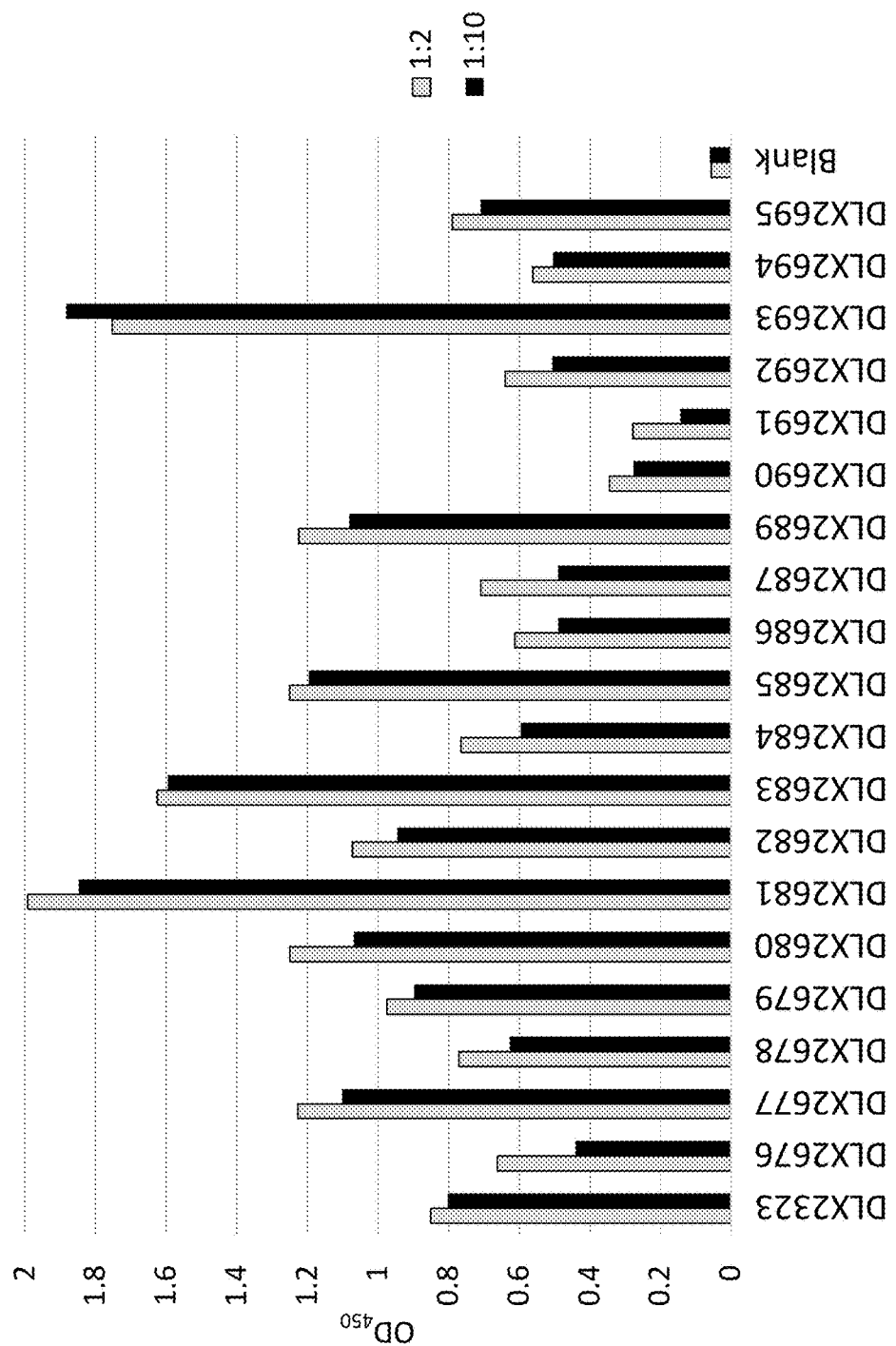

SEQUENCE LISTING

<160> NUMBER OF SEQ ID NOS: 163

<210> SEQ ID NO 1
<211> LENGTH: 9
<212> TYPE: PRT
<213> ORGANISM: Oryctolagus cuniculus -continued

```
<400> SEQUENCE: 1

Phe Ser Leu Ser Ser Ala Ala Met Ala
1               5

<210> SEQ ID NO 2
<211> LENGTH: 16
<212> TYPE: PRT
<213> ORGANISM: Oryctolagus cuniculus

<400> SEQUENCE: 2

Ile Ile Tyr Asp Ser Ala Ser Thr Tyr Tyr Ala Ser Trp Ala Lys Gly
1               5                   10                  15

<210> SEQ ID NO 3
<211> LENGTH: 11
<212> TYPE: PRT
<213> ORGANISM: Oryctolagus cuniculus

<400> SEQUENCE: 3

Glu Arg Ala Ile Phe Ser Gly Asp Phe Val Leu
1               5                   10

<210> SEQ ID NO 4
<211> LENGTH: 11
<212> TYPE: PRT
<213> ORGANISM: Oryctolagus cuniculus

<400> SEQUENCE: 4

Gln Ala Ser Gln Ser Ile Asp Asn Trp Leu Ser
1               5                   10

<210> SEQ ID NO 5
<211> LENGTH: 7
<212> TYPE: PRT
<213> ORGANISM: Oryctolagus cuniculus

<400> SEQUENCE: 5

Arg Ala Ser Thr Leu Ala Ser
1               5

<210> SEQ ID NO 6
<211> LENGTH: 10
<212> TYPE: PRT
<213> ORGANISM: Oryctolagus cuniculus

<400> SEQUENCE: 6

Gln Asn Thr Gly Gly Gly Val Ser Ile Ala
1               5                   10

<210> SEQ ID NO 7
<211> LENGTH: 119
<212> TYPE: PRT
<213> ORGANISM: Artificial Sequence
<220> FEATURE:
<223> OTHER INFORMATION: humanized VH sequence

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
                20                  25                  30

Ala Met Ala Trp Val Arg Gln Ala Pro Gly Lys Gly Leu Glu Trp Val
            35                  40                  45
```

Gly Ile Ile Tyr Asp Ser Ala Ser Thr Tyr Tyr Ala Ser Trp Ala Lys
            50                  55                  60

Gly Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Arg Ala Ile Phe Ser Gly Asp Phe Val Leu Trp Gly Gln Gly
                100                 105                 110

Thr Leu Val Thr Val Ser Ser
            115

<210> SEQ ID NO 8
<211> LENGTH: 109
<212> TYPE: PRT
<213> ORGANISM: Artificial Sequence
<220> FEATURE:
<223> OTHER INFORMATION: humanized VL sequence

<400> SEQUENCE: 8

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Val Ser
                 85                  90                  95

Ile Ala Phe Gly Gln Gly Thr Lys Leu Thr Val Leu Gly
                100                 105

<210> SEQ ID NO 9
<211> LENGTH: 20
<212> TYPE: PRT
<213> ORGANISM: Artificial Sequence
<220> FEATURE:
<223> OTHER INFORMATION: linker sequence

<400> SEQUENCE: 9

Gly Gly Gly Gly Ser Gly Gly Gly Ser Gly Gly Gly Ser Gly
 1               5                  10                  15

Gly Gly Gly Ser
            20

<210> SEQ ID NO 10
<211> LENGTH: 248
<212> TYPE: PRT
<213> ORGANISM: Artificial Sequence
<220> FEATURE:
<223> OTHER INFORMATION: humanized IL-1 beta scFv

<400> SEQUENCE: 10

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile

```
                35                  40                  45
Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                 85                  90                  95

Ile Ala Phe Gly Gln Gly Thr Lys Leu Thr Val Leu Gly Gly Gly Gly
            100                 105                 110

Gly Ser Gly Gly Gly Ser Gly Gly Gly Ser Gly Gly Gly Gly
        115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
            195                 200                 205

Leu Gln Met Asn Ser Leu Arg Ala Glu Asp Thr Ala Val Tyr Tyr Cys
210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 11
<211> LENGTH: 9
<212> TYPE: PRT
<213> ORGANISM: Artificial Sequence
<220> FEATURE:
<223> OTHER INFORMATION: variant of CDR-H1
<220> FEATURE:
<221> NAME/KEY: misc_feature
<222> LOCATION: (5)..(6)
<223> OTHER INFORMATION: Xaa can be any naturally occurring amino acid

<400> SEQUENCE: 11

Phe Ser Leu Ser Xaa Xaa Ala Met Ala
1               5

<210> SEQ ID NO 12
<211> LENGTH: 16
<212> TYPE: PRT
<213> ORGANISM: Artificial Sequence
<220> FEATURE:
<223> OTHER INFORMATION: Variant of CDR-H2
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12

Ile Ile Xaa Xaa Ser Ala Ser Thr Xaa Tyr Ala Ser Trp Ala Lys Gly
1               5                   10                  15
```

```
<210> SEQ ID NO 13
<211> LENGTH: 11
<212> TYPE: PRT
<213> ORGANISM: Artificial Sequence
<220> FEATURE:
<223> OTHER INFORMATION: variant of CDR-H3
<220> FEATURE:
<221> NAME/KEY: misc_feature
<222> LOCATION: (2)..(11)
<223> OTHER INFORMATION: Xaa can be any naturally occurring amino acid

<400> SEQUENCE: 13

Glu Xaa Xaa Xaa Xaa Xaa Xaa Xaa Xaa Xaa
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Variant of CDR-L1
<220> FEATURE:
<221> NAME/KEY: misc_feature
<222> LOCATION: (7)..(9)
<223> OTHER INFORMATION: Xaa can be any naturally occurring amino acid

<400> SEQUENCE: 14

Gln Ala Ser Gln Ser Ile Xaa Xaa Xaa Leu Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Variant of CDR-L2
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Xaa Ala Ser Xaa Leu Ala Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Variant of CDR-L3
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 16

Gln Asn Xaa Gly Xaa Xaa Xaa Xaa Ile Ala
1               5                   10

<210> SEQ ID NO 17
<211> LENGTH: 744
```

-continued

```
<212> TYPE: DNA
<213> ORGANISM: Artificial Sequence
<220> FEATURE:
<223> OTHER INFORMATION: DNA sequence of DLX2323

<400> SEQUENCE: 17
gaaattgtta tgacccagag cccgagcacc ctgagcgcaa gcgttggtga tcgtgtgatt    60
attacctgtc aggcaagcca gagcattgat aattggctga gctggtatca gcagaaaccg   120
ggtaaagcac cgaaactgct gatttatcgt gcaagcaccc tggcaagcgg tgttccgagc   180
cgttttagcg gtagcggtag tggtgcagaa tttacccctga ccattagcag cctgcagccg   240
gatgattttg caacctatta ttgtcagaat accggtggtg gtgttagcat tgcatttggt   300
cagggcacca aactgaccgt tctgggtggt ggcggtggat ccggtggggg tggtagcgga   360
ggtggtggtt caggcggtgg tggcagcgaa gttcagctgg ttgaaagtgg tggtggtctg   420
gttcagcctg gtggtagcct gcgtctgagc tgtaccgcaa gcggttttag cctgagcagc   480
gcagcaatgg catgggttcg tcaggcacct ggtaaaggtc tggaatgggt tggtattatc   540
tatgatagcg caagcaccta ttatgcaagc tgggcaaaag gtcgtttttac cattagccgt   600 gataccagta aaataccgt ttacctgcag atgaatagtc tgcgtgcaga ggataccgca   660
gtgtattatt gtgcacgtga acgtgcaatt ttcagcggtg attttgttct gtggggtcag   720
ggaaccctgg ttaccgttag cagc                                          744

<210> SEQ ID NO 18
<211> LENGTH: 23
<212> TYPE: PRT
<213> ORGANISM: Artificial Sequence
<220> FEATURE:
<223> OTHER INFORMATION: framework sequence L1

<400> SEQUENCE: 18

Glu Ile Val Met Thr Gln Ser Pro Ser Thr Leu Ser Ala Ser Val Gly
1               5                   10                  15

Asp Arg Val Ile Ile Thr Cys
            20

<210> SEQ ID NO 19
<211> LENGTH: 15
<212> TYPE: PRT
<213> ORGANISM: Artificial Sequence
<220> FEATURE:
<223> OTHER INFORMATION: framework sequence L2

<400> SEQUENCE: 19

Trp Tyr Gln Gln Lys Pro Gly Lys Ala Pro Lys Leu Leu Ile Tyr
1               5                   10                  15

<210> SEQ ID NO 20
<211> LENGTH: 32
<212> TYPE: PRT
<213> ORGANISM: Artificial Sequence
<220> FEATURE:
<223> OTHER INFORMATION: framework sequence L3

<400> SEQUENCE: 20

Gly Val Pro Ser Arg Phe Ser Gly Ser Gly Ser Gly Ala Glu Phe Thr
1               5                   10                  15

Leu Thr Ile Ser Ser Leu Gln Pro Asp Asp Phe Ala Thr Tyr Tyr Cys
            20                  25                  30
```

```
<210> SEQ ID NO 21
<211> LENGTH: 11
<212> TYPE: PRT
<213> ORGANISM: Artificial Sequence
<220> FEATURE:
<223> OTHER INFORMATION: framework sequence L4

<400> SEQUENCE: 21

Phe Gly Gln Gly Thr Lys Leu Thr Val Leu Gly
1               5                   10

<210> SEQ ID NO 22
<211> LENGTH: 26
<212> TYPE: PRT
<213> ORGANISM: Artificial Sequence
<220> FEATURE:
<223> OTHER INFORMATION: framework sequence H1

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Thr Ala Ser Gly
            20                  25

<210> SEQ ID NO 23
<211> LENGTH: 14
<212> TYPE: PRT
<213> ORGANISM: Artificial Sequence
<220> FEATURE:
<223> OTHER INFORMATION: framework sequence H2

<400> SEQUENCE: 23

Trp Val Arg Gln Ala Pro Gly Lys Gly Leu Glu Trp Val Gly
1               5                   10

<210> SEQ ID NO 24
<211> LENGTH: 32
<212> TYPE: PRT
<213> ORGANISM: Artificial Sequence
<220> FEATURE:
<223> OTHER INFORMATION: framework sequence H3

<400> SEQUENCE: 24

Arg Phe Thr Ile Ser Arg Asp Thr Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 25
<211> LENGTH: 11
<212> TYPE: PRT
<213> ORGANISM: Artificial Sequence
<220> FEATURE:
<223> OTHER INFORMATION: framework sequence H4

<400> SEQUENCE: 25

Trp Gly Gln Gly Thr Leu Val Thr Val Ser Ser
1               5                   10

<210> SEQ ID NO 26
<211> LENGTH: 26
<212> TYPE: PRT
<213> ORGANISM: Artificial Sequence
<220> FEATURE:
<223> OTHER INFORMATION: framework sequence H1

<400> SEQUENCE: 26
```

Glu Val Gln Leu Val Glu Ser Gly Gly Gly Leu Val Gln Pro Gly Gly
1               5                   10                  15

Ser Leu Arg Leu Ser Cys Thr Val Ser Gly
            20                  25

<210> SEQ ID NO 27
<211> LENGTH: 14
<212> TYPE: PRT
<213> ORGANISM: Artificial Sequence
<220> FEATURE:
<223> OTHER INFORMATION: framework sequence H2

<400> SEQUENCE: 27

Trp Val Arg Gln Ala Pro Gly Lys Gly Leu Glu Trp Val Gly
1               5                   10

<210> SEQ ID NO 28
<211> LENGTH: 32
<212> TYPE: PRT
<213> ORGANISM: Artificial Sequence
<220> FEATURE:
<223> OTHER INFORMATION: framework sequence H3

<400> SEQUENCE: 28

Arg Phe Thr Ile Ser Lys Asp Thr Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 29
<211> LENGTH: 11
<212> TYPE: PRT
<213> ORGANISM: Artificial Sequence
<220> FEATURE:
<223> OTHER INFORMATION: framework sequence H4

<400> SEQUENCE: 29

Trp Gly Gln Gly Thr Leu Val Thr Val Ser Ser
1               5                   10

<210> SEQ ID NO 30
<211> LENGTH: 26
<212> TYPE: PRT
<213> ORGANISM: Artificial Sequence
<220> FEATURE:
<223> OTHER INFORMATION: framework sequence H1

<400> SEQUENCE: 30

Glu Val Gln Leu Val Glu Ser Gly Gly Gly Ser Val Gln Pro Gly Gly
1               5                   10                  15

Ser Leu Arg Leu Ser Cys Thr Ala Ser Gly
            20                  25

<210> SEQ ID NO 31
<211> LENGTH: 14
<212> TYPE: PRT
<213> ORGANISM: Artificial Sequence
<220> FEATURE:
<223> OTHER INFORMATION: framework sequence H2

<400> SEQUENCE: 31

Trp Val Arg Gln Ala Pro Gly Lys Gly Leu Glu Trp Val Gly
1               5                   10

<210> SEQ ID NO 32
<211> LENGTH: 32
<212> TYPE: PRT
<213> ORGANISM: Artificial Sequence
<220> FEATURE:
<223> OTHER INFORMATION: framework sequence H3

<400> SEQUENCE: 32

Arg Phe Thr Ile Ser Arg Asp Thr Ser Lys Asn Thr Val Tyr Leu Gln
1               5                   10                  15

Met Asn Ser Leu Arg Ala Glu Asp Thr Ala Ser Tyr Tyr Cys Ala Arg
            20                  25                  30

<210> SEQ ID NO 33
<211> LENGTH: 11
<212> TYPE: PRT
<213> ORGANISM: Artificial Sequence
<220> FEATURE:
<223> OTHER INFORMATION: framework sequence H4

<400> SEQUENCE: 33

Trp Gly Gln Gly Thr Thr Val Thr Val Ser Ser
1               5                   10

<210> SEQ ID NO 34
<211> LENGTH: 248
<212> TYPE: PRT
<213> ORGANISM: Artificial Sequence
<220> FEATURE:
<223> OTHER INFORMATION: CDR-L1_D32X
<220> FEATURE:
<221> NAME/KEY: misc_feature
<222> LOCATION: (30)..(30)
<223> OTHER INFORMATION: Xaa can be any naturally occurring amino acid

<400> SEQUENCE: 34

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Xaa Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr

Leu Gln Met Asn Ser Leu Arg Ala Glu Asp Thr Ala Val Tyr Tyr Cys
                210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 35
<211> LENGTH: 248
<212> TYPE: PRT
<213> ORGANISM: Artificial Sequence
<220> FEATURE:
<223> OTHER INFORMATION: Variant CDR-L1_N33X
<220> FEATURE:
<221> NAME/KEY: misc_feature
<222> LOCATION: (31)..(31)
<223> OTHER INFORMATION: Xaa can be any naturally occurring amino acid

<400> SEQUENCE: 35

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Xaa Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 36
<211> LENGTH: 248
<212> TYPE: PRT
<213> ORGANISM: Artificial Sequence
<220> FEATURE:

<223> OTHER INFORMATION: Variant CDR-L1_W40X
<220> FEATURE:
<221> NAME/KEY: misc_feature
<222> LOCATION: (32)..(32)
<223> OTHER INFORMATION: Xaa can be any naturally occurring amino acid

<400> SEQUENCE: 36

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Xaa
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
            165                 170                 175

Val Gly Ile Ile Tyr Asp Ser Ala Ser Thr Tyr Tyr Ala Ser Trp Ala
        180                 185                 190

Lys Gly Arg Phe Thr Ile Ser Arg Asp Thr Ser Lys Asn Thr Val Tyr
    195                 200                 205

Leu Gln Met Asn Ser Leu Arg Ala Glu Asp Thr Ala Val Tyr Tyr Cys
210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
            245

<210> SEQ ID NO 37
<211> LENGTH: 248
<212> TYPE: PRT
<213> ORGANISM: Artificial Sequence
<220> FEATURE:
<223> OTHER INFORMATION: Variant CDR-L2_R58X
<220> FEATURE:
<221> NAME/KEY: misc_feature
<222> LOCATION: (50)..(50)
<223> OTHER INFORMATION: Xaa can be any naturally occurring amino acid

<400> SEQUENCE: 37

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Xaa Ala Ser Thr Leu Ala Ser Gly Val Pro Ser Arg Phe Ser Gly
    50              55                  60

Ser Gly Ser Gly Ala Glu Phe Thr Leu Thr Ile Ser Ser Leu Gln Pro
65              70                  75                  80

Asp Asp Phe Ala Thr Tyr Tyr Cys Gln Asn Thr Gly Gly Val Ser
                85              90              95

Ile Ala Phe Gly Gln Gly Thr Lys Leu Thr Val Leu Gly Gly Gly
            100             105             110

Gly Ser Gly Gly Gly Gly Ser Gly Gly Gly Ser Gly Gly Gly Gly
        115             120             125

Ser Glu Val Gln Leu Val Glu Ser Gly Gly Leu Val Gln Pro Gly
130             135             140

Gly Ser Leu Arg Leu Ser Cys Thr Ala Ser Gly Phe Ser Leu Ser Ser
145             150             155             160

Ala Ala Met Ala Trp Val Arg Gln Ala Pro Gly Lys Gly Leu Glu Trp
                165             170             175

Val Gly Ile Ile Tyr Asp Ser Ala Ser Thr Tyr Tyr Ala Ser Trp Ala
            180             185             190

Lys Gly Arg Phe Thr Ile Ser Arg Asp Thr Ser Lys Asn Thr Val Tyr
            195             200             205

Leu Gln Met Asn Ser Leu Arg Ala Glu Asp Thr Ala Val Tyr Tyr Cys
210             215             220

Ala Arg Glu Arg Ala Ile Phe Ser Gly Asp Phe Val Leu Trp Gly Gln
225             230             235             240

Gly Thr Leu Val Thr Val Ser Ser
                245

<210> SEQ ID NO 38
<211> LENGTH: 248
<212> TYPE: PRT
<213> ORGANISM: Artificial Sequence
<220> FEATURE:
<223> OTHER INFORMATION: Variant CDR-L2_T69X
<220> FEATURE:
<221> NAME/KEY: misc_feature
<222> LOCATION: (53)..(53)
<223> OTHER INFORMATION: Xaa can be any naturally occurring amino acid

<400> SEQUENCE: 38

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Xaa Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65              70                  75                  80

Asp Asp Phe Ala Thr Tyr Tyr Cys Gln Asn Thr Gly Gly Val Ser
                85              90              95

Ile Ala Phe Gly Gln Gly Thr Lys Leu Thr Val Leu Gly Gly Gly
            100             105             110

Gly Ser Gly Gly Gly Gly Ser Gly Gly Gly Ser Gly Gly Gly Gly
        115             120             125

Ser Glu Val Gln Leu Val Glu Ser Gly Gly Leu Val Gln Pro Gly
130             135             140

```
Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 39
<211> LENGTH: 248
<212> TYPE: PRT
<213> ORGANISM: Artificial Sequence
<220> FEATURE:
<223> OTHER INFORMATION: Variant CDR-L3_T109X
<220> FEATURE:
<221> NAME/KEY: misc_feature
<222> LOCATION: (91)..(91)
<223> OTHER INFORMATION: Xaa can be any naturally occurring amino acid

<400> SEQUENCE: 39

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Xaa Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
```

Gly Thr Leu Val Thr Val Ser Ser
            245

<210> SEQ ID NO 40
<211> LENGTH: 248
<212> TYPE: PRT
<213> ORGANISM: Artificial Sequence
<220> FEATURE:
<223> OTHER INFORMATION: Variant CDR-L3_G111X
<220> FEATURE:
<221> NAME/KEY: misc_feature
<222> LOCATION: (93)..(93)
<223> OTHER INFORMATION: Xaa can be any naturally occurring amino acid

<400> SEQUENCE: 40

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Xaa Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
            245

<210> SEQ ID NO 41
<211> LENGTH: 248
<212> TYPE: PRT
<213> ORGANISM: Artificial Sequence
<220> FEATURE:
<223> OTHER INFORMATION: Variant CDR-L3_G112X
<220> FEATURE:
<221> NAME/KEY: misc_feature
<222> LOCATION: (94)..(94)
<223> OTHER INFORMATION: Xaa can be any naturally occurring amino acid

<400> SEQUENCE: 41

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Xaa Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Gly Ser Gly Gly Gly Gly
            115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245
```

<210> SEQ ID NO 42
<211> LENGTH: 248
<212> TYPE: PRT
<213> ORGANISM: Artificial Sequence
<220> FEATURE:
<223> OTHER INFORMATION: Variant CDR-L3_V135X
<220> FEATURE:
<221> NAME/KEY: misc_feature
<222> LOCATION: (95)..(95)
<223> OTHER INFORMATION: Xaa can be any naturally occurring amino acid

<400> SEQUENCE: 42

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80
```

```
Asp Asp Phe Ala Thr Tyr Tyr Cys Gln Asn Thr Gly Gly Gly Xaa Ser
                85                  90                  95

Ile Ala Phe Gly Gln Gly Thr Lys Leu Thr Val Leu Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
            195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245
```

<210> SEQ ID NO 43
<211> LENGTH: 248
<212> TYPE: PRT
<213> ORGANISM: Artificial Sequence
<220> FEATURE:
<223> OTHER INFORMATION: Variant CDR-L3_S136X
<220> FEATURE:
<221> NAME/KEY: misc_feature
<222> LOCATION: (96)..(96)
<223> OTHER INFORMATION: Xaa can be any naturally occurring amino acid

<400> SEQUENCE: 43

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Xaa
                85                  90                  95

Ile Ala Phe Gly Gln Gly Thr Lys Leu Thr Val Leu Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175
```

```
Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
        210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 44
<211> LENGTH: 248
<212> TYPE: PRT
<213> ORGANISM: Artificial Sequence
<220> FEATURE:
<223> OTHER INFORMATION: Variant CDR-H1_S33X
<220> FEATURE:
<221> NAME/KEY: misc_feature
<222> LOCATION: (160)..(160)
<223> OTHER INFORMATION: Xaa can be any naturally occurring amino acid

<400> SEQUENCE: 44

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Xaa
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
        210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245
```

<210> SEQ ID NO 45
<211> LENGTH: 248
<212> TYPE: PRT
<213> ORGANISM: Artificial Sequence
<220> FEATURE:
<223> OTHER INFORMATION: Variant CDR-H1_A39X
<220> FEATURE:
<221> NAME/KEY: misc_feature
<222> LOCATION: (161)..(161)
<223> OTHER INFORMATION: Xaa can be any naturally occurring amino acid

<400> SEQUENCE: 45

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Xaa Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 46
<211> LENGTH: 248
<212> TYPE: PRT
<213> ORGANISM: Artificial Sequence
<220> FEATURE:
<223> OTHER INFORMATION: Variant CDR-H2_Y59X
<220> FEATURE:
<221> NAME/KEY: misc_feature
<222> LOCATION: (181)..(181)
<223> OTHER INFORMATION: Xaa can be any naturally occurring amino acid

<400> SEQUENCE: 46

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp

```
                    20                  25                  30
Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Ser Gly Gly Gly Ser Gly Gly Gly Gly
            115                 120                 125

Ser Glu Val Gln Leu Val Glu Ser Gly Gly Leu Val Gln Pro Gly
        130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Xaa Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
                195                 200                 205

Leu Gln Met Asn Ser Leu Arg Ala Glu Asp Thr Ala Val Tyr Tyr Cys
                210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 47
<211> LENGTH: 248
<212> TYPE: PRT
<213> ORGANISM: Artificial Sequence
<220> FEATURE:
<223> OTHER INFORMATION: Variant CDR-H2_D60X
<220> FEATURE:
<221> NAME/KEY: misc_feature
<222> LOCATION: (182)..(182)
<223> OTHER INFORMATION: Xaa can be any naturally occurring amino acid

<400> SEQUENCE: 47

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly
                100                 105                 110
```

```
Gly Ser Gly Gly Gly Ser Gly Gly Gly Ser Gly Gly Gly
            115                 120                 125

Ser Glu Val Gln Leu Val Glu Ser Gly Gly Leu Val Gln Pro Gly
            130                 135                 140

Gly Ser Leu Arg Leu Ser Cys Thr Ala Ser Gly Phe Ser Leu Ser
145                 150                 155                 160

Ala Ala Met Ala Trp Val Arg Gln Ala Pro Gly Lys Gly Leu Glu Trp
                165                 170                 175

Val Gly Ile Ile Tyr Xaa Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
                195                 200                 205

Leu Gln Met Asn Ser Leu Arg Ala Glu Asp Thr Ala Val Tyr Tyr Cys
            210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 48
<211> LENGTH: 248
<212> TYPE: PRT
<213> ORGANISM: Artificial Sequence
<220> FEATURE:
<223> OTHER INFORMATION: Variant CDR-H2_Y69X
<220> FEATURE:
<221> NAME/KEY: misc_feature
<222> LOCATION: (187)..(187)
<223> OTHER INFORMATION: Xaa can be any naturally occurring amino acid

<400> SEQUENCE: 48

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Gly Leu Val Gln Pro Gly
            130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Xaa Tyr Ala Ser Trp Ala
                180                 185                 190

Lys Gly Arg Phe Thr Ile Ser Arg Asp Thr Ser Lys Asn Thr Val Tyr
                195                 200                 205
```

```
Leu Gln Met Asn Ser Leu Arg Ala Glu Asp Thr Ala Val Tyr Tyr Cys
            210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245
```

<210> SEQ ID NO 49
<211> LENGTH: 248
<212> TYPE: PRT
<213> ORGANISM: Artificial Sequence
<220> FEATURE:
<223> OTHER INFORMATION: Variant CDR-H3_R110X
<220> FEATURE:
<221> NAME/KEY: misc_feature
<222> LOCATION: (228)..(228)
<223> OTHER INFORMATION: Xaa can be any naturally occurring amino acid

<400> SEQUENCE: 49

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Gly Ser Gly Gly Gly Gly
            115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
            210                 215                 220

Ala Arg Glu Xaa Ala Ile Phe Ser Gly Asp Phe Val Leu Trp Gly Gln
225                 230                 235                 240

Gly Thr Leu Val Thr Val Ser Ser
                245
```

<210> SEQ ID NO 50
<211> LENGTH: 248
<212> TYPE: PRT
<213> ORGANISM: Artificial Sequence
<220> FEATURE:
<223> OTHER INFORMATION: Variant CDR-H3_A111X

```
<220> FEATURE:
<221> NAME/KEY: misc_feature
<222> LOCATION: (229)..(229)
<223> OTHER INFORMATION: Xaa can be any naturally occurring amino acid

<400> SEQUENCE: 50
```

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
                115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
                195                 200                 205

Leu Gln Met Asn Ser Leu Arg Ala Glu Asp Thr Ala Val Tyr Tyr Cys
        210                 215                 220

Ala Arg Glu Arg Xaa Ile Phe Ser Gly Asp Phe Val Leu Trp Gly Gln
225                 230                 235                 240

Gly Thr Leu Val Thr Val Ser Ser
                245

```
<210> SEQ ID NO 51
<211> LENGTH: 248
<212> TYPE: PRT
<213> ORGANISM: Artificial Sequence
<220> FEATURE:
<223> OTHER INFORMATION: Variant CDR-H3_I112X
<220> FEATURE:
<221> NAME/KEY: misc_feature
<222> LOCATION: (230)..(230)
<223> OTHER INFORMATION: Xaa can be any naturally occurring amino acid

<400> SEQUENCE: 51
```

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly

-continued

```
            50                  55                  60
Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                     85                  90                  95

Ile Ala Phe Gly Gln Gly Thr Lys Leu Thr Val Leu Gly Gly Gly Gly
                    100                 105                 110

Gly Ser Gly Gly Gly Gly Ser Gly Gly Gly Ser Gly Gly Gly Gly Gly
                    115                 120                 125

Ser Glu Val Gln Leu Val Glu Ser Gly Gly Gly Leu Val Gln Pro Gly
                130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                    165                 170                 175

Val Gly Ile Ile Tyr Asp Ser Ala Ser Thr Tyr Tyr Ala Ser Trp Ala
                    180                 185                 190

Lys Gly Arg Phe Thr Ile Ser Arg Asp Thr Ser Lys Asn Thr Val Tyr
                    195                 200                 205

Leu Gln Met Asn Ser Leu Arg Ala Glu Asp Thr Ala Val Tyr Tyr Cys
                210                 215                 220

Ala Arg Glu Arg Ala Xaa Phe Ser Gly Asp Phe Val Leu Trp Gly Gln
225                 230                 235                 240

Gly Thr Leu Val Thr Val Ser Ser
                    245
```

<210> SEQ ID NO 52
<211> LENGTH: 248
<212> TYPE: PRT
<213> ORGANISM: Artificial Sequence
<220> FEATURE:
<223> OTHER INFORMATION: Variant CDR-H3_F113X
<220> FEATURE:
<221> NAME/KEY: misc_feature
<222> LOCATION: (231)..(231)
<223> OTHER INFORMATION: Xaa can be any naturally occurring amino acid

<400> SEQUENCE: 52

```
Glu Ile Val Met Thr Gln Ser Pro Ser Thr Leu Ser Ala Ser Val Gly
  1               5                  10                  15

Asp Arg Val Ile Ile Thr Cys Gln Ala Ser Gln Ser Ile Asp Asn Trp
                 20                  25                  30

Leu Ser Trp Tyr Gln Gln Lys Pro Gly Lys Ala Pro Lys Leu Leu Ile
             35                  40                  45

Tyr Arg Ala Ser Thr Leu Ala Ser Gly Val Pro Ser Arg Phe Ser Gly
         50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                     85                  90                  95

Ile Ala Phe Gly Gln Gly Thr Lys Leu Thr Val Leu Gly Gly Gly Gly
                    100                 105                 110

Gly Ser Gly Gly Gly Gly Ser Gly Gly Gly Ser Gly Gly Gly Gly Gly
                    115                 120                 125

Ser Glu Val Gln Leu Val Glu Ser Gly Gly Gly Leu Val Gln Pro Gly
                130                 135                 140
```

```
Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Xaa Ser Gly Asp Phe Val Leu Trp Gly Gln
225                 230                 235                 240

Gly Thr Leu Val Thr Val Ser Ser
                245

<210> SEQ ID NO 53
<211> LENGTH: 248
<212> TYPE: PRT
<213> ORGANISM: Artificial Sequence
<220> FEATURE:
<223> OTHER INFORMATION: Variant CDR-H3_S114X
<220> FEATURE:
<221> NAME/KEY: misc_feature
<222> LOCATION: (232)..(232)
<223> OTHER INFORMATION: Xaa can be any naturally occurring amino acid

<400> SEQUENCE: 53

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Xaa Gly Asp Phe Val Leu Trp Gly Gln
225                 230                 235                 240
```

```
<210> SEQ ID NO 54
<211> LENGTH: 248
<212> TYPE: PRT
<213> ORGANISM: Artificial Sequence
<220> FEATURE:
<223> OTHER INFORMATION: Variant CDR-H3_G115X
<220> FEATURE:
<221> NAME/KEY: misc_feature
<222> LOCATION: (233)..(233)
<223> OTHER INFORMATION: Xaa can be any naturally occurring amino acid

<400> SEQUENCE: 54
```

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Xaa Asp Phe Val Leu Trp Gly Gln
225                 230                 235                 240

Gly Thr Leu Val Thr Val Ser Ser
            245

```
<210> SEQ ID NO 55
<211> LENGTH: 248
<212> TYPE: PRT
<213> ORGANISM: Artificial Sequence
<220> FEATURE:
<223> OTHER INFORMATION: Variant CDR-H3_D135X
<220> FEATURE:
<221> NAME/KEY: misc_feature
<222> LOCATION: (234)..(234)
<223> OTHER INFORMATION: Xaa can be any naturally occurring amino acid

<400> SEQUENCE: 55
```

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Gly Ser Gly Gly Gly Gly
            115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
            195                 200                 205

Leu Gln Met Asn Ser Leu Arg Ala Glu Asp Thr Ala Val Tyr Tyr Cys
210                 215                 220

Ala Arg Glu Arg Ala Ile Phe Ser Gly Xaa Phe Val Leu Trp Gly Gln
225                 230                 235                 240

Gly Thr Leu Val Thr Val Ser Ser
                245

<210> SEQ ID NO 56
<211> LENGTH: 248
<212> TYPE: PRT
<213> ORGANISM: Artificial Sequence
<220> FEATURE:
<223> OTHER INFORMATION: Variant CDR-H3_F136X
<220> FEATURE:
<221> NAME/KEY: misc_feature
<222> LOCATION: (235)..(235)
<223> OTHER INFORMATION: Xaa can be any naturally occurring amino acid

<400> SEQUENCE: 56

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser

```
            85                  90                  95
Ile Ala Phe Gly Gln Gly Thr Lys Leu Thr Val Leu Gly Gly Gly
            100                 105                 110

Gly Ser Gly Gly Gly Ser Gly Gly Gly Ser Gly Gly Gly
            115                 120                 125

Ser Glu Val Gln Leu Val Glu Ser Gly Gly Leu Val Gln Pro Gly
            130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                    165                 170                 175

Val Gly Ile Ile Tyr Asp Ser Ala Ser Thr Tyr Tyr Ala Ser Trp Ala
                    180                 185                 190

Lys Gly Arg Phe Thr Ile Ser Arg Asp Thr Ser Lys Asn Thr Val Tyr
                    195                 200                 205

Leu Gln Met Asn Ser Leu Arg Ala Glu Asp Thr Ala Val Tyr Tyr Cys
            210                 215                 220

Ala Arg Glu Arg Ala Ile Phe Ser Gly Asp Xaa Val Leu Trp Gly Gln
225                 230                 235                 240

Gly Thr Leu Val Thr Val Ser Ser
                    245
```

<210> SEQ ID NO 57
<211> LENGTH: 248
<212> TYPE: PRT
<213> ORGANISM: Artificial Sequence
<220> FEATURE:
<223> OTHER INFORMATION: Variant CDR-H3_V137X
<220> FEATURE:
<221> NAME/KEY: misc_feature
<222> LOCATION: (236)..(236)
<223> OTHER INFORMATION: Xaa can be any naturally occurring amino acid

<400> SEQUENCE: 57

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                    85                  90                  95

Ile Ala Phe Gly Gln Gly Thr Lys Leu Thr Val Leu Gly Gly Gly
            100                 105                 110

Gly Ser Gly Gly Gly Ser Gly Gly Gly Ser Gly Gly Gly
            115                 120                 125

Ser Glu Val Gln Leu Val Glu Ser Gly Gly Leu Val Gln Pro Gly
            130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                    165                 170                 175
```

```
Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Xaa Leu Trp Gly Gln
225                 230                 235                 240

Gly Thr Leu Val Thr Val Ser Ser
                245

<210> SEQ ID NO 58
<211> LENGTH: 248
<212> TYPE: PRT
<213> ORGANISM: Artificial Sequence
<220> FEATURE:
<223> OTHER INFORMATION: Variant CDR-H3_L138X
<220> FEATURE:
<221> NAME/KEY: misc_feature
<222> LOCATION: (237)..(237)
<223> OTHER INFORMATION: Xaa can be any naturally occurring amino acid

<400> SEQUENCE: 58

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Xaa Trp Gly Gln
225                 230                 235                 240

Gly Thr Leu Val Thr Val Ser Ser
                245

<210> SEQ ID NO 59
```

<211> LENGTH: 248
<212> TYPE: PRT
<213> ORGANISM: Artificial Sequence
<220> FEATURE:
<223> OTHER INFORMATION: Variant DLX2464

<400> SEQUENCE: 59

```
Glu Ile Val Met Thr Gln Ser Pro Ser Thr Leu Ser Ala Ser Val Gly
1               5                   10                  15
Asp Arg Val Ile Ile Thr Cys Gln Ala Ser Gln Ser Ile Asp Asn Trp
            20                  25                  30
Leu Ser Trp Tyr Gln Gln Lys Pro Gly Lys Ala Pro Lys Leu Leu Ile
        35                  40                  45
Tyr Arg Ala Ser Thr Leu Ala Ser Gly Val Pro Ser Arg Phe Ser Gly
    50                  55                  60
Ser Gly Ser Gly Ala Glu Phe Thr Leu Thr Ile Ser Ser Leu Gln Pro
65                  70                  75                  80
Asp Asp Phe Ala Thr Tyr Tyr Cys Gln Asn Thr Gly Gly Val Ser
                85                  90                  95
Ile Ala Phe Gly Gln Gly Thr Lys Leu Thr Val Leu Gly Gly Gly Gly
                100                 105                 110
Gly Ser Gly Gly Gly Gly Ser Gly Gly Gly Ser Gly Gly Gly Gly
                115                 120                 125
Ser Glu Val Gln Leu Val Glu Ser Gly Gly Leu Val Gln Pro Gly
                130                 135                 140
Gly Ser Leu Arg Leu Ser Cys Thr Ala Ser Gly Phe Ser Leu Ser Ser
145                 150                 155                 160
Ala Ala Met Ala Trp Val Arg Gln Ala Pro Gly Lys Gly Leu Glu Trp
                165                 170                 175
Val Gly Ile Ile Tyr Asp Ser Ala Ser Thr Tyr Tyr Ala Ser Trp Ala
                180                 185                 190
Lys Gly Arg Phe Thr Ile Ser Arg Asp Thr Ser Lys Asn Thr Val Tyr
                195                 200                 205
Leu Gln Met Asn Ser Leu Arg Ala Glu Asp Thr Ala Val Tyr Tyr Cys
            210                 215                 220
Ala Arg Glu Arg Gln Ile Phe Ser Gly Asp Met Ala Gly Trp Gly Gln
225                 230                 235                 240
Gly Thr Leu Val Thr Val Ser Ser
                245
```

<210> SEQ ID NO 60
<211> LENGTH: 248
<212> TYPE: PRT
<213> ORGANISM: Artificial Sequence
<220> FEATURE:
<223> OTHER INFORMATION: Variant DLX2465

<400> SEQUENCE: 60

```
Glu Ile Val Met Thr Gln Ser Pro Ser Thr Leu Ser Ala Ser Val Gly
1               5                   10                  15
Asp Arg Val Ile Ile Thr Cys Gln Ala Ser Gln Ser Ile Asp Asn Trp
            20                  25                  30
Leu Ser Trp Tyr Gln Gln Lys Pro Gly Lys Ala Pro Lys Leu Leu Ile
        35                  40                  45
Tyr Arg Ala Ser Thr Leu Ala Ser Gly Val Pro Ser Arg Phe Ser Gly
    50                  55                  60
Ser Gly Ser Gly Ala Glu Phe Thr Leu Thr Ile Ser Ser Leu Gln Pro
```

```
                65                  70                  75                  80
Asp Asp Phe Ala Thr Tyr Tyr Cys Gln Asn Thr Gly Gly Gly Val Ser
                    85                  90                  95

Ile Ala Phe Gly Gln Gly Thr Lys Leu Thr Val Leu Gly Gly Gly Gly
                    100                 105                 110

Gly Ser Gly Gly Gly Gly Ser Gly Gly Gly Ser Gly Gly Gly Gly
                115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                    165                 170                 175

Val Gly Ile Ile Tyr Asp Ser Ala Ser Thr Tyr Tyr Ala Ser Trp Ala
                    180                 185                 190

Lys Gly Arg Phe Thr Ile Ser Arg Asp Thr Ser Lys Asn Thr Val Tyr
                    195                 200                 205

Leu Gln Met Asn Ser Leu Arg Ala Glu Asp Thr Ala Val Tyr Tyr Cys
                210                 215                 220

Ala Arg Glu Arg Asn Ile Phe Ser Gly Asp Met Asp Leu Trp Gly Gln
225                 230                 235                 240

Gly Thr Leu Val Thr Val Ser Ser
                245

<210> SEQ ID NO 61
<211> LENGTH: 248
<212> TYPE: PRT
<213> ORGANISM: Artificial Sequence
<220> FEATURE:
<223> OTHER INFORMATION: Variant DLX2466

<400> SEQUENCE: 61

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Gly Lys Tyr
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Ala Gly Gly Gly Val Ser
                    85                  90                  95

Ile Ala Phe Gly Gln Gly Thr Lys Leu Thr Val Leu Gly Gly Gly Gly
                    100                 105                 110

Gly Ser Gly Gly Gly Gly Ser Gly Gly Gly Gly Ser Gly Gly Gly Gly
                115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Asp Ala Met Ala Trp Val Arg Gln Ala Pro Gly Lys Gly Leu Glu Trp
                    165                 170                 175

Val Gly Ile Ile Tyr Asp Ser Ala Ser Thr Tyr Tyr Ala Ser Trp Ala
```

```
                180                 185                 190

Lys Gly Arg Phe Thr Ile Ser Arg Asp Thr Ser Lys Asn Thr Val Tyr
            195                 200                 205

Leu Gln Met Asn Ser Leu Arg Ala Glu Asp Thr Ala Val Tyr Tyr Cys
        210                 215                 220

Ala Arg Glu Arg Asn Ile Phe Ser Gly Asp Met Ala Gly Trp Gly Gln
225                 230                 235                 240

Gly Thr Leu Val Thr Val Ser Ser
                245

<210> SEQ ID NO 62
<211> LENGTH: 248
<212> TYPE: PRT
<213> ORGANISM: Artificial Sequence
<220> FEATURE:
<223> OTHER INFORMATION: Variant DLX2467

<400> SEQUENCE: 62

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile His Asn Trp
            20                  25                  30

Leu Ser Trp Tyr Gln Gln Lys Pro Gly Lys Ala Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Ser Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Leu Val Gln Pro Gly Gly
130                 135                 140

Ser Leu Arg Leu Ser Cys Thr Ala Ser Gly Phe Ser Leu Ser Arg
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Met Ile Phe Ser Gly Asp Phe Val Leu Trp Gly Gln
225                 230                 235                 240

Gly Thr Leu Val Thr Val Ser Ser
                245

<210> SEQ ID NO 63
<211> LENGTH: 248
<212> TYPE: PRT
<213> ORGANISM: Artificial Sequence
<220> FEATURE:
<223> OTHER INFORMATION: Variant DLX2468
```

<400> SEQUENCE: 63

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Gly Asn Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Ala Gly Gly Gly Thr Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly Gly
        115                 120                 125

Ser Glu Val Gln Leu Val Glu Ser Gly Gly Leu Val Gln Pro Gly Gly
130                 135                 140

Gly Ser Leu Arg Leu Ser Cys Thr Ala Ser Gly Phe Ser Leu Ser Ser
145                 150                 155                 160

Ser Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Asn Ile Phe Ser Gly Asp Met Val Leu Trp Gly Gln
225                 230                 235                 240

Gly Thr Leu Val Thr Val Ser Ser
                245

<210> SEQ ID NO 64
<211> LENGTH: 248
<212> TYPE: PRT
<213> ORGANISM: Artificial Sequence
<220> FEATURE:
<223> OTHER INFORMATION: Variant DLX2475

<400> SEQUENCE: 64

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Lys Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val His
                85                  90                  95

```
Ile Ala Phe Gly Gln Gly Thr Lys Leu Thr Val Leu Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Tyr Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
                195                 200                 205

Leu Gln Met Asn Ser Leu Arg Ala Glu Asp Thr Ala Val Tyr Tyr Cys
                210                 215                 220

Ala Arg Glu Arg Ala Ile Phe Ser Gly Asp Phe Lys Leu Trp Gly Gln
225                 230                 235                 240

Gly Thr Leu Val Thr Val Ser Ser
                245
```

<210> SEQ ID NO 65
<211> LENGTH: 248
<212> TYPE: PRT
<213> ORGANISM: Artificial Sequence
<220> FEATURE:
<223> OTHER INFORMATION: Variant DLX2476

<400> SEQUENCE: 65

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Ser Trp
                20                  25                  30

Leu Ser Trp Tyr Gln Gln Lys Pro Gly Lys Ala Pro Lys Leu Leu Ile
                35                  40                  45

Tyr Arg Ala Ser Thr Leu Ala Ser Gly Val Pro Ser Arg Phe Ser Gly
                50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Arg Asp Thr Ser Lys Asn Thr Val Tyr
                195                 200                 205
```

Leu Gln Met Asn Ser Leu Arg Ala Glu Asp Thr Ala Val Tyr Tyr Cys
    210                 215                 220

Ala Arg Glu Arg Asp Ile Phe Ser Gly Asp Phe Val Gly Trp Gly Gln
225                 230                 235                 240

Gly Thr Leu Val Thr Val Ser Ser
                245

<210> SEQ ID NO 66
<211> LENGTH: 248
<212> TYPE: PRT
<213> ORGANISM: Artificial Sequence
<220> FEATURE:
<223> OTHER INFORMATION: Variant DLX2480

<400> SEQUENCE: 66

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Ile Asn
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Leu Val Gln Pro Gly
130                 135                 140

Gly Ser Leu Arg Leu Ser Cys Thr Ala Ser Gly Phe Ser Leu Ser Asp
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Gln Ile Phe Ser Gly Asp Phe Val Leu Trp Gly Gln
225                 230                 235                 240

Gly Thr Leu Val Thr Val Ser Ser
                245

<210> SEQ ID NO 67
<211> LENGTH: 248
<212> TYPE: PRT
<213> ORGANISM: Artificial Sequence
<220> FEATURE:
<223> OTHER INFORMATION: Variant DLX2543

<400> SEQUENCE: 67

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Ala Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 68
<211> LENGTH: 248
<212> TYPE: PRT
<213> ORGANISM: Artificial Sequence
<220> FEATURE:
<223> OTHER INFORMATION: Variant DLX2529

<400> SEQUENCE: 68

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Gly Asn Trp
            20                  25                  30

Leu Ser Trp Tyr Gln Gln Lys Pro Gly Lys Ala Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Glu Asp Phe Ala Thr Tyr Tyr Cys Gln Asn Thr Gly Gly Gly Ile Asn
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

```
Ser Glu Val Gln Leu Val Glu Ser Gly Gly Gly Leu Val Gln Pro Gly
        130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245
```

<210> SEQ ID NO 69
<211> LENGTH: 249
<212> TYPE: PRT
<213> ORGANISM: Artificial Sequence
<220> FEATURE:
<223> OTHER INFORMATION: Variant DLX2547

<400> SEQUENCE: 69

```
Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ser Trp Tyr Gln Gln Lys Pro Gly Lys Ala Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile
                85                  90                  95

Asn Ile Ala Phe Gly Gln Gly Thr Lys Leu Glu Ile Lys Arg Gly Gly
                100                 105                 110

Gly Gly Ser Gly Gly Gly Gly Ser Gly Gly Gly Ser Gly Gly Gly
            115                 120                 125

Gly Ser Glu Val Gln Leu Val Glu Ser Gly Gly Gly Leu Val Gln Pro
        130                 135                 140

Gly Gly Ser Leu Arg Leu Ser Cys Thr Ala Ser Gly Phe Ser Leu Ser
145                 150                 155                 160

Ser Ala Ala Met Ala Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Arg Asp Thr Ser Lys Asn Thr Val
        195                 200                 205

Tyr Leu Gln Met Asn Ser Leu Arg Ala Glu Asp Thr Ala Val Tyr Tyr
    210                 215                 220

Cys Ala Arg Glu Arg Ala Ile Phe Ser Gly Asp Phe Val Leu Trp Gly
225                 230                 235                 240
```

Gln Gly Thr Leu Val Thr Val Ser Ser
                245

<210> SEQ ID NO 70
<211> LENGTH: 248
<212> TYPE: PRT
<213> ORGANISM: Artificial Sequence
<220> FEATURE:
<223> OTHER INFORMATION: Variant DLX2528

<400> SEQUENCE: 70

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Asn Ala Gly Ala Thr
                    85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Val Leu Trp Gly Gln
225                 230                 235                 240

Gly Thr Leu Val Thr Val Ser Ser
                245

<210> SEQ ID NO 71
<211> LENGTH: 248
<212> TYPE: PRT
<213> ORGANISM: Artificial Sequence
<220> FEATURE:
<223> OTHER INFORMATION: Variant DLX2585

<400> SEQUENCE: 71

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile

```
                35                  40                  45
Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                 85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
                115                 120                 125

Ser Glu Val Gln Leu Val Glu Ser Gly Gly Leu Val Gln Pro Gly
                130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
                180                 185                 190

Lys Gly Arg Phe Thr Ile Ser Lys Asp Thr Ser Lys Asn Thr Val Tyr
                195                 200                 205

Leu Gln Met Asn Ser Leu Arg Ala Glu Asp Thr Ala Val Tyr Tyr Cys
                210                 215                 220

Ala Arg Glu Arg Ala Ile Phe Ser Gly Asp Phe Asp Tyr Trp Gly Gln
225                 230                 235                 240

Gly Thr Leu Val Thr Val Ser Ser
                245

<210> SEQ ID NO 72
<211> LENGTH: 248
<212> TYPE: PRT
<213> ORGANISM: Artificial Sequence
<220> FEATURE:
<223> OTHER INFORMATION: Variant DLX2545

<400> SEQUENCE: 72

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
                 20                  25                  30

Leu Ser Trp Tyr Gln Gln Lys Pro Gly Lys Ala Pro Lys Leu Leu Ile
             35                  40                  45

Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                 85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Gly Ser Gly Gly Gly Gly
                115                 120                 125

Ser Glu Val Gln Leu Val Glu Ser Gly Gly Gly Leu Val Gln Pro Gly
                130                 135                 140

Gly Ser Leu Arg Leu Ser Cys Thr Ala Ser Gly Phe Ser Leu Ser Ser
```

```
                145                 150                 155                 160
Ala Ala Met Ala Trp Val Arg Gln Ala Pro Gly Lys Gly Leu Glu Trp
                    165                 170                 175
Ile Gly Ile Ile Tyr Asp Ser Ala Ser Thr Tyr Tyr Ala Ser Trp Ala
                    180                 185                 190
Lys Gly Arg Phe Thr Ile Ser Arg Asp Thr Ser Lys Asn Thr Leu Tyr
                    195                 200                 205
Leu Gln Met Asn Ser Leu Arg Ala Glu Asp Thr Ala Val Tyr Phe Cys
                    210                 215                 220
Ala Arg Glu Arg Asn Ile Phe Ser Gly Asp Met Val Leu Trp Gly Gln
225                 230                 235                 240
Gly Thr Thr Val Thr Val Ser Ser
                    245

<210> SEQ ID NO 73
<211> LENGTH: 248
<212> TYPE: PRT
<213> ORGANISM: Artificial Sequence
<220> FEATURE:
<223> OTHER INFORMATION: Variant DLX2531

<400> SEQUENCE: 73

Glu Ile Val Met Thr Gln Ser Pro Ser Thr Leu Ser Ala Ser Val Gly
1               5                   10                  15
Asp Arg Val Ile Ile Thr Cys Gln Ala Ser Gln Ser Ile Asp Asn Trp
                    20                  25                  30
Leu Ser Trp Tyr Gln Gln Lys Pro Gly Lys Ala Pro Lys Leu Leu Ile
                    35                  40                  45
Tyr Arg Ala Ser Thr Leu Ala Ser Gly Val Pro Ser Arg Phe Ser Gly
        50                  55                  60
Ser Gly Ser Gly Ala Glu Phe Thr Leu Thr Ile Ser Ser Leu Gln Pro
65                  70                  75                  80
Asp Asp Phe Ala Thr Tyr Tyr Cys Gln Asn Thr Gly Gly Gly Val Ser
                    85                  90                  95
Ile Ala Phe Gly Gln Gly Thr Lys Leu Thr Val Leu Gly Gly Gly Gly
                    100                 105                 110
Gly Ser Gly Gly Gly Gly Ser Gly Gly Gly Ser Gly Gly Gly Gly
                    115                 120                 125
Ser Glu Val Gln Leu Val Glu Ser Gly Gly Gly Asn Val Gln Pro Gly
                    130                 135                 140
Gly Ser Leu Arg Leu Ser Cys Thr Ala Ser Gly Phe Ser Leu Ser Asn
145                 150                 155                 160
Ser Ala Met Ala Trp Val Arg Gln Ala Pro Gly Lys Gly Leu Glu Trp
                    165                 170                 175
Val Gly Ile Ile Tyr Asp Ser Ala Ser Thr Tyr Tyr Ala Ser Trp Ala
                    180                 185                 190
Lys Gly Arg Phe Thr Ile Ser Arg Asp Asn Ser Lys Asn Thr Val Tyr
                    195                 200                 205
Leu Gln Met Asn Ser Leu Arg Ala Glu Asp Thr Ala Thr Tyr Tyr Cys
                    210                 215                 220
Ala Arg Glu Arg Ala Ile Phe Ser Gly Asp Phe Ala Leu Trp Gly Gln
225                 230                 235                 240
Gly Thr Leu Val Thr Val Ser Ser
                    245
```

```
<210> SEQ ID NO 74
<211> LENGTH: 248
<212> TYPE: PRT
<213> ORGANISM: Artificial Sequence
<220> FEATURE:
<223> OTHER INFORMATION: Variant DLX2586

<400> SEQUENCE: 74

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Ile Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Val Tyr
        195                 200                 205

Leu Gln Met Asn Ser Leu Arg Ala Glu Asp Thr Ala Val Tyr Phe Cys
210                 215                 220

Ala Arg Glu Arg Gln Ile Phe Ser Gly Asp Met Asp Gly Trp Gly Gln
225                 230                 235                 240

Gly Thr Leu Val Thr Val Ser Ser
                245

<210> SEQ ID NO 75
<211> LENGTH: 248
<212> TYPE: PRT
<213> ORGANISM: Artificial Sequence
<220> FEATURE:
<223> OTHER INFORMATION: Variant DLX2530

<400> SEQUENCE: 75

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60
```

```
Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                 85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Asn Val Gln Pro Gly
    130                 135                 140

Gly Ser Leu Arg Leu Ser Cys Thr Ala Ser Gly Phe Ser Leu Ser Asp
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Phe Tyr Ala Ser Trp Ala
                180                 185                 190

Lys Gly Arg Phe Thr Ile Ser Arg Asp Asn Ser Lys Asn Thr Leu Tyr
                195                 200                 205

Leu Gln Met Asn Ser Leu Arg Ala Glu Asp Thr Ala Thr Tyr Tyr Cys
    210                 215                 220

Ala Arg Glu Arg Asn Ile Phe Ser Gly Asp Met Ala Leu Trp Gly Gln
225                 230                 235                 240

Gly Thr Thr Val Thr Val Ser Ser
                245

<210> SEQ ID NO 76
<211> LENGTH: 248
<212> TYPE: PRT
<213> ORGANISM: Artificial Sequence
<220> FEATURE:
<223> OTHER INFORMATION: Variant DLX2548

<400> SEQUENCE: 76

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Ser
                 85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175
```

Ile Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Leu Tyr
        195                 200                 205

Leu Gln Met Asn Ser Leu Arg Ala Glu Asp Thr Ala Val Tyr Phe Cys
    210                 215                 220

Ala Arg Glu Arg Gln Ile Phe Ser Gly Asp Met Asp Gly Trp Gly Gln
225                 230                 235                 240

Gly Thr Thr Val Thr Val Ser Ser
                245

<210> SEQ ID NO 77
<211> LENGTH: 248
<212> TYPE: PRT
<213> ORGANISM: Artificial Sequence
<220> FEATURE:
<223> OTHER INFORMATION: Variant DLX2676

<400> SEQUENCE: 77

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Asn Ala Gly Gly Ala Thr Thr
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Asn Val Gln Pro Gly
    130                 135                 140

Gly Ser Leu Arg Leu Ser Cys Thr Ala Ser Gly Phe Ser Leu Ser Asp
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Phe Tyr Ala Ser Trp Ala
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Thr Tyr Tyr Cys
    210                 215                 220

Ala Arg Glu Arg Asn Ile Phe Ser Gly Asp Met Ala Leu Trp Gly Gln
225                 230                 235                 240

Gly Thr Thr Val Thr Val Ser Ser
                245

<210> SEQ ID NO 78
<211> LENGTH: 248
<212> TYPE: PRT
<213> ORGANISM: Artificial Sequence
<220> FEATURE:

<223> OTHER INFORMATION: Variant DLX2677

<400> SEQUENCE: 78

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Asn Ala Gly Gly Ala Thr Thr
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Asn Val Gln Pro Gly Gly
130                 135                 140

Ser Leu Arg Leu Ser Cys Thr Ala Ser Gly Phe Ser Leu Ser Asn
145                 150                 155                 160

Ser Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Asn Ser Lys Asn Thr Val Tyr
        195                 200                 205

Leu Gln Met Asn Ser Leu Arg Ala Glu Asp Thr Ala Thr Tyr Tyr Cys
210                 215                 220

Ala Arg Glu Arg Ala Ile Phe Ser Gly Asp Phe Ala Leu Trp Gly Gln
225                 230                 235                 240

Gly Thr Leu Val Thr Val Ser Ser
                245

<210> SEQ ID NO 79
<211> LENGTH: 248
<212> TYPE: PRT
<213> ORGANISM: Artificial Sequence
<220> FEATURE:
<223> OTHER INFORMATION: Variant DLX2678

<400> SEQUENCE: 79

Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Asn Ala Gly Gly Ala Thr Thr
                85                  90                  95

```
Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly
            115                 120                 125

Ser Glu Val Gln Leu Val Glu Ser Gly Gly Leu Val Gln Pro Gly
        130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Ile Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Leu Tyr
                195                 200                 205

Leu Gln Met Asn Ser Leu Arg Ala Glu Asp Thr Ala Val Tyr Phe Cys
        210                 215                 220

Ala Arg Glu Arg Gln Ile Phe Ser Gly Asp Met Asp Gly Trp Gly Gln
225                 230                 235                 240

Gly Thr Thr Val Thr Val Ser Ser
                245
```

<210> SEQ ID NO 80
<211> LENGTH: 248
<212> TYPE: PRT
<213> ORGANISM: Artificial Sequence
<220> FEATURE:
<223> OTHER INFORMATION: Variant DLX2679

<400> SEQUENCE: 80

```
Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Asn Ala Gly Gly Ala Thr Thr
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly
            115                 120                 125

Ser Glu Val Gln Leu Val Glu Ser Gly Gly Leu Val Gln Pro Gly
        130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Val Tyr
                195                 200                 205
```

Leu Gln Met Asn Ser Leu Arg Ala Glu Asp Thr Ala Val Tyr Tyr Cys
                210                 215                 220

Ala Arg Glu Arg Ala Ile Phe Ser Gly Asp Phe Asp Tyr Trp Gly Gln
225                 230                 235                 240

Gly Thr Leu Val Thr Val Ser Ser
                245

<210> SEQ ID NO 81
<211> LENGTH: 248
<212> TYPE: PRT
<213> ORGANISM: Artificial Sequence
<220> FEATURE:
<223> OTHER INFORMATION: Variant DLX2680

<400> SEQUENCE: 81

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Gly Asn Trp
                20                  25                  30

Leu Ser Trp Tyr Gln Gln Lys Pro Gly Lys Ala Pro Lys Leu Leu Ile
            35                  40                  45

Tyr Arg Ala Ser Asn Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Glu Asp Phe Ala Thr Tyr Tyr Cys Gln Asn Thr Gly Gly Gly Ile Asn
                85                  90                  95

Ile Ala Phe Gly Gln Gly Thr Lys Leu Thr Val Leu Gly Gly Gly Gly
                100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Asn Val Gln Pro Gly
            130                 135                 140

Gly Ser Leu Arg Leu Ser Cys Thr Ala Ser Gly Phe Ser Leu Ser Asp
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Phe Tyr Ala Ser Trp Ala
                180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Thr Tyr Tyr Cys
        210                 215                 220

Ala Arg Glu Arg Asn Ile Phe Ser Gly Asp Met Ala Leu Trp Gly Gln
225                 230                 235                 240

Gly Thr Thr Val Thr Val Ser Ser
                245

<210> SEQ ID NO 82
<211> LENGTH: 248
<212> TYPE: PRT
<213> ORGANISM: Artificial Sequence
<220> FEATURE:
<223> OTHER INFORMATION: Variant DLX2681

<400> SEQUENCE: 82

Glu Ile Val Met Thr Gln Ser Pro Ser Thr Leu Ser Ala Ser Val Gly

```
           1               5                  10                 15
Asp Arg Val Ile Ile Thr Cys Arg Ala Ser Gln Ser Ile Gly Asn Trp
            20                  25                 30

Leu Ser Trp Tyr Gln Gln Lys Pro Gly Lys Ala Pro Lys Leu Leu Ile
            35                  40                 45

Tyr Arg Ala Ser Asn Leu Ala Ser Gly Val Pro Ser Arg Phe Ser Gly
        50                  55                 60

Ser Gly Ser Gly Ala Glu Phe Thr Leu Thr Ile Ser Ser Leu Gln Pro
65                  70                  75                 80

Glu Asp Phe Ala Thr Tyr Tyr Cys Gln Asn Thr Gly Gly Gly Ile Asn
                85                  90                 95

Ile Ala Phe Gly Gln Gly Thr Lys Leu Thr Val Leu Gly Gly Gly Gly
            100                 105                110

Gly Ser Gly Gly Gly Gly Ser Gly Gly Gly Ser Gly Gly Gly Gly
            115                 120                125

Ser Glu Val Gln Leu Val Glu Ser Gly Gly Asn Val Gln Pro Gly
130                 135                 140

Gly Ser Leu Arg Leu Ser Cys Thr Ala Ser Gly Phe Ser Leu Ser Asn
145                 150                 155                160

Ser Ala Met Ala Trp Val Arg Gln Ala Pro Gly Lys Gly Leu Glu Trp
                165                 170                175

Val Gly Ile Ile Tyr Asp Ser Ala Ser Thr Tyr Tyr Ala Ser Trp Ala
            180                 185                190

Lys Gly Arg Phe Thr Ile Ser Arg Asp Asn Ser Lys Asn Thr Val Tyr
            195                 200                205

Leu Gln Met Asn Ser Leu Arg Ala Glu Asp Thr Ala Thr Tyr Tyr Cys
        210                 215                 220

Ala Arg Glu Arg Ala Ile Phe Ser Gly Asp Phe Ala Leu Trp Gly Gln
225                 230                 235                240

Gly Thr Leu Val Thr Val Ser Ser
                245
```

<210> SEQ ID NO 83
<211> LENGTH: 248
<212> TYPE: PRT
<213> ORGANISM: Artificial Sequence
<220> FEATURE:
<223> OTHER INFORMATION: Variant DLX2682

<400> SEQUENCE: 83

```
Glu Ile Val Met Thr Gln Ser Pro Ser Thr Leu Ser Ala Ser Val Gly
1               5                  10                 15

Asp Arg Val Ile Ile Thr Cys Arg Ala Ser Gln Ser Ile Gly Asn Trp
            20                  25                 30

Leu Ser Trp Tyr Gln Gln Lys Pro Gly Lys Ala Pro Lys Leu Leu Ile
            35                  40                 45

Tyr Arg Ala Ser Asn Leu Ala Ser Gly Val Pro Ser Arg Phe Ser Gly
        50                  55                 60

Ser Gly Ser Gly Ala Glu Phe Thr Leu Thr Ile Ser Ser Leu Gln Pro
65                  70                  75                 80

Glu Asp Phe Ala Thr Tyr Tyr Cys Gln Asn Thr Gly Gly Gly Ile Asn
                85                  90                 95

Ile Ala Phe Gly Gln Gly Thr Lys Leu Thr Val Leu Gly Gly Gly Gly
            100                 105                110

Gly Ser Gly Gly Gly Gly Ser Gly Gly Gly Gly Ser Gly Gly Gly Gly
```

```
              115                 120                 125
Ser Glu Val Gln Leu Val Glu Ser Gly Gly Leu Val Gln Pro Gly
        130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Ile Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Leu Tyr
                195                 200                 205

Leu Gln Met Asn Ser Leu Arg Ala Glu Asp Thr Ala Val Tyr Phe Cys
        210                 215                 220

Ala Arg Glu Arg Gln Ile Phe Ser Gly Asp Met Asp Gly Trp Gly Gln
225                 230                 235                 240

Gly Thr Thr Val Thr Val Ser Ser
                245
```

<210> SEQ ID NO 84
<211> LENGTH: 248
<212> TYPE: PRT
<213> ORGANISM: Artificial Sequence
<220> FEATURE:
<223> OTHER INFORMATION: Variant DLX2683

<400> SEQUENCE: 84

```
Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Gly Asn Trp
            20                  25                  30

Leu Ser Trp Tyr Gln Gln Lys Pro Gly Lys Ala Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Glu Asp Phe Ala Thr Tyr Tyr Cys Gln Asn Thr Gly Gly Gly Ile Asn
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Lys Asp Thr Ser Lys Asn Thr Val Tyr
        195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Asp Tyr Trp Gly Gln
```

<210> SEQ ID NO 85
<211> LENGTH: 248
<212> TYPE: PRT
<213> ORGANISM: Artificial Sequence
<220> FEATURE:
<223> OTHER INFORMATION: Variant DLX2684

<400> SEQUENCE: 85

```
Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Ala Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Asn Val Gln Pro Gly
130                 135                 140

Gly Ser Leu Arg Leu Ser Cys Thr Ala Ser Gly Phe Ser Leu Ser Asp
145                 150                 155                 160

Ala Ala Met Ala Trp Val Arg Gln Ala Pro Gly Lys Gly Leu Glu Trp
                165                 170                 175

Val Gly Ile Ile Tyr Asp Ser Ala Ser Thr Phe Tyr Ala Ser Trp Ala
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Thr Tyr Tyr Cys
    210                 215                 220

Ala Arg Glu Arg Asn Ile Phe Ser Gly Asp Met Ala Leu Trp Gly Gln
225                 230                 235                 240

Gly Thr Thr Val Thr Val Ser Ser
                245
```

<210> SEQ ID NO 86
<211> LENGTH: 248
<212> TYPE: PRT
<213> ORGANISM: Artificial Sequence
<220> FEATURE:
<223> OTHER INFORMATION: Variant DLX2685

<400> SEQUENCE: 86

```
Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Trp
            20                  25                  30
```

```
Leu Ser Trp Tyr Gln Gln Lys Pro Gly Lys Ala Pro Lys Leu Leu Ile
             35                  40                  45

Tyr Lys Ala Ser Thr Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Asn Ala Gly Gly Gly Val Ser
                 85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
            115                 120                 125

Ser Glu Val Gln Leu Val Glu Ser Gly Gly Gly Asn Val Gln Pro Gly
        130                 135                 140

Gly Ser Leu Arg Leu Ser Cys Thr Ala Ser Gly Phe Ser Leu Ser Asn
145                 150                 155                 160

Ser Ala Met Ala Trp Val Arg Gln Ala Pro Gly Lys Gly Leu Glu Trp
                165                 170                 175

Val Gly Ile Ile Tyr Asp Ser Ala Ser Thr Tyr Tyr Ala Ser Trp Ala
            180                 185                 190

Lys Gly Arg Phe Thr Ile Ser Arg Asp Asn Ser Lys Asn Thr Val Tyr
        195                 200                 205

Leu Gln Met Asn Ser Leu Arg Ala Glu Asp Thr Ala Thr Tyr Tyr Cys
    210                 215                 220

Ala Arg Glu Arg Ala Ile Phe Ser Gly Asp Phe Ala Leu Trp Gly Gln
225                 230                 235                 240

Gly Thr Leu Val Thr Val Ser Ser
                245

<210> SEQ ID NO 87
<211> LENGTH: 249
<212> TYPE: PRT
<213> ORGANISM: Artificial Sequence
<220> FEATURE:
<223> OTHER INFORMATION: Variant DLX2686

<400> SEQUENCE: 87

Met Glu Ile Val Met Thr Gln Ser Pro Ser Thr Leu Ser Ala Ser Val
 1               5                  10                  15

Gly Asp Arg Val Thr Ile Thr Cys Gln Ala Ser Gln Ser Ile Ser Ser
                20                  25                  30

Trp Leu Ser Trp Tyr Gln Gln Lys Pro Gly Lys Ala Pro Lys Leu Leu
             35                  40                  45

Ile Tyr Lys Ala Ser Thr Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Gln Asn Ala Gly Gly Gly Val
                 85                  90                  95

Ser Ile Ala Phe Gly Gln Gly Thr Lys Leu Thr Val Leu Gly Gly Gly
            100                 105                 110

Gly Gly Ser Gly Gly Gly Gly Ser Gly Gly Gly Ser Gly Gly Gly Gly
            115                 120                 125

Gly Ser Glu Val Gln Leu Val Glu Ser Gly Gly Gly Leu Val Gln Pro
        130                 135                 140
```

```
Gly Gly Ser Leu Arg Leu Ser Cys Thr Val Ser Gly Phe Ser Leu Ser
145                 150                 155                 160

Ser Tyr Ala Met Ser Trp Val Arg Gln Ala Pro Gly Lys Gly Leu Glu
            165                 170                 175

Trp Ile Gly Ile Ile Tyr Asp Ser Ala Ser Thr Tyr Tyr Ala Ser Trp
                180                 185                 190

Ala Lys Gly Arg Phe Thr Ile Ser Lys Asp Thr Ser Lys Asn Thr Leu
            195                 200                 205

Tyr Leu Gln Met Asn Ser Leu Arg Ala Glu Asp Thr Ala Val Tyr Phe
        210                 215                 220

Cys Ala Arg Glu Arg Gln Ile Phe Ser Gly Asp Met Asp Gly Trp Gly
225                 230                 235                 240

Gln Gly Thr Thr Val Thr Val Ser Ser
                245
```

<210> SEQ ID NO 88
<211> LENGTH: 248
<212> TYPE: PRT
<213> ORGANISM: Artificial Sequence
<220> FEATURE:
<223> OTHER INFORMATION: Variant DLX2687

<400> SEQUENCE: 88

```
Glu Ile Val Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Asn Ala Gly Gly Gly Val Ser
                85                  90                  95

Ile Ala Phe Gly Gln Gly Thr Lys Leu Thr Val Leu Gly Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Val Ser Gly Phe Ser Leu Ser Ser
145                 150                 155                 160

Tyr Ala Met Ser Trp Val Arg Gln Ala Pro Gly Lys Gly Leu Glu Trp
            165                 170                 175

Val Gly Ile Ile Tyr Asp Ser Ala Ser Thr Tyr Tyr Ala Ser Trp Ala
        180                 185                 190

Lys Gly Arg Phe Thr Ile Ser Lys Asp Thr Ser Lys Asn Thr Val Tyr
    195                 200                 205

Leu Gln Met Asn Ser Leu Arg Ala Glu Asp Thr Ala Val Tyr Tyr Cys
    210                 215                 220

Ala Arg Glu Arg Ala Ile Phe Ser Gly Asp Phe Asp Tyr Trp Gly Gln
225                 230                 235                 240

Gly Thr Leu Val Thr Val Ser Ser
                245
```

-continued

```
<210> SEQ ID NO 89
<211> LENGTH: 249
<212> TYPE: PRT
<213> ORGANISM: Artificial Sequence
<220> FEATURE:
<223> OTHER INFORMATION: Variant DLX2689

<400> SEQUENCE: 89
```

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Lys Ala Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Asn Ala Gly Gly Gly Ile
                85                  90                  95

Asn Ile Ala Phe Gly Gln Gly Thr Lys Val Glu Ile Lys Arg Gly Gly
            100                 105                 110

Gly Gly Ser Gly Gly Gly Gly Ser Gly Gly Gly Gly Ser Gly Gly Gly
            115                 120                 125

Gly Ser Glu Val Gln Leu Val Glu Ser Gly Gly Asn Val Gln Pro
            130                 135                 140

Gly Gly Ser Leu Arg Leu Ser Cys Thr Ala Ser Gly Phe Ser Leu Ser
145                 150                 155                 160

Asn Ser Ala Met Ala Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Arg Asp Asn Ser Lys Asn Thr Val
            195                 200                 205

Tyr Leu Gln Met Asn Ser Leu Arg Ala Glu Asp Thr Ala Thr Tyr Tyr
            210                 215                 220

Cys Ala Arg Glu Arg Ala Ile Phe Ser Gly Asp Phe Ala Leu Trp Gly
225                 230                 235                 240

Gln Gly Thr Leu Val Thr Val Ser Ser
                245

```
<210> SEQ ID NO 90
<211> LENGTH: 249
<212> TYPE: PRT
<213> ORGANISM: Artificial Sequence
<220> FEATURE:
<223> OTHER INFORMATION: Variant DLX2690

<400> SEQUENCE: 90
```

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Lys Ala Ser Thr Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Asn Ala Gly Gly Gly Ile
                85                  90                  95

Asn Ile Ala Phe Gly Gln Gly Thr Lys Val Glu Ile Lys Arg Gly Gly
            100                 105                 110

Gly Gly Ser Gly Gly Gly Gly Ser Gly Gly Gly Ser Gly Gly Gly
            115                 120                 125

Gly Ser Glu Val Gln Leu Val Glu Ser Gly Gly Leu Val Gln Pro
130                 135                 140

Gly Gly Ser Leu Arg Leu Ser Cys Thr Val Ser Gly Phe Ser Leu Ser
145                 150                 155                 160

Ser Tyr Ala Met Ser Trp Val Arg Gln Ala Pro Gly Lys Gly Leu Glu
                165                 170                 175

Trp Ile Gly Ile Ile Tyr Asp Ser Ala Ser Thr Tyr Tyr Ala Ser Trp
            180                 185                 190

Ala Lys Gly Arg Phe Thr Ile Ser Lys Asp Thr Ser Lys Asn Thr Leu
        195                 200                 205

Tyr Leu Gln Met Asn Ser Leu Arg Ala Glu Asp Thr Ala Val Tyr Phe
210                 215                 220

Cys Ala Arg Glu Arg Gln Ile Phe Ser Gly Asp Met Asp Gly Trp Gly
225                 230                 235                 240

Gln Gly Thr Thr Val Thr Val Ser Ser
                245

<210> SEQ ID NO 91
<211> LENGTH: 249
<212> TYPE: PRT
<213> ORGANISM: Artificial Sequence
<220> FEATURE:
<223> OTHER INFORMATION: Variant DLX2691

<400> SEQUENCE: 91

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ser Trp Tyr Gln Gln Lys Pro Gly Lys Ala Pro Lys Leu Leu
        35                  40                  45

Ile Tyr Lys Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Asn Ala Gly Gly Gly Ile
                85                  90                  95

Asn Ile Ala Phe Gly Gln Gly Thr Lys Val Glu Ile Lys Arg Gly Gly
            100                 105                 110

Gly Gly Ser Gly Gly Gly Gly Ser Gly Gly Gly Ser Gly Gly Gly
            115                 120                 125

Gly Ser Glu Val Gln Leu Val Glu Ser Gly Gly Leu Val Gln Pro
130                 135                 140

Gly Gly Ser Leu Arg Leu Ser Cys Thr Val Ser Gly Phe Ser Leu Ser
145                 150                 155                 160

Ser Tyr Ala Met Ser Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Lys Asp Thr Ser Lys Asn Thr Val
            195                 200                 205

Tyr Leu Gln Met Asn Ser Leu Arg Ala Glu Asp Thr Ala Val Tyr Tyr
            210                 215                 220

Cys Ala Arg Glu Arg Ala Ile Phe Ser Gly Asp Phe Asp Tyr Trp Gly
225                 230                 235                 240

Gln Gly Thr Leu Val Thr Val Ser Ser
            245

<210> SEQ ID NO 92
<211> LENGTH: 249
<212> TYPE: PRT
<213> ORGANISM: Artificial Sequence
<220> FEATURE:
<223> OTHER INFORMATION: Variant DLX2692

<400> SEQUENCE: 92

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ser Trp Tyr Gln Gln Lys Pro Gly Lys Ala Pro Lys Leu Leu
            35                  40                  45

Ile Tyr Arg Ala Ser Thr Leu Ala Ser Gly Val Pro Ser Arg Phe Ser
        50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile
                85                  90                  95

Asn Ile Ala Phe Gly Gln Gly Thr Lys Leu Glu Ile Lys Arg Gly Gly
            100                 105                 110

Gly Gly Ser Gly Gly Gly Gly Ser Gly Gly Gly Gly Ser Gly Gly Gly
            115                 120                 125

Gly Ser Glu Val Gln Leu Val Glu Ser Gly Gly Asn Val Gln Pro
        130                 135                 140

Gly Gly Ser Leu Arg Leu Ser Cys Thr Ala Ser Gly Phe Ser Leu Ser
145                 150                 155                 160

Asp Ala Ala Met Ala Trp Val Arg Gln Ala Pro Gly Lys Gly Leu Glu
                165                 170                 175

Trp Val Gly Ile Ile Tyr Asp Ser Ala Ser Thr Phe Tyr Ala Ser Trp
            180                 185                 190

Ala Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Thr Tyr Tyr
            210                 215                 220

Cys Ala Arg Glu Arg Asn Ile Phe Ser Gly Asp Met Ala Leu Trp Gly
225                 230                 235                 240

Gln Gly Thr Thr Val Thr Val Ser Ser
            245

<210> SEQ ID NO 93
<211> LENGTH: 249
<212> TYPE: PRT
<213> ORGANISM: Artificial Sequence
<220> FEATURE:
<223> OTHER INFORMATION: Variant DLX2693

<400> SEQUENCE: 93

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Arg Ala Ser Thr Leu Ala Ser Gly Val Pro Ser Arg Phe Ser
        50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile
                85                  90                  95

Asn Ile Ala Phe Gly Gln Gly Thr Lys Leu Glu Ile Lys Arg Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Asn Val Gln Pro
130                 135                 140

Gly Gly Ser Leu Arg Leu Ser Cys Thr Ala Ser Gly Phe Ser Leu Ser
145                 150                 155                 160

Asn Ser Ala Met Ala Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Arg Asp Asn Ser Lys Asn Thr Val
        195                 200                 205

Tyr Leu Gln Met Asn Ser Leu Arg Ala Glu Asp Thr Ala Thr Tyr Tyr
    210                 215                 220

Cys Ala Arg Glu Arg Ala Ile Phe Ser Gly Asp Phe Ala Leu Trp Gly
225                 230                 235                 240

Gln Gly Thr Leu Val Thr Val Ser Ser
                245

<210> SEQ ID NO 94
<211> LENGTH: 249
<212> TYPE: PRT
<213> ORGANISM: Artificial Sequence
<220> FEATURE:
<223> OTHER INFORMATION: Variant DLX2694

<400> SEQUENCE: 94

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Arg Ala Ser Thr Leu Ala Ser Gly Val Pro Ser Arg Phe Ser
        50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile

```
            85                  90                  95
Asn Ile Ala Phe Gly Gln Gly Thr Lys Leu Glu Ile Lys Arg Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Thr Val Ser Gly Phe Ser Leu Ser
145                 150                 155                 160

Ser Tyr Ala Met Ser Trp Val Arg Gln Ala Pro Gly Lys Gly Leu Glu
                165                 170                 175

Trp Ile Gly Ile Ile Tyr Asp Ser Ala Ser Thr Tyr Tyr Ala Ser Trp
            180                 185                 190

Ala Lys Gly Arg Phe Thr Ile Ser Lys Asp Thr Ser Lys Asn Thr Leu
            195                 200                 205

Tyr Leu Gln Met Asn Ser Leu Arg Ala Glu Asp Thr Ala Val Tyr Phe
    210                 215                 220

Cys Ala Arg Glu Arg Gln Ile Phe Ser Gly Asp Met Asp Gly Trp Gly
225                 230                 235                 240

Gln Gly Thr Thr Val Thr Val Ser Ser
                245

<210> SEQ ID NO 95
<211> LENGTH: 249
<212> TYPE: PRT
<213> ORGANISM: Artificial Sequence
<220> FEATURE:
<223> OTHER INFORMATION: Variant DLX2695

<400> SEQUENCE: 95

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ser Trp Tyr Gln Gln Lys Pro Gly Lys Ala Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile
                85                  90                  95

Asn Ile Ala Phe Gly Gln Gly Thr Lys Leu Glu Ile Lys Arg Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Thr Val Ser Gly Phe Ser Leu Ser
145                 150                 155                 160

Ser Tyr Ala Met Ser Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Lys Asp Thr Ser Lys Asn Thr Val
```

```
                195                 200                 205
Tyr Leu Gln Met Asn Ser Leu Arg Ala Glu Asp Thr Ala Val Tyr Tyr
        210                 215                 220

Cys Ala Arg Glu Arg Ala Ile Phe Ser Gly Asp Phe Asp Tyr Trp Gly
225                 230                 235                 240

Gln Gly Thr Leu Val Thr Val Ser Ser
                245
```

<210> SEQ ID NO 96
<211> LENGTH: 109
<212> TYPE: PRT
<213> ORGANISM: Artificial Sequence
<220> FEATURE:
<223> OTHER INFORMATION: VL CDR-L1_D32X
<220> FEATURE:
<221> NAME/KEY: misc_feature
<222> LOCATION: (30)..(30)
<223> OTHER INFORMATION: Xaa can be any naturally occurring amino acid

<400> SEQUENCE: 96

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Xaa Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly
            100                 105
```

<210> SEQ ID NO 97
<211> LENGTH: 109
<212> TYPE: PRT
<213> ORGANISM: Artificial Sequence
<220> FEATURE:
<223> OTHER INFORMATION: VL CDR-L1_N33X
<220> FEATURE:
<221> NAME/KEY: misc_feature
<222> LOCATION: (31)..(31)
<223> OTHER INFORMATION: Xaa can be any naturally occurring amino acid

<400> SEQUENCE: 97

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Xaa Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly
```

<210> SEQ ID NO 98
<211> LENGTH: 109
<212> TYPE: PRT
<213> ORGANISM: Artificial Sequence
<220> FEATURE:
<223> OTHER INFORMATION: VL CDR-L1_W40X
<220> FEATURE:
<221> NAME/KEY: misc_feature
<222> LOCATION: (32)..(32)
<223> OTHER INFORMATION: Xaa can be any naturally occurring amino acid

<400> SEQUENCE: 98

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Xaa
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly
            100                 105

<210> SEQ ID NO 99
<211> LENGTH: 109
<212> TYPE: PRT
<213> ORGANISM: Artificial Sequence
<220> FEATURE:
<223> OTHER INFORMATION: VL CDR-L2_R58X
<220> FEATURE:
<221> NAME/KEY: misc_feature
<222> LOCATION: (50)..(50)
<223> OTHER INFORMATION: Xaa can be any naturally occurring amino acid

<400> SEQUENCE: 99

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Xaa Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly
            100                 105

<210> SEQ ID NO 100
<211> LENGTH: 109
<212> TYPE: PRT
<213> ORGANISM: Artificial Sequence
<220> FEATURE:
<223> OTHER INFORMATION: VL CDR-L2_T69X
<220> FEATURE:
<221> NAME/KEY: misc_feature
<222> LOCATION: (53)..(53)
<223> OTHER INFORMATION: Xaa can be any naturally occurring amino acid

<400> SEQUENCE: 100

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Xaa Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly
            100                 105

<210> SEQ ID NO 101
<211> LENGTH: 109
<212> TYPE: PRT
<213> ORGANISM: Artificial Sequence
<220> FEATURE:
<223> OTHER INFORMATION: VL CDR-L3_T109X
<220> FEATURE:
<221> NAME/KEY: misc_feature
<222> LOCATION: (91)..(91)
<223> OTHER INFORMATION: Xaa can be any naturally occurring amino acid

<400> SEQUENCE: 101

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Xaa Gly Gly Val Ser
                85                  90                  95

Ile Ala Phe Gly Gln Gly Thr Lys Leu Thr Val Leu Gly
            100                 105

<210> SEQ ID NO 102
<211> LENGTH: 109
<212> TYPE: PRT
<213> ORGANISM: Artificial Sequence
<220> FEATURE:
<223> OTHER INFORMATION: VL CDR-L3_G111X
<220> FEATURE:
<221> NAME/KEY: misc_feature
<222> LOCATION: (93)..(93)
<223> OTHER INFORMATION: Xaa can be any naturally occurring amino acid

<400> SEQUENCE: 102

Glu Ile Val Met Thr Gln Ser Pro Ser Thr Leu Ser Ala Ser Val Gly
1               5                   10                  15

```
Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Xaa Gly Val Ser
                 85                  90                  95

Ile Ala Phe Gly Gln Gly Thr Lys Leu Thr Val Leu Gly
            100                 105

<210> SEQ ID NO 103
<211> LENGTH: 109
<212> TYPE: PRT
<213> ORGANISM: Artificial Sequence
<220> FEATURE:
<223> OTHER INFORMATION: VL CDR-L3_G112X
<220> FEATURE:
<221> NAME/KEY: misc_feature
<222> LOCATION: (94)..(94)
<223> OTHER INFORMATION: Xaa can be any naturally occurring amino acid

<400> SEQUENCE: 103

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Xaa Val Ser
                 85                  90                  95

Ile Ala Phe Gly Gln Gly Thr Lys Leu Thr Val Leu Gly
            100                 105

<210> SEQ ID NO 104
<211> LENGTH: 109
<212> TYPE: PRT
<213> ORGANISM: Artificial Sequence
<220> FEATURE:
<223> OTHER INFORMATION: VL CDR-L3_V135X
<220> FEATURE:
<221> NAME/KEY: misc_feature
<222> LOCATION: (95)..(95)
<223> OTHER INFORMATION: Xaa can be any naturally occurring amino acid

<400> SEQUENCE: 104

Glu Ile Val Met Thr Gln Ser Pro Ser Thr Leu Ser Ala Ser Val Gly
 1               5                  10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
 50                  55                  60
```

```
Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Xaa Ser
                 85                  90                  95

Ile Ala Phe Gly Gln Gly Thr Lys Leu Thr Val Leu Gly
            100                 105

<210> SEQ ID NO 105
<211> LENGTH: 109
<212> TYPE: PRT
<213> ORGANISM: Artificial Sequence
<220> FEATURE:
<223> OTHER INFORMATION: VL CDR-L3_S136X
<220> FEATURE:
<221> NAME/KEY: misc_feature
<222> LOCATION: (96)..(96)
<223> OTHER INFORMATION: Xaa can be any naturally occurring amino acid

<400> SEQUENCE: 105

Glu Ile Val Met Thr Gln Ser Pro Ser Thr Leu Ser Ala Ser Val Gly
 1               5                   10                  15

Asp Arg Val Ile Ile Thr Cys Gln Ala Ser Gln Ser Ile Asp Asn Trp
                 20                  25                  30

Leu Ser Trp Tyr Gln Gln Lys Pro Gly Lys Ala Pro Lys Leu Leu Ile
             35                  40                  45

Tyr Arg Ala Ser Thr Leu Ala Ser Gly Val Pro Ser Arg Phe Ser Gly
 50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Gly Val Xaa
                 85                  90                  95

Ile Ala Phe Gly Gln Gly Thr Lys Leu Thr Val Leu Gly
            100                 105

<210> SEQ ID NO 106
<211> LENGTH: 119
<212> TYPE: PRT
<213> ORGANISM: Artificial Sequence
<220> FEATURE:
<223> OTHER INFORMATION: VH CDR-H1_S33X
<220> FEATURE:
<221> NAME/KEY: misc_feature
<222> LOCATION: (31)..(31)
<223> OTHER INFORMATION: Xaa can be any naturally occurring amino acid

<400> SEQUENCE: 106

Glu Val Gln Leu Val Glu Ser Gly Gly Gly Leu Val Gln Pro Gly Gly
 1               5                   10                  15

Ser Leu Arg Leu Ser Cys Thr Ala Ser Gly Phe Ser Leu Ser Xaa Ala
                 20                  25                  30

Ala Met Ala Trp Val Arg Gln Ala Pro Gly Lys Gly Leu Glu Trp Val
             35                  40                  45

Gly Ile Ile Tyr Asp Ser Ala Ser Thr Tyr Tyr Ala Ser Trp Ala Lys
 50                  55                  60

Gly Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Arg Ala Ile Phe Ser Gly Asp Phe Val Leu Trp Gly Gln Gly
            100                 105                 110
```

Thr Leu Val Thr Val Ser Ser
        115

<210> SEQ ID NO 107
<211> LENGTH: 119
<212> TYPE: PRT
<213> ORGANISM: Artificial Sequence
<220> FEATURE:
<223> OTHER INFORMATION: VH CDR-H1_A39X
<220> FEATURE:
<221> NAME/KEY: misc_feature
<222> LOCATION: (32)..(32)
<223> OTHER INFORMATION: Xaa can be any naturally occurring amino acid

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Xaa
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Val Leu Trp Gly Gln Gly
            100                 105                 110

Thr Leu Val Thr Val Ser Ser
        115

<210> SEQ ID NO 108
<211> LENGTH: 119
<212> TYPE: PRT
<213> ORGANISM: Artificial Sequence
<220> FEATURE:
<223> OTHER INFORMATION: VH CDR-H2_Y59X
<220> FEATURE:
<221> NAME/KEY: misc_feature
<222> LOCATION: (52)..(52)
<223> OTHER INFORMATION: Xaa can be any naturally occurring amino acid

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Xaa Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Val Leu Trp Gly Gln Gly
            100                 105                 110

Thr Leu Val Thr Val Ser Ser
        115

```
<210> SEQ ID NO 109
<211> LENGTH: 119
<212> TYPE: PRT
<213> ORGANISM: Artificial Sequence
<220> FEATURE:
<223> OTHER INFORMATION: VH CDR-H2_D60X
<220> FEATURE:
<221> NAME/KEY: misc_feature
<222> LOCATION: (53)..(53)
<223> OTHER INFORMATION: Xaa can be any naturally occurring amino acid

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Xaa Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Val Leu Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Artificial Sequence
<220> FEATURE:
<223> OTHER INFORMATION: VH CDR-H2_Y69X
<220> FEATURE:
<221> NAME/KEY: misc_feature
<222> LOCATION: (58)..(58)
<223> OTHER INFORMATION: Xaa can be any naturally occurring amino acid

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Xaa Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Val Leu Trp Gly Gln Gly
            100                 105                 110

Thr Leu Val Thr Val Ser Ser
        115

<210> SEQ ID NO 111
```

<211> LENGTH: 119
<212> TYPE: PRT
<213> ORGANISM: Artificial Sequence
<220> FEATURE:
<223> OTHER INFORMATION: VH CDR-H3_R110X
<220> FEATURE:
<221> NAME/KEY: misc_feature
<222> LOCATION: (99)..(99)
<223> OTHER INFORMATION: Xaa can be any naturally occurring amino acid

<400> SEQUENCE: 111

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Xaa Ala Ile Phe Ser Gly Asp Phe Val Leu Trp Gly Gln Gly
            100                 105                 110

Thr Leu Val Thr Val Ser Ser
        115

<210> SEQ ID NO 112
<211> LENGTH: 119
<212> TYPE: PRT
<213> ORGANISM: Artificial Sequence
<220> FEATURE:
<223> OTHER INFORMATION: VH CDR-H3_A111X
<220> FEATURE:
<221> NAME/KEY: misc_feature
<222> LOCATION: (100)..(100)
<223> OTHER INFORMATION: Xaa can be any naturally occurring amino acid

<400> SEQUENCE: 112

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Xaa Ile Phe Ser Gly Asp Phe Val Leu Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Artificial Sequence

```
<220> FEATURE:
<223> OTHER INFORMATION: VH CDR-H3_I112X
<220> FEATURE:
<221> NAME/KEY: misc_feature
<222> LOCATION: (101)..(101)
<223> OTHER INFORMATION: Xaa can be any naturally occurring amino acid

<400> SEQUENCE: 113
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Phe | Ser | Leu | Ser | Ser | Ala |
|---|---|---|---|---|---|---|---|---|---|---|---|---|---|---|---|
| | | | 20 | | | | | 25 | | | | | 30 | | |

| Ala | Met | Ala | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Ile | Ile | Tyr | Asp | Ser | Ala | Ser | Thr | Tyr | Tyr | Ala | Ser | Trp | Ala | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Thr | Ser | Lys | Asn | Thr | Val | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Glu | Arg | Ala | Xaa | Phe | Ser | Gly | Asp | Phe | Val | Leu | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser |
|---|---|---|---|---|---|---|
| | | | 115 | | | |

```
<210> SEQ ID NO 114
<211> LENGTH: 119
<212> TYPE: PRT
<213> ORGANISM: Artificial Sequence
<220> FEATURE:
<223> OTHER INFORMATION: VH CDR-H3_F113X
<220> FEATURE:
<221> NAME/KEY: misc_feature
<222> LOCATION: (102)..(102)
<223> OTHER INFORMATION: Xaa can be any naturally occurring amino acid

<400> SEQUENCE: 114
```

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Thr | Ala | Ser | Gly | Phe | Ser | Leu | Ser | Ser | Ala |
|---|---|---|---|---|---|---|---|---|---|---|---|---|---|---|---|
| | | | 20 | | | | | 25 | | | | | 30 | | |

| Ala | Met | Ala | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Gly | Ile | Ile | Tyr | Asp | Ser | Ala | Ser | Thr | Tyr | Tyr | Ala | Ser | Trp | Ala | Lys |
|---|---|---|---|---|---|---|---|---|---|---|---|---|---|---|---|
| | 50 | | | | | 55 | | | | | 60 | | | | |

| Gly | Arg | Phe | Thr | Ile | Ser | Arg | Asp | Thr | Ser | Lys | Asn | Thr | Val | Tyr | Leu |
|---|---|---|---|---|---|---|---|---|---|---|---|---|---|---|---|
| 65 | | | | | 70 | | | | | 75 | | | | | 80 |

| Gln | Met | Asn | Ser | Leu | Arg | Ala | Glu | Asp | Thr | Ala | Val | Tyr | Tyr | Cys | Ala |
|---|---|---|---|---|---|---|---|---|---|---|---|---|---|---|---|
| | | | | 85 | | | | | 90 | | | | | 95 | |

| Arg | Glu | Arg | Ala | Ile | Xaa | Ser | Gly | Asp | Phe | Val | Leu | Trp | Gly | Gln | Gly |
|---|---|---|---|---|---|---|---|---|---|---|---|---|---|---|---|
| | | | 100 | | | | | 105 | | | | | 110 | | |

| Thr | Leu | Val | Thr | Val | Ser | Ser |
|---|---|---|---|---|---|---|
| | | | 115 | | | |

```
<210> SEQ ID NO 115
<211> LENGTH: 119
<212> TYPE: PRT
<213> ORGANISM: Artificial Sequence
<220> FEATURE:
<223> OTHER INFORMATION: VH CDR-H3_S114X
<220> FEATURE:
```

<221> NAME/KEY: misc_feature
<222> LOCATION: (103)..(103)
<223> OTHER INFORMATION: Xaa can be any naturally occurring amino acid

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Xaa Gly Asp Phe Val Leu Trp Gly Gln Gly
            100                 105                 110

Thr Leu Val Thr Val Ser Ser
        115

<210> SEQ ID NO 116
<211> LENGTH: 119
<212> TYPE: PRT
<213> ORGANISM: Artificial Sequence
<220> FEATURE:
<223> OTHER INFORMATION: VH CDR-H3_G115X
<220> FEATURE:
<221> NAME/KEY: misc_feature
<222> LOCATION: (104)..(104)
<223> OTHER INFORMATION: Xaa can be any naturally occurring amino acid

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Xaa Asp Phe Val Leu Trp Gly Gln Gly
            100                 105                 110

Thr Leu Val Thr Val Ser Ser
        115

<210> SEQ ID NO 117
<211> LENGTH: 119
<212> TYPE: PRT
<213> ORGANISM: Artificial Sequence
<220> FEATURE:
<223> OTHER INFORMATION: VH CDR-H3_D135X
<220> FEATURE:
<221> NAME/KEY: misc_feature
<222> LOCATION: (105)..(105)
<223> OTHER INFORMATION: Xaa can be any naturally occurring amino acid

<400> SEQUENCE: 117

Glu Val Gln Leu Val Glu Ser Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Xaa Phe Val Leu Trp Gly Gln Gly
            100                 105                 110

Thr Leu Val Thr Val Ser Ser
        115

<210> SEQ ID NO 118
<211> LENGTH: 119
<212> TYPE: PRT
<213> ORGANISM: Artificial Sequence
<220> FEATURE:
<223> OTHER INFORMATION: VH CDR-H3_F136X
<220> FEATURE:
<221> NAME/KEY: misc_feature
<222> LOCATION: (106)..(106)
<223> OTHER INFORMATION: Xaa can be any naturally occurring amino acid

<400> SEQUENCE: 118

Glu Val Gln Leu Val Glu Ser Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Xaa Val Leu Trp Gly Gln Gly
            100                 105                 110

Thr Leu Val Thr Val Ser Ser
        115

<210> SEQ ID NO 119
<211> LENGTH: 119
<212> TYPE: PRT
<213> ORGANISM: Artificial Sequence
<220> FEATURE:
<223> OTHER INFORMATION: VH CDR-H3_V137X
<220> FEATURE:
<221> NAME/KEY: misc_feature
<222> LOCATION: (107)..(107)
<223> OTHER INFORMATION: Xaa can be any naturally occurring amino acid

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Xaa Leu Trp Gly Gln Gly
            100                 105                 110

Thr Leu Val Thr Val Ser Ser
        115
```

<210> SEQ ID NO 120
<211> LENGTH: 119
<212> TYPE: PRT
<213> ORGANISM: Artificial Sequence
<220> FEATURE:
<223> OTHER INFORMATION: VH CDR-H3_L138X
<220> FEATURE:
<221> NAME/KEY: misc_feature
<222> LOCATION: (108)..(108)
<223> OTHER INFORMATION: Xaa can be any naturally occurring amino acid

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Val Xaa Trp Gly Gln Gly
            100                 105                 110

Thr Leu Val Thr Val Ser Ser
        115
```

<210> SEQ ID NO 121
<211> LENGTH: 119
<212> TYPE: PRT
<213> ORGANISM: Artificial Sequence
<220> FEATURE:
<223> OTHER INFORMATION: VH DLX2464

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
```

```
            35                  40                  45
Gly Ile Ile Tyr Asp Ser Ala Ser Thr Tyr Tyr Ala Ser Trp Ala Lys
        50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Gln Ile Phe Ser Gly Asp Met Ala Gly Trp Gly Gln Gly
            100                 105                 110

Thr Leu Val Thr Val Ser Ser
        115

<210> SEQ ID NO 122
<211> LENGTH: 119
<212> TYPE: PRT
<213> ORGANISM: Artificial Sequence
<220> FEATURE:
<223> OTHER INFORMATION: VH DLX2465

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Asn Ile Phe Ser Gly Asp Met Asp Leu Trp Gly Gln Gly
            100                 105                 110

Thr Leu Val Thr Val Ser Ser
        115

<210> SEQ ID NO 123
<211> LENGTH: 109
<212> TYPE: PRT
<213> ORGANISM: Artificial Sequence
<220> FEATURE:
<223> OTHER INFORMATION: VL DLX2466

<400> SEQUENCE: 123

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Gly Lys Tyr
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Ala Gly Gly Val Ser
                85                  90                  95
```

Ile Ala Phe Gly Gln Gly Thr Lys Leu Thr Val Leu Gly
            100                 105

<210> SEQ ID NO 124
<211> LENGTH: 119
<212> TYPE: PRT
<213> ORGANISM: Artificial Sequence
<220> FEATURE:
<223> OTHER INFORMATION: VH DLX2466

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Asp
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Asn Ile Phe Ser Gly Asp Met Ala Gly Trp Gly Gln Gly
            100                 105                 110

Thr Leu Val Thr Val Ser Ser
        115

<210> SEQ ID NO 125
<211> LENGTH: 109
<212> TYPE: PRT
<213> ORGANISM: Artificial Sequence
<220> FEATURE:
<223> OTHER INFORMATION: VL DLX2467

<400> SEQUENCE: 125

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile His Asn Trp
            20                  25                  30

Leu Ser Trp Tyr Gln Gln Lys Pro Gly Lys Ala Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Ser Ser
                85                  90                  95

Ile Ala Phe Gly Gln Gly Thr Lys Leu Thr Val Leu Gly
            100                 105

<210> SEQ ID NO 126
<211> LENGTH: 119
<212> TYPE: PRT
<213> ORGANISM: Artificial Sequence
<220> FEATURE:
<223> OTHER INFORMATION: VH DLX 2467

<400> SEQUENCE: 126

Glu Val Gln Leu Val Glu Ser Gly Gly Gly Leu Val Gln Pro Gly Gly

```
                1               5                   10                  15
            Ser Leu Arg Leu Ser Cys Thr Ala Ser Gly Phe Ser Leu Ser Arg Ala
                            20                  25                  30

Ala Met Ala Trp Val Arg Gln Ala Pro Gly Lys Gly Leu Glu Trp Val
                            35                  40                  45

Gly Ile Ile Tyr Asp Ser Ala Ser Thr Tyr Tyr Ala Ser Trp Ala Lys
                            50                  55                  60

Gly Arg Phe Thr Ile Ser Arg Asp Thr Ser Lys Asn Thr Val Tyr Leu
            65                  70                  75                  80

Gln Met Asn Ser Leu Arg Ala Glu Asp Thr Ala Val Tyr Tyr Cys Ala
                            85                  90                  95

Arg Glu Arg Met Ile Phe Ser Gly Asp Phe Val Leu Trp Gly Gln Gly
                            100                 105                 110

Thr Leu Val Thr Val Ser Ser
                            115

<210> SEQ ID NO 127
<211> LENGTH: 109
<212> TYPE: PRT
<213> ORGANISM: Artificial Sequence
<220> FEATURE:
<223> OTHER INFORMATION: VL DLX2468

<400> SEQUENCE: 127

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Gly Asn Tyr
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Ala Gly Gly Gly Thr Ser
                85                  90                  95

Ile Ala Phe Gly Gln Gly Thr Lys Leu Thr Val Leu Gly
            100                 105

<210> SEQ ID NO 128
<211> LENGTH: 119
<212> TYPE: PRT
<213> ORGANISM: Artificial Sequence
<220> FEATURE:
<223> OTHER INFORMATION: VH DLX2468

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ser
                20                  25                  30

Ala Met Ala Trp Val Arg Gln Ala Pro Gly Lys Gly Leu Glu Trp Val
            35                  40                  45

Gly Ile Ile Tyr Asp Ser Ala Ser Thr Tyr Tyr Ala Ser Trp Ala Lys
        50                  55                  60

Gly Arg Phe Thr Ile Ser Arg Asp Thr Ser Lys Asn Thr Val Tyr Leu
65                  70                  75                  80
```

-continued

Gln Met Asn Ser Leu Arg Ala Glu Asp Thr Ala Val Tyr Tyr Cys Ala
                85                  90                  95

Arg Glu Arg Asn Ile Phe Ser Gly Asp Met Val Leu Trp Gly Gln Gly
            100                 105                 110

Thr Leu Val Thr Val Ser Ser
        115

<210> SEQ ID NO 129
<211> LENGTH: 109
<212> TYPE: PRT
<213> ORGANISM: Artificial Sequence
<220> FEATURE:
<223> OTHER INFORMATION: VL DLX2475

<400> SEQUENCE: 129

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Lys Trp
            20                  25                  30

Leu Ser Trp Tyr Gln Gln Lys Pro Gly Lys Ala Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val His
                85                  90                  95

Ile Ala Phe Gly Gln Gly Thr Lys Leu Thr Val Leu Gly
            100                 105

<210> SEQ ID NO 130
<211> LENGTH: 119
<212> TYPE: PRT
<213> ORGANISM: Artificial Sequence
<220> FEATURE:
<223> OTHER INFORMATION: VH DLX2475

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Lys Leu Trp Gly Gln Gly
            100                 105                 110

Thr Leu Val Thr Val Ser Ser
        115

<210> SEQ ID NO 131
<211> LENGTH: 109
<212> TYPE: PRT
<213> ORGANISM: Artificial Sequence

<220> FEATURE:
<223> OTHER INFORMATION: VL DLX2476

<400> SEQUENCE: 131

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
            85                  90                  95

Ile Ala Phe Gly Gln Gly Thr Lys Leu Thr Val Leu Gly
            100                 105

<210> SEQ ID NO 132
<211> LENGTH: 119
<212> TYPE: PRT
<213> ORGANISM: Artificial Sequence
<220> FEATURE:
<223> OTHER INFORMATION: VH DLX2476

<400> SEQUENCE: 132

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Glu Arg Asp Ile Phe Ser Gly Asp Phe Val Gly Trp Gly Gln Gly
            100                 105                 110

Thr Leu Val Thr Val Ser Ser
        115

<210> SEQ ID NO 133
<211> LENGTH: 109
<212> TYPE: PRT
<213> ORGANISM: Artificial Sequence
<220> FEATURE:
<223> OTHER INFORMATION: VL DLX2480

<400> SEQUENCE: 133

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
                50                  55                  60

Ser Gly Ser Gly Ala Glu Phe Thr Leu Thr Ile Ser Ser Leu Gln Pro
 65                  70                  75                  80

Asp Asp Phe Ala Thr Tyr Tyr Cys Gln Asn Thr Gly Gly Ile Asn
                 85                  90                  95

Ile Ala Phe Gly Gln Gly Thr Lys Leu Thr Val Leu Gly
                100                 105

<210> SEQ ID NO 134
<211> LENGTH: 119
<212> TYPE: PRT
<213> ORGANISM: Artificial Sequence
<220> FEATURE:
<223> OTHER INFORMATION: VH DLX2480

<400> SEQUENCE: 134

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Ser Asp Ala
                20                  25                  30

Ala Met Ala Trp Val Arg Gln Ala Pro Gly Lys Gly Leu Glu Trp Val
             35                  40                  45

Gly Ile Ile Tyr Asp Ser Ala Ser Thr Tyr Tyr Ala Ser Trp Ala Lys
 50                  55                  60

Gly Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Arg Gln Ile Phe Ser Gly Asp Phe Val Leu Trp Gly Gln Gly
                100                 105                 110

Thr Leu Val Thr Val Ser Ser
        115

<210> SEQ ID NO 135
<211> LENGTH: 109
<212> TYPE: PRT
<213> ORGANISM: Artificial Sequence
<220> FEATURE:
<223> OTHER INFORMATION: VL DLX2543

<400> SEQUENCE: 135

Glu Ile Val Met Thr Gln Ser Pro Ser Thr Leu Ser Ala Ser Val Gly
 1               5                  10                  15

Asp Arg Val Thr Ile Thr Cys Gln Ala Ser Gln Ser Ile Ser Ser Trp
                20                  25                  30

Leu Ser Trp Tyr Gln Gln Lys Pro Gly Lys Ala Pro Lys Leu Leu Ile
             35                  40                  45

Tyr Lys Ala Ser Thr Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Asn Ala Gly Gly Val Ser
                 85                  90                  95

Ile Ala Phe Gly Gln Gly Thr Lys Leu Thr Val Leu Gly
                100                 105

<210> SEQ ID NO 136

```
<211> LENGTH: 109
<212> TYPE: PRT
<213> ORGANISM: Artificial Sequence
<220> FEATURE:
<223> OTHER INFORMATION: VL DLX2529

<400> SEQUENCE: 136

Glu Ile Val Met Thr Gln Ser Pro Ser Thr Leu Ser Ala Ser Val Gly
1               5                   10                  15

Asp Arg Val Ile Ile Thr Cys Arg Ala Ser Gln Ser Ile Gly Asn Trp
            20                  25                  30

Leu Ser Trp Tyr Gln Gln Lys Pro Gly Lys Ala Pro Lys Leu Leu Ile
        35                  40                  45

Tyr Arg Ala Ser Asn Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Glu Asp Phe Ala Thr Tyr Tyr Cys Gln Asn Thr Gly Gly Gly Ile Asn
                85                  90                  95

Ile Ala Phe Gly Gln Gly Thr Lys Leu Thr Val Leu Gly
            100                 105

<210> SEQ ID NO 137
<211> LENGTH: 110
<212> TYPE: PRT
<213> ORGANISM: Artificial Sequence
<220> FEATURE:
<223> OTHER INFORMATION: VL DLX2547

<400> SEQUENCE: 137

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
            20                  25                  30

Tyr Leu Ser Trp Tyr Gln Gln Lys Pro Gly Lys Ala Pro Lys Leu Leu
        35                  40                  45

Ile Tyr Arg Ala Ser Thr Leu Ala Ser Gly Val Pro Ser Arg Phe Ser
    50                  55                  60

Gly Ser Gly Ser Gly Ala Glu Phe Thr Leu Thr Ile Ser Ser Leu Gln
65                  70                  75                  80

Pro Asp Asp Phe Ala Thr Tyr Tyr Cys Gln Asn Thr Gly Gly Gly Ile
                85                  90                  95

Asn Ile Ala Phe Gly Gln Gly Thr Lys Leu Glu Ile Lys Arg
            100                 105                 110

<210> SEQ ID NO 138
<211> LENGTH: 119
<212> TYPE: PRT
<213> ORGANISM: Artificial Sequence
<220> FEATURE:
<223> OTHER INFORMATION: VH DLX2547

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Val
        35                  40                  45
```

```
Gly Ile Ile Tyr Asp Ser Ala Ser Thr Tyr Tyr Ala Ser Trp Ala Lys
     50                  55                  60

Gly Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Arg Ala Ile Phe Ser Gly Asp Phe Val Leu Trp Gly Gln Gly
             100                 105                 110

Thr Leu Val Thr Val Ser Ser
        115
```

<210> SEQ ID NO 139
<211> LENGTH: 109
<212> TYPE: PRT
<213> ORGANISM: Artificial Sequence
<220> FEATURE:
<223> OTHER INFORMATION: VL DLX2528

<400> SEQUENCE: 139

```
Glu Ile Val Met Thr Gln Ser Pro Ser Thr Leu Ser Ala Ser Val Gly
 1               5                  10                  15

Asp Arg Val Thr Ile Thr Cys Gln Ala Ser Gln Ser Ile Gly Asn Trp
             20                  25                  30

Leu Ala Trp Tyr Gln Gln Lys Pro Gly Lys Ala Pro Lys Leu Leu Ile
         35                  40                  45

Tyr Gln Ala Ser Asn Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Asn Ala Gly Gly Ala Thr Thr
                 85                  90                  95

Ile Ala Phe Gly Gln Gly Thr Lys Leu Thr Val Leu Gly
             100                 105
```

<210> SEQ ID NO 140
<211> LENGTH: 119
<212> TYPE: PRT
<213> ORGANISM: Artificial Sequence
<220> FEATURE:
<223> OTHER INFORMATION: VH DLX2528

<400> SEQUENCE: 140

```
Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Ser Leu Ser Ser Ala
             20                  25                  30

Ala Met Ala Trp Val Arg Gln Ala Pro Gly Lys Gly Leu Glu Trp Val
         35                  40                  45

Gly Ile Ile Tyr Asp Ser Ala Ser Thr Tyr Tyr Ala Ser Trp Ala Lys
     50                  55                  60

Gly Arg Phe Thr Ile Ser Arg Asp Thr Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Glu Arg Ala Ile Phe Ser Gly Asp Phe Val Leu Trp Gly Gln Gly
             100                 105                 110

Thr Leu Val Thr Val Ser Ser
        115
```

<210> SEQ ID NO 141
<211> LENGTH: 109
<212> TYPE: PRT
<213> ORGANISM: Artificial Sequence
<220> FEATURE:
<223> OTHER INFORMATION: VL DLX2585

<400> SEQUENCE: 141

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly
            100                 105
```

<210> SEQ ID NO 142
<211> LENGTH: 119
<212> TYPE: PRT
<213> ORGANISM: Artificial Sequence
<220> FEATURE:
<223> OTHER INFORMATION: VH DLX2585

<400> SEQUENCE: 142

```
Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Tyr
            20                  25                  30

Ala Met Ser Trp Val Arg Gln Ala Pro Gly Lys Gly Leu Glu Trp Val
        35                  40                  45

Gly Ile Ile Tyr Asp Ser Ala Ser Thr Tyr Tyr Ala Ser Trp Ala Lys
50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Glu Arg Ala Ile Phe Ser Gly Asp Phe Asp Tyr Trp Gly Gln Gly
            100                 105                 110

Thr Leu Val Thr Val Ser Ser
        115
```

<210> SEQ ID NO 143
<211> LENGTH: 109
<212> TYPE: PRT
<213> ORGANISM: Artificial Sequence
<220> FEATURE:
<223> OTHER INFORMATION: VL DLX2545

<400> SEQUENCE: 143

```
Glu Ile Val Met Thr Gln Ser Pro Ser Thr Leu Ser Ala Ser Val Gly
1               5                   10                  15
```

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly
            100                 105

<210> SEQ ID NO 144
<211> LENGTH: 119
<212> TYPE: PRT
<213> ORGANISM: Artificial Sequence
<220> FEATURE:
<223> OTHER INFORMATION: VH DLX2545

<400> SEQUENCE: 144

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Ala
            20                  25                  30

Ala Met Ala Trp Val Arg Gln Ala Pro Gly Lys Gly Leu Glu Trp Ile
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Arg Asp Thr Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Glu Arg Asn Ile Phe Ser Gly Asp Met Val Leu Trp Gly Gln Gly
            100                 105                 110

Thr Thr Val Thr Val Ser Ser
        115

<210> SEQ ID NO 145
<211> LENGTH: 109
<212> TYPE: PRT
<213> ORGANISM: Artificial Sequence
<220> FEATURE:
<223> OTHER INFORMATION: VL DLX2531

<400> SEQUENCE: 145

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

```
Ile Ala Phe Gly Gln Gly Thr Lys Leu Thr Val Leu Gly
            100                 105
```

<210> SEQ ID NO 146
<211> LENGTH: 119
<212> TYPE: PRT
<213> ORGANISM: Artificial Sequence
<220> FEATURE:
<223> OTHER INFORMATION: VH DLX2531

<400> SEQUENCE: 146

```
Glu Val Gln Leu Val Glu Ser Gly Gly Asn Val Gln Pro Gly Gly
1               5                   10                  15

Ser Leu Arg Leu Ser Cys Thr Ala Ser Gly Phe Ser Leu Ser Asn Ser
            20                  25                  30

Ala Met Ala Trp Val Arg Gln Ala Pro Gly Lys Gly Leu Glu Trp Val
            35                  40                  45

Gly Ile Ile Tyr Asp Ser Ala Ser Thr Tyr Tyr Ala Ser Trp Ala Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Tyr Cys Ala
                85                  90                  95

Arg Glu Arg Ala Ile Phe Ser Gly Asp Phe Ala Leu Trp Gly Gln Gly
            100                 105                 110

Thr Leu Val Thr Val Ser Ser
            115
```

<210> SEQ ID NO 147
<211> LENGTH: 109
<212> TYPE: PRT
<213> ORGANISM: Artificial Sequence
<220> FEATURE:
<223> OTHER INFORMATION: VL DLX2586

<400> SEQUENCE: 147

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly
            100                 105
```

<210> SEQ ID NO 148
<211> LENGTH: 119
<212> TYPE: PRT
<213> ORGANISM: Artificial Sequence
<220> FEATURE:
<223> OTHER INFORMATION: VH DLX2586

<400> SEQUENCE: 148

```
Glu Val Gln Leu Val Glu Ser Gly Gly Leu Val Gln Pro Gly Gly
1               5                   10                  15

Ser Leu Arg Leu Ser Cys Thr Val Ser Gly Phe Ser Leu Ser Tyr
            20                  25                  30

Ala Met Ser Trp Val Arg Gln Ala Pro Gly Lys Gly Leu Glu Trp Ile
        35                  40                  45

Gly Ile Ile Tyr Asp Ser Ala Ser Thr Tyr Tyr Ala Ser Trp Ala Lys
50                      55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Glu Arg Gln Ile Phe Ser Gly Asp Met Asp Gly Trp Gly Gln Gly
                100                 105                 110

Thr Leu Val Thr Val Ser Ser
            115
```

<210> SEQ ID NO 149
<211> LENGTH: 109
<212> TYPE: PRT
<213> ORGANISM: Artificial Sequence
<220> FEATURE:
<223> OTHER INFORMATION: VL DLX2530

<400> SEQUENCE: 149

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Gly Val Ser
                85                  90                  95

Ile Ala Phe Gly Gln Gly Thr Lys Leu Thr Val Leu Gly
            100                 105
```

<210> SEQ ID NO 150
<211> LENGTH: 119
<212> TYPE: PRT
<213> ORGANISM: Artificial Sequence
<220> FEATURE:
<223> OTHER INFORMATION: VH DLX2530

<400> SEQUENCE: 150

```
Glu Val Gln Leu Val Glu Ser Gly Gly Asn Val Gln Pro Gly Gly
1               5                   10                  15

Ser Leu Arg Leu Ser Cys Thr Ala Ser Gly Phe Ser Leu Ser Asp Ala
            20                  25                  30

Ala Met Ala Trp Val Arg Gln Ala Pro Gly Lys Gly Leu Glu Trp Val
        35                  40                  45

Gly Ile Ile Tyr Asp Ser Ala Ser Thr Phe Tyr Ala Ser Trp Ala Lys
50                      55                  60

Gly Arg Phe Thr Ile Ser Arg Asp Asn Ser Lys Asn Thr Leu Tyr Leu
65                  70                  75                  80
```

Gln Met Asn Ser Leu Arg Ala Glu Asp Thr Ala Thr Tyr Tyr Cys Ala
                85                  90                  95

Arg Glu Arg Asn Ile Phe Ser Gly Asp Met Ala Leu Trp Gly Gln Gly
            100                 105                 110

Thr Thr Val Thr Val Ser Ser
        115

<210> SEQ ID NO 151
<211> LENGTH: 109
<212> TYPE: PRT
<213> ORGANISM: Artificial Sequence
<220> FEATURE:
<223> OTHER INFORMATION: VL DLX2548

<400> SEQUENCE: 151

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Asp Asn Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Thr Gly Gly Val Ser
                85                  90                  95

Ile Ala Phe Gly Gln Gly Thr Lys Leu Thr Val Leu Gly
            100                 105

<210> SEQ ID NO 152
<211> LENGTH: 119
<212> TYPE: PRT
<213> ORGANISM: Artificial Sequence
<220> FEATURE:
<223> OTHER INFORMATION: VH DLX2548

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Tyr
            20                  25                  30

Ala Met Ser Trp Val Arg Gln Ala Pro Gly Lys Gly Leu Glu Trp Ile
        35                  40                  45

Gly Ile Ile Tyr Asp Ser Ala Ser Thr Tyr Tyr Ala Ser Trp Ala Lys
    50                  55                  60

Gly Arg Phe Thr Ile Ser Lys Asp Thr Ser Lys Asn Thr Leu Tyr Leu
65                  70                  75                  80

Gln Met Asn Ser Leu Arg Ala Glu Asp Thr Ala Val Tyr Phe Cys Ala
                85                  90                  95

Arg Glu Arg Gln Ile Phe Ser Gly Asp Met Asp Gly Trp Gly Gln Gly
            100                 105                 110

Thr Thr Val Thr Val Ser Ser
        115

<210> SEQ ID NO 153
<211> LENGTH: 110
<212> TYPE: PRT

```
<213> ORGANISM: Artificial Sequence
<220> FEATURE:
<223> OTHER INFORMATION: VL DLX2544

<400> SEQUENCE: 153

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Lys Ala Ser Thr Leu Ala Ser Gly Val Pro Ser Arg Phe Ser
50                      55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Asn Ala Gly Gly Gly Ile
                    85                  90                  95

Asn Ile Ala Phe Gly Gln Gly Thr Lys Val Glu Ile Lys Arg
                100                 105                 110

<210> SEQ ID NO 154
<211> LENGTH: 249
<212> TYPE: PRT
<213> ORGANISM: Artificial Sequence
<220> FEATURE:
<223> OTHER INFORMATION: DLX2544

<400> SEQUENCE: 154

Ala Asp Ile Val Met Thr Gln Ser Pro Ser Thr Leu Ser Ala Ser Val
1               5                   10                  15

Gly Asp Arg Val Thr Ile Thr Cys Gln Ala Ser Gln Ser Ile Ser Ser
                20                  25                  30

Tyr Leu Ser Trp Tyr Gln Gln Lys Pro Gly Lys Ala Pro Lys Leu Leu
            35                  40                  45

Ile Tyr Lys Ala Ser Thr Leu Ala Ser Gly Val Pro Ser Arg Phe Ser
50                      55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Asn Ala Gly Gly Gly Ile
                    85                  90                  95

Asn Ile Ala Phe Gly Gln Gly Thr Lys Val Glu Ile Lys Arg Gly Gly
                100                 105                 110

Gly Ser Gly Gly Gly Gly Ser Gly Gly Gly Ser Gly Gly
            115                 120                 125

Gly Ser Glu Val Gln Leu Val Glu Ser Gly Gly Leu Val Gln Pro
130                 135                 140

Gly Gly Ser Leu Arg Leu Ser Cys Thr Ala Ser Gly Phe Ser Leu Ser
145                 150                 155                 160

Ser Ala Ala Met Ala Trp Val Arg Gln Ala Pro Gly Lys Gly Leu Glu
                165                 170                 175

Trp Val Gly Ile Ile Tyr Asp Ser Ala Ser Thr Tyr Tyr Ala Ser Trp
            180                 185                 190

Ala Lys Gly Arg Phe Thr Ile Ser Arg Asp Thr Ser Lys Asn Thr Val
        195                 200                 205

Tyr Leu Gln Met Asn Ser Leu Arg Ala Glu Asp Thr Ala Val Tyr Tyr
    210                 215                 220
```

Cys Ala Arg Glu Arg Ala Ile Phe Ser Gly Asp Phe Val Leu Trp Gly
225                 230                 235                 240

Gln Gly Thr Leu Val Thr Val Ser Ser
                245

<210> SEQ ID NO 155
<211> LENGTH: 9
<212> TYPE: PRT
<213> ORGANISM: Artificial Sequence
<220> FEATURE:
<223> OTHER INFORMATION: CDR-H1 of DLX2531

<400> SEQUENCE: 155

Phe Ser Leu Ser Asn Ser Ala Met Ala
1               5

<210> SEQ ID NO 156
<211> LENGTH: 16
<212> TYPE: PRT
<213> ORGANISM: Artificial Sequence
<220> FEATURE:
<223> OTHER INFORMATION: CDR-H2 of DLX2531

<400> SEQUENCE: 156

Ile Ile Tyr Asp Ser Ala Ser Thr Tyr Tyr Ala Ser Trp Ala Lys Gly
1               5                   10                  15

<210> SEQ ID NO 157
<211> LENGTH: 11
<212> TYPE: PRT
<213> ORGANISM: Artificial Sequence
<220> FEATURE:
<223> OTHER INFORMATION: CDR-H3 of DLX2531

<400> SEQUENCE: 157

Glu Arg Ala Ile Phe Ser Gly Asp Phe Ala Leu
1               5                   10

<210> SEQ ID NO 158
<211> LENGTH: 11
<212> TYPE: PRT
<213> ORGANISM: Artificial Sequence
<220> FEATURE:
<223> OTHER INFORMATION: CDR-L1 of DLX2531

<400> SEQUENCE: 158

Gln Ala Ser Gln Ser Ile Asp Asn Trp Leu Ser
1               5                   10

<210> SEQ ID NO 159
<211> LENGTH: 7
<212> TYPE: PRT
<213> ORGANISM: Artificial Sequence
<220> FEATURE:
<223> OTHER INFORMATION: CDR-L2 of DLX2531

<400> SEQUENCE: 159

Arg Ala Ser Thr Leu Ala Ser
1               5

<210> SEQ ID NO 160
<211> LENGTH: 10
<212> TYPE: PRT
<213> ORGANISM: Artificial Sequence
<220> FEATURE:
<223> OTHER INFORMATION: CDR-L3 of DLX2531

```
<400> SEQUENCE: 160

Gln Asn Thr Gly Gly Gly Val Ser Ile Ala
1               5                   10

<210> SEQ ID NO 161
<211> LENGTH: 11
<212> TYPE: PRT
<213> ORGANISM: Artificial Sequence
<220> FEATURE:
<223> OTHER INFORMATION: CDR-L1 of DLX2681

<400> SEQUENCE: 161

Arg Ala Ser Gln Ser Ile Gly Asn Trp Leu Ser
1               5                   10

<210> SEQ ID NO 162
<211> LENGTH: 7
<212> TYPE: PRT
<213> ORGANISM: Artificial Sequence
<220> FEATURE:
<223> OTHER INFORMATION: CDR-L2 of DLX2681

<400> SEQUENCE: 162

Arg Ala Ser Asn Leu Ala Ser
1               5

<210> SEQ ID NO 163
<211> LENGTH: 10
<212> TYPE: PRT
<213> ORGANISM: Artificial Sequence
<220> FEATURE:
<223> OTHER INFORMATION: CDR-L3 of DLX2681

<400> SEQUENCE: 163

Gln Asn Thr Gly Gly Gly Ile Asn Ile Ala
1               5                   10
```

METHOD OF INHIBITING HUMAN IL-1 BETA BY ADMINISTERING AN ANTIBODY TO HUMAN IL-1 BETA

RELATED APPLICATIONS

This application is a divisional of application Ser. No. 14/072,165, filed on Nov. 5, 2013, which claims the benefit t of U.S. Provisional Application No. 61/722,532, filed on Nov. 5, 2012. This application claims priority under 35 U.S.C. § 119 or 365 to EP Application No. 12007503.1, filed Nov. 5, 2012. The entire teachings of the above applications are incorporated herein by reference.

DESCRIPTION

The invention relates to humanized anti-IL-1 beta antibodies, in particular monovalent, highly potent anti-IL-1 beta antibody fragments. The invention also relates to nucleic acids encoding such antibodies, vectors, host cells containing such sequences, pharmaceutical and diagnostic compositions comprising the antibodies or nucleic acids, and uses thereof.

BACKGROUND OF THE INVENTION

Interleukin-1 beta (IL-1 beta) is a pro-inflammatory cytokine which is produced as a precursor by activated macrophages. Upon proteolytic cleavage, signal transduction is initiated by binding of the active form to the IL-1 receptor type I (IL-1R1) which in turn associates with the transmembrane IL-1 receptor accessory protein (IL-1RAP). The formed complex is competent of signal transduction. Being a key mediator in the inflammatory response, the cytokine affects a number of cellular activities such as cell proliferation, differentiation, and apoptosis. Therefore, IL-1 beta has been considered an important target for a variety of pharmaceuticals.

There is a need in the art for antibodies with high therapeutic potential against human IL-1 beta. For being therapeutically successful, it is important that such antibody displays desirable biophysical and biochemical characteristics. For example, since the target IL-1 beta is a highly efficient interleukin that is potent at very low concentrations and thus needs to be comprehensively blocked, such antibody needs to be highly potent as well as highly stable and soluble.

SUMMARY OF THE INVENTION

In a first aspect, the invention provides a monovalent antibody fragment directed against IL-1 beta having a potency of lower than 50 picomolar (pM), as determined by the half-maximum inhibitory concentration $IC_{50}$ with regard to inhibiting the biological effect of human IL-1 beta.

Monovalent antibody fragments, whether being humanized or not, having potency values in the pM-range are particular and not routinely obtained. In addition and typically, an antibody loses affinity to its target upon humanization when compared to the parent non-human antibody. It is therefore a challenge to humanize an antibody such that the affinity parameters are close or equal to the parent antibody. This is particularly true for monovalent antibody fragments which comprise only one variable light and heavy chain, and therefore bind to the target less strongly than bivalent antibodies displaying two light and heavy chains.

Moreover, when converting a full-length antibody into a smaller fragment, its potency usually becomes diminished. This is not only due to the accompanying change of valency (for example, the antibody fragment might only be monovalent whereas a full-length immunoglobulin is bi- or multivalent) but may also be caused by steric reasons.

A potent antibody is particularly useful since it allows administering lower amounts of drug to the patient, thereby decreasing the overall costs of treatment. In addition, a more complete neutralization of the molecular target of the disease is rendered feasible.

Moreover, different application routes in animal models as well as in human therapy can be envisioned when applying highest potency antibodies. For example, as to topical drugs, although delivery may be limited due to the barrier function of the epithelial layer, efficacy of treatment is restored by the high potency of the limited quantity of drug molecules that passes this physiological barrier.

Often, the high amount of a less potent drug, which needs to be administered to achieve similar pharmacodynamic effects, translates into much higher intravenous or subcutaneous application volumes than with a more potent drug. Such higher application volumes are a disadvantage for use in animals and humans for two reasons; firstly, the impracticality of treating patients with a high volume of drug, and secondly, because antibodies are very expensive per unit of mass.

Therefore, lower quantities of antibody used for treatment translate into lower production costs of the drug. In particular, antibody fragments are suitable for production using, e.g., bacterial or yeast culture systems, which are of comparatively lower cost than mammalian expression systems typically used for the production of full-length immunoglobulins such as IgG. The combination of smaller quantities of drug to be administered and cheaper manufacturing processes opens the possibility of more cost-efficient medicines per patient. Thus, a larger number of patients may benefit from such drug.

Stability and solubility parameters are other factors crucial for providing a viable medicament. The more stable and soluble an antibody drug, the smaller the volume of administration and the longer the shelf half-life time. The antibodies provided herein are highly stable and soluble, i.e., they remain monomeric for prolonged periods of time and also at high concentrations.

In one aspect, an antibody is provided, in particular the monovalent antibody fragment above, comprising:
(a) at least one of the variable heavy chain (VH) complementarity determining region (CDR) sequences CDR-H1, CDR-H2 or CDR-H3 as set forth in SEQ ID Nos.: 1, 2 and 3, respectively, or variants thereof; and/or
(b) at least one of the variable light chain (VL) CDR sequences CDR-L1, CDR-L2 or CDR-L3 as set forth in SEQ ID Nos.: 4, 5, and 6, respectively, or variants thereof.

In another embodiment, the antibody, and in particular said monovalent antibody fragment, comprises:
(a) at least one of the variable heavy chain (VH) complementarity determining region (CDR) sequences CDR-H1, CDR-H2 or CDR-H3 as set forth in SEQ ID Nos.: 155, 156 and 157, respectively, or variants thereof; and/or
(b) at least one of the variable light chain (VL) CDR sequences CDR-L1, CDR-L2 or CDR-L3
  (i) as set forth in SEQ ID Nos.: 158, 159 and 160, respectively, or variants thereof, or
  (ii) as set forth in SEQ ID Nos.: 161, 162 and 163, respectively, or variants thereof.

In some embodiments, the antibody comprises:

(a) a VH having at least 85% identity to a sequence selected from the group consisting of SEQ ID No.: 7 and SEQ ID No.: 146; and/or (b) a VL having at least 85% identity to a sequence selected from the group consisting of SEQ ID No.: 8, SEQ ID No.: 136 and SEQ ID No.: 145.

The antibody can comprise a linker sequence, being or derived from SEQ ID No.: 9. In some embodiments, such antibody is an antibody fragment having at least 85% sequence identity to a sequence selected from the group consisting of SEQ ID No.: 10, SEQ ID No.: 73 and SEQ ID No.: 82.

In one aspect the invention provides binding members that bind to IL-1 beta and compete for binding with the antibodies described herein. Said binding member can be monovalent or multivalent. A preferred multivalent binding member is bivalent. A multivalent binding member can be bispecific.

In one aspect, the invention provides an isolated nucleic acid sequence encoding the antibody or the binding member disclosed herein.

In one aspect, a vector comprising said nucleic acid sequence is provided.

In one aspect, the invention provides a host cell comprising the nucleic acid sequence above or the vector above.

In one aspect, a composition comprising the antibody above, the binding member above, the nucleic acid sequence above, the vector above or the host cell above; and further a suitable carrier, diluent or excipient. The composition is preferably a pharmaceutical composition, comprising a pharmaceutically acceptable carrier, diluent or excipient. Such pharmaceutical composition is preferably in a form suitable for topical, intradermal, transdermal, intravenous, subcutaneous, intramuscular, parenteral, sublingual, buccal, oral, nasal, intranasal, rectal, local or ocular administration.

Further provided is a method of treating an IL-1 beta-mediated disease comprising administering to a subject in need thereof the pharmaceutical composition above.

Also provided is the antibody above, the binding member above, the nucleic acid sequence above, the vector above or the host cell disclosed herein:

(i) for use in the treatment of an IL-1 beta-mediated disease;

(ii) for use in diagnostics;

(iii) for use in cosmetics; and/or (iv) for detection purposes.

In still another aspect, the invention provides a method of producing the antibody or the binding member described herein, either comprising: (i) the steps of cultivating the host cell above and recovering and purifying the antibody fragment or the binding member, respectively; or (ii) the use of a cell-free system. Additionally or alternatively, the method can comprise at least one step of chemical protein synthesis.

BRIEF DESCRIPTION OF DRAWINGS

FIG. 6 illustrates the results of an ELISA assay wherein cleared cell lysates of DLX2323 variants expressed in *E. coli* cells bind bound to coated rhIL-1 beta.

DETAILED DESCRIPTION

Figure 1:
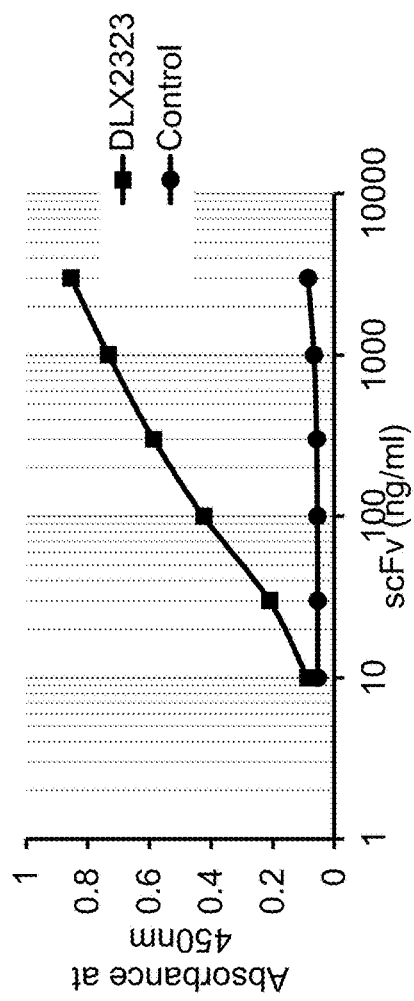
FIG. 1 shows the results of an ELISA to determine binding of DLX2323 to recombinant human (rh) IL-1 beta at various concentrations.

So that the invention may be more readily understood, certain terms are first defined. Unless otherwise defined within the specification, all technical and scientific terms used herein have their art-recognized meaning. Although similar or equivalent methods and materials to those described herein can be used in the practice or testing of the invention, suitable methods and materials are described below. All publications, patent applications, patents, and other references mentioned herein are incorporated by reference in their entirety. In case of conflict, the present specification, including definitions, will prevail. The materials, methods, and examples are illustrative only and not intended to be limiting.

Within the scope of the present invention, the term "antibody" refers to full-length immunoglobulins as well as to fragments thereof. Such full-length immunoglobulins may be monoclonal, polyclonal, chimeric, humanized, veneered or human antibodies.

"Antibody fragments" comprise portions of a full-length immunoglobulin retaining the targeting specificity of said immunoglobulin. Many but not all antibody fragments lack at least partially the constant region (Fe region) of the full-length immunoglobulin. In some embodiments, antibody fragments are produced by digestion of the full-length immunoglobulin. An antibody fragment may also be a synthetic or recombinant construct comprising parts of the immunoglobulin or immunoglobulin chains (see e.g. HOLLIGER. P. and Hudson, J. Engineered antibody fragments and the rise of single domains. *Nature Biotechnology* 2005, vol. 23, no. 9, p. 1126-1136). Examples of antibody fragments, without being limited to, include scFv, Fab, Fv, Fab', F(ab')$_2$ fragments, dAb, VHH, nanobodies, V(NAR) or minimal recognition units.

"Single chain variable fragments" or "single chain antibodies" or "scFv" are one type of antibody fragments. scFv are fusion proteins comprising the VH and VL of immunoglobulins connected by a linker. They thus lack the constant Fc region present in full-length immunoglobulins, but retain the specificity of the original immunoglobulin.

A "binding member" as used herein refers to full-length immunoglobulins, antibody fragments, non-antibody scaffolds, and/or other binding compounds. Such binding member can be monovalent or multivalent, i.e. having one or more antigen binding sites. Non-limiting examples of monovalent binding members include scFv, Fab fragments, dAb, VHH, DARPins, affilins and nanobodies. A multivalent binding member can have two, three, four or more antigen binding sites whereby one or more different antigens can be recognized. Full-length immunoglobulins, F(ab')$_2$ fragments, bis-scFv and diabodies are non-limiting examples of multivalent binding members; in said exemplary multivalent binding members, two binding sites are present, i.e. the binding member is bivalent.

In one embodiment, the multivalent binding member is bispecific, i.e. the binding member is directed against two different targets or two different target sites on one target molecule. Bispecific antibodies are, e.g., reviewed in MÜLLER, D. and Kontermann, R. E. Bispecific antibodies. Edited by DÜBEL, S. Weinheim: Wiley-VCH, 2007. ISBN 3527314539. p. 345-378. In another embodiment, the multivalent binding member comprises more than two, e.g., three Or four different binding sites for three or four, respectively, different antigens. Such binding member is multivalent and multispecific in particular tri- or tetra-specific, respectively.

"Non-antibody scaffolds" are antigen-binding polypeptides which are e.g. described in FIELDER, M. and Skerra, A. Non-antibody scaffolds. Edited by DÜBEL, S. Weinheim: Wiley-VCH, 2007. ISBN 3527314539. p. 467-500; or GILBRETH, R. N. and Koide, S. Structural insights for engineering binding proteins based on nonantibody scaffolds. *Current Opinion in Structural Biology* 2012, vol. 22, p. 413-420. Non-limiting examples include affibodies, affilin molecules, AdNectin, Anticalin, DARPins, Knottin, Kunitz-type domain, Avimer, Tetranectin and trans-body.

"Binding compounds" are chemical or biological molecules that bind to a target and that are not belonging to the class of full-length immunoglobulins, antibody fragments and non-antibody scaffolds as defined above. Examples of binding compounds, without being limited to, include macrolides (GUNDLURU, M. K. et al. Design, synthesis and initial biological evaluation of a novel pladienolide analog scaffold. *Medchemcomm.* 2011, vol. 2, p. 904-908; PATERSON, L. et al. Total synthesis and biological evaluation of a series of macrocyclic hybrids and analogies of the antimitotic natural products dictyostatin, discodermolide and taxol. *Chem Asian J.* 2011, vol. 6, p. 459-473; MORITA, H. et al. Synthesis of unnatural alkaloid scaffolds by exploiting plant polyketide synthase. *PNAS* 2011, vol. 108, p. 13504-13509), molecular imprinted polymers (HOSHINO, Y. et al. Recognition, neutralization and clearance of target peptides in the blood stream of living mice by molecular imprinted polymer nanoparticles: a plastic antibody. *Journal of the American Chemical Society,* 2010, vol. 19, p. 664-6645), aptamers (STREHLITZ, B., et al. Aptamers for pharmaceuticals and their application in environmental analytics. *Bioanalytical reviews* 2012, vol. 4, p. 1-30; YE, M. et al. Generating Aptamers by Cell-SELEX for Applications in Molecular Medicine. *International Journal of Molecular Sciences* 2012, vol. 13, p. 3341-3353), Spiegelmers (see e.g., MAASCH, C. et al. Polyethylenimine-Polyplexes of Spiegelmer NOX-A50 directed against intracellular high mobility group protein A1 (HMGA1) reduce tumor growth in vivo. *JBC* 2010, vol. 285, p. 40012-40018), or peptides (cyclic or linear; see, e.g., GOULD, A. et al. Cyclotides, a novel ultrastable polypeptide scaffold for drug discovery. *Curr Pharm Des.* 2011, vol. 17, p. 4294-4307).

The "$IC_{50}$" or "half-maximum inhibitory concentration" is a measure of antagonist drug potency and describes quantitatively the effectiveness of a compound to inhibit a biological or biochemical function. This measure indicates how much of the compound is needed to inhibit by 50% a certain biological or biochemical process. Although no direct indicator of affinity, both values are correlated and can be determined via the Cheng-Prusoff equation (CHENG Y. and Prusoff W. H. Relationship between the inhibition constant (Ki) and the concentration of inhibitor which causes 50 percent inhibition (I50) of an enzymatic reaction. *Biochemical Pharmacology* 1973, vol. 22, p. 3099-3108; RAMMES, G., et al. Identification of a domain which affects kinetics and antagonistic potency of clozapine at 5-HT3 receptors. *PLOS one* 2009, vol. 4, p. 1-14; ZHEN, J., et al. Concentration of receptor and ligand revisited in a modified receptor binding protocol for high-affinity radioligands: [$^3$H] spiperone binding to $D_2$ and $D_3$ dopamine receptors. *Journal of Neuroscience Methods* 2010, vol. 188, p. 32-38).

The term "IL-1 beta specific binding" as used herein describes that a binding member binds to IL-1 beta with higher affinity than to a structurally different antigen which does not comprise the IL-1 beta epitope to which the anti-IL-1 beta binding member binds. Specific binding is reflected by a dissociation equilibrium constant ($K_D$) of lower than 1 micromolar. This constant can be determined, e.g. using Quartz Crystal Microbalance (QCM) in an Attana instrument, or Surface Plasmon Resonance (SPR) technology in a BIACORE instrument.

As used herein, "IL-1 beta" refers to the molecule as described in, e.g., Dinarello C. A., Treating inflammation by blocking interleukin-1 in a broad spectrum of diseases. *Nature reviews* 2012, vol. 11, p. 633-652. "hIL-1 beta" as used herein refers to human IL-1 beta. "rIL-1 beta" refers to recombinant IL-1 beta. Recombinant IL-1 beta may or may not have an amino terminal methionine residue, depending upon the method by which it is prepared. "rhIL-1" beta refers to recombinant human IL-1 beta. rhIL-1 beta may, e.g., be obtained from Peprotech, USA, cat. no. 200-01B. IL-1 beta may also be obtained by isolation from biological samples of human or non-human origin.

"Humanized" antibodies refer to antibodies comprising one or more, typically all six CDR regions of a non-human parent antibody or variants thereof, and of which the framework is, e.g., (i) a human framework, potentially comprising one or more framework residues of the non-human parent antibody, or (ii) a framework from a non-human antibody modified to increase similarity to naturally produced human frameworks. Methods of humanizing antibodies are known in the art, see e.g. LEGER, O. and Saldanha, J. Antibody Drug Discovery. Edited by WOOD, C. London: Imperial College Press, 2011. ISBN 1848166281. p. 1-23.

"Framework" (FR) refers to the scaffold of the variable immunoglobulin domain, either the variable light chain (VL) or variable heavy chain (VH), embedding the respective CDRs. A VL and/or VH framework typically comprises four framework sections, FR1, FR2, FR3 and FR4, flanking the CDR regions. Thus, as known in the art, a VL has the general structure: (FR-L1)-(CDR-L1)-(FR-L2)-(CDR-L2)-(FR-L3)-(CDR-L3)-(FR-L4), whereas a VH has the general structure: (FR-H1)-(CDR-H1)-(FR-H2)-(CDR-H2)-(FR-H3)-(CDR-H3)-(FR-H4).

Figure 5:
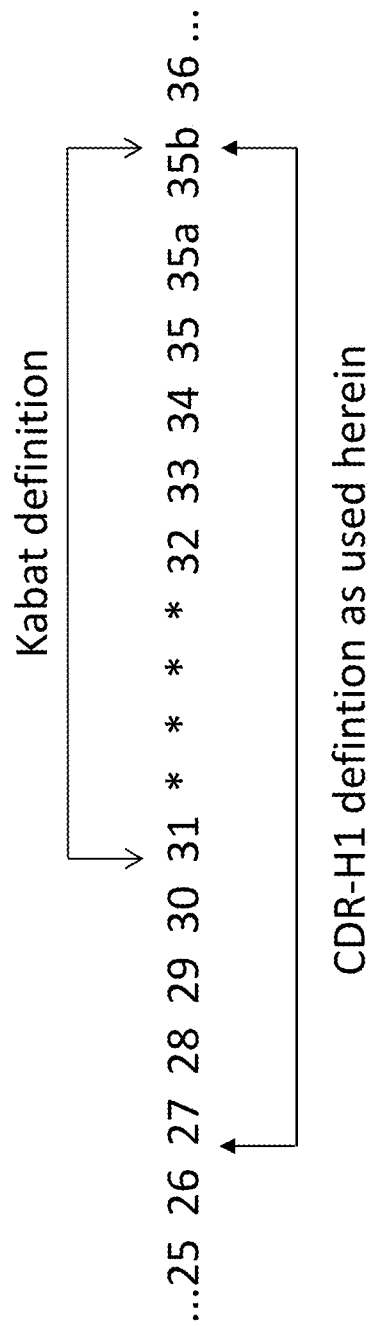
FIG. 5 illustrates the definition of CDR-H1 as used herein.

"CDR" refers to the hypervariable regions of the antibody which mainly contribute to antigen binding. Typically, an antigen binding site comprises six CDRs, embedded into a framework scaffold. Herein, the CDRs of the VL are referred to as CDR-L1, CDR-L2 and CDR-L3 whereas the CDRs of the VH are referred to as CDR-H1, CDR-H2 and CDR-H3. These can be identified as described in KABAT, E. A., et al. Sequences of Proteins of Immunological Interest. 5th edition. Edited by U.S. DEPARTMENT OF HEALTH AND HUMAN SERVICES. NIH Publications, 1991, p. 91-3242. CDR-H1 as used herein, however, differs from the Kabat definition in that it starts with position 27 and ends prior to position 36 (see FIG. 5 for illustration).

As used herein, the numbering system to identify amino acid residue positions in the VH and VL of the antibody corresponds to the "AHo"-system described by HONEGGER, A. and Plückthun, A. Yet another numbering scheme for immunoglobulin variable domains: An automatic modelling and analysis tool. *Journal of Molecular Biology* 2001, vol. 309, p. 657-670. The publication further provides conversion tables between the AHo and the Kabat system (KABAT, E. A., et al. Sequences of Proteins of Immunological Interest. 5th edition. Edited by U.S. DEPARTMENT OF HEALTH AND HUMAN SERVICES. NIH Publications, 1991. p. 91-3242).

An "isolated" antibody or nucleic acid is one being identified and separated and/or recovered from at least one component of its natural environment.

The term "identity" as used herein refers to the sequence match between two proteins or nucleic acids. The protein or nucleic acid sequences to be compared are aligned to give maximum identity, for example using bioinformatics tools such as EMBOSS Needle (pair wise alignment). When the same position in the sequences to be compared is occupied by the same nucleobase or amino acid residue, then the respective molecules are identical at that very position. Accordingly, the "percent identity" is a function of the number of matching positions divided by the number of positions compared and multiplied by 100%. For instance, if 6 out of sequence positions are identical, then the identity is 60%. The percent identity between two protein sequences can, e.g., be determined using the Needleman and Wunsch algorithm (NEEDILEMAN, S. B. and Wunsch, C. D. A general method applicable to the search for similarities in the amino acid sequence of two proteins. *Journal of Molecular Biology* 1970, vol. 48, p. 443-453) which has been incorporated into EMBOSS Needle, using a BLOSUM62 matrix, a "gap open penalty" of 10, a "gap extend penalty" of 0.5, a false "end gap penalty", an "end gap open penalty" of 10 and an "end gap extend penalty" of 0.5. Two molecules having the same primary amino acid or nucleic acid sequence are identical irrespective of any chemical and/or biological modification. For example, two antibodies having the same primary amino acid sequence but different glycosylation patterns are identical by this definition. In case of nucleic acids, for example, two molecules having the same sequence but different linkage components such as thiophosphate instead of phosphate are identical by this definition.

"Similar" protein sequences are those which, when aligned, share similar amino acid residues and most often, but not mandatorily, identical amino acid residues at the same positions of the sequences to be compared. Similar amino acid residues are grouped by chemical characteristics of the side chains into families. Said families are described below for "conservative amino acid substitutions". The "percent similarity" between sequences is the number of positions that contain identical or similar residues at the same sequence positions of the sequences to be compared divided by the total number of positions compared and multiplied by 100%. For instance, if 6 out of 10 sequence positions have identical amino acid residues and 2 out of 10 positions contain similar residues, then the sequences have 80% similarity. The similarity between two sequences can e.g. be determined using EMBOSS Needle.

A "variant" refers to an amino acid or nucleic acid sequence which differs from the parental sequence by virtue of addition (including insertions), deletion and/or substitution of one or more amino acid residues or nucleobases while retaining at least one desired activity of the parent sequence disclosed herein. In the case of antibodies such desired activity may include specific antigen binding. Similarly, a variant nucleic acid sequence may be modified when compared to the parent sequence by virtue of addition, deletion and/or substitution of one or more nucleobases, but the encoded antibody retains the desired activity as described above. Variants may be naturally occurring, such as allelic or splice variants, or may be artificially constructed.

As used herein, the term "conservative modifications" refers to modifications that are physically, biologically, chemically or functionally similar to the corresponding reference, e.g., has a similar size, shape, electric charge, chemical properties, including the ability to form covalent or hydrogen bonds, or the like. Such conservative modifications include, but are not limited to, one or more nucleobases and amino acid substitutions, additions and deletions.

For example, conservative amino acid substitutions include those in which the amino acid residue is replaced with an amino acid residue having a similar side chain. For example, amino acid residues being non-essential with regard to binding to an antigen can be replaced with another amino acid residue from the same side chain family, e.g. serine may be substituted for threonine. Amino acid residues are usually divided into families based on common, similar side-chain properties, such as:
 1. nonpolar side chains (e.g., glycine, alanine, valine, leucine, isoleucine, methionine),
 2. uncharged polar side chains (e.g., asparagine, glutamine, serine, threonine, tyrosine, proline, cysteine, tryptophan),
 3. basic side chains (e.g., lysine, arginine, histidine, proline),
 4. acidic side chains (e.g., aspartic acid, glutamic acid),
 5. beta-branched side chains (e.g., threonine, valine, isoleucine) and
 6. aromatic side chains (e.g., tyrosine, phenylalanine, tryptophan, histidine).

A conservative substitution may also involve the use of a non-natural amino acid.

Non-conservative substitutions, i.e. exchanging members of one family against members of another family, may lead to substantial changes, e.g., with respect to the charge, dipole moment, size, hydrophilicity, hydrophobicity or conformation of the binding member, which may lead to a. significant drop in the binding activity, in particular if amino acids are affected that are essential for binding to the target molecule. A non-conservative substitution may also involve the use of a non-natural amino acid.

Conservative and non-conservative modifications can be introduced into parental binding members by a variety of standard techniques known in the art, such as combinatorial chemistry, site-directed DNA mutagenesis, PCR-mediated and/or cassette mutagenesis, peptide/protein chemical synthesis, chemical reaction specifically modifying reactive groups in the parental binding member. The variants can be tested by routine methods for their chemical, biological, biophysical and/or biochemical properties.

Nucleic acid hybridization reactions can be performed under conditions of different stringency. "Stringent conditions" are widely known and published in the art. Typically, during the hybridization reaction a SSC-based buffer can be used in which SSC is 0.15 M NaCl and 15 mM citrate buffer having a pH of 7.0. Increasing buffer concentrations and the presence of a denaturing agent increase the stringency of the hybridization step. For example, high stringency hybridization conditions can involve the use of: (i) 50% (vol/vol) formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C. with washes at 42° C. in 0.2×SSC and 0.1% SDS; (ii) 50% (vol/vol) formamide with 0.1% bovine serum albumin/0.1%

Ficoll/0.1% polyvinylpyrrolidone/50 mM sodium phosphate buffer at pH 6.5 with 750 mM sodium chloride, 75 mM sodium citrate at 42° C.; or (iii) 10% dextran sulfate, 2×SSC, and 50% formamide at 55° C., followed by a high-stringency wash consisting of 0.1×SSC containing EDTA at 55° C. Additionally or alternatively, one, two or more washing steps using wash solutions of low ionic strength and high temperature can be included in the hybridization protocol using, for example, 0.015 M sodium chloride/0.0015 M sodium citrate/0.1% sodium dodecyl sulfate at 50° C.

Various aspects of the invention are described in further detail in the following subsections. It is understood that the various embodiments, preferences and ranges may be combined at will. Further, depending of the specific embodiment, selected definitions, embodiments or ranges may not apply.

In a first aspect, the invention provides a monovalent antibody fragment binding IL-1 beta which inhibits the biological effect of human IL-1 beta with an $IC_{50}$ of lower than 50 pM. Said $IC_{50}$ is preferably lower than about 40 pM, more preferably lower than about 30, 20, 10, 5, 4, 3, 2 or 1 pM.

Preferably, said monovalent antibody fragment has a molecular weight of about 50 kDa or lower, such as about 45 kDa, 40 kDa, 35 kDa or lower, preferably about 25 kDa, such as 23, 24, 25, 26, or 27 kDa.

In one aspect, the invention provides an antibody, comprising:
(a) at least one of the VH CDR sequences CDR-H1, CDR-112 or CDR-H3 as set forth in SEQ ID Nos.: 1, 2 and 3, respectively, or variants thereof, and/or
(b) at least one of the VL CDR sequences CDR-L1, CDR-L2 or CDR-L3 as set forth in SEQ ID Nos.: 4, 5, and 6, respectively, or variants thereof.

Such antibody may comprise:
(a) at least one of the VH CDR sequences CDR-H1, CDR-H2 or CDR-H3 as set forth in SEQ ID Nos.: 155, 156 and 157, respectively, or variants thereof; and/or
(b) at least one of the VL CDR sequences CDR-L1, CDR-L2 or CDR-L3,
(i) as set forth in SEQ ID Nos.: 158, 159 and 160, respectively, or variants thereof, or
(ii) as set forth in SEQ ID Nos.: 161, 162 and 163, respectively, or variants thereof.

Preferably, the antibody comprises at least the CDR-H3 of SEQ ID No.: 3 and the CDR-L3 of SEQ ID No.: 6 or SEQ ID No.: 157, or a variant thereof, respectively. Even more preferably, said antibody comprises all six CDRs of:
(i) SEQ ID Nos.: 1 to 6 or variants thereof;
(ii) SEQ ID Nos.: 155 to 160 or variants thereof; or
(iii) SEQ ID Nos.: 155 to 157 and SEQ ID Nos.: 161 to 163 or variants thereof.

Such antibody has a very high inhibitory potency against human IL-1 beta with an $IC_{50}$ of lower than 50 pM, more preferably lower than about 40 pM, 30, 20, 10, and even more preferably lower than 5 pM and most preferably about 1 pM and lower.

Preferably, the antibody has an inhibitory potency against human IL-1 beta with an $IC_{50}$ of at least 2 pM, more preferably of at least 1 pM.

The $IC_{50}$ can, e.g., be determined using a cell based potency assay. In one embodiment, the $IC_{50}$ value above is determined by inhibiting the IL-1 beta induced release of IL-6 from human fibroblasts. Such assay is based on the observation that fibroblasts stimulated with IL-1 beta release IL-6. In the presence of IL-1 beta inhibiting antibodies, the concentration of released IL-6 is reduced. In a preferred embodiment, Normal Human Dermal Fibroblasts (NHDF-Neo, e.g., obtainable from Lonza Walkersville USA, cat. no. CC-2509) cells are used. Upon incubation with a mixture of hIL-1 beta and the antibody of interest, supernatants are harvested and examined by an IL-6 ELISA such as the R&D Systems Human IL-6 DuoSet ELISA kit (R&D Systems, cat. no. DY206). In one embodiment, the assay is the IL-1 beta neutralization assay as described in example 3. Preferably, the $IC_{50}$ value is the mean value obtained of at least three independent repetitions of such assay.

The antibody described herein may be a full-length immunoglobulin or an antibody fragment, such as a Fab, Fab', F(ab')$_2$, scFv, Fv fragment, nanobody, VHH or minimal recognition unit.

In a preferred embodiment the antibody and in particular the monovalent antibody fragment above is a scFv. The VH and VL domains can be connected in either orientation, VL-linker-VH or VH-linker-VL, by a flexible linker. In a preferred embodiment, the orientation is VL-linker-VH, i.e. the light chain variable region being at the N-terminal end and the heavy chain variable region being at the C-terminal end of the polypeptide.

The antibody is preferably humanized. Such humanized antibody may, e.g., comprise in the variable light chain the FR-L1 of SEQ ID No.: 18, the FR-L2 of SEQ ID No.: 19, the FR-L3 of SEQ ID No.: 20 and/or the FR-L4 of SEQ ID No.: 21 or variants thereof. Additionally or alternatively, the humanized antibody can comprise the heavy chain variable framework region FR-H1 of SEQ ID No.: 22, 26 or 30; the heavy chain variable framework region FR-H2 of SEQ ID No.: 23, 27 or 31; the heavy chain variable framework region FR-H3 of SEQ ID No.; 24, 28 or 32; and/or the heavy chain variable framework region FR-H4 of SEQ ID No.: 25, 29 or 33.

Thus, in a preferred embodiment, the antibody comprises the VH sequence of SEQ ID No.: 7 or SEQ ID No.: 146, or a variant thereof respectively. Such variant has at least 85%, more preferably 90%, 91%, 92%, 93%, 94%, 95%, 96%, 97%, 98%, 99% and most preferably 100% sequence identity to SEQ ID No.: 7 or SEQ ID No.: 146. Examples of such variant VH sequences include, without being limited to, SEQ ID No.: 121, SEQ ID No.: 122, SEQ ID No.: 124, SEQ ID No.: 126, SEQ ID No.: 128, SEQ ID No.: 130, SEQ ID No.: 132, SEQ ID No.: 134, SEQ ID No.: 142, SEQ ID No.: 144, SEQ ID No.: 146, SEQ ID No.: 148, SEQ ID No.: 150 or SEQ ID No.: 152.

Additionally or alternatively, the antibody disclosed herein comprises the VL sequence selected from the group consisting of SEQ ID No.: 8, SEQ ID No.: 136 and SEQ ID No.: 145, or a variant thereof, respectively. Such variant has at least 85%, more preferably 90%, 91%, 92%, 93%, 94%, 95%, 96%, 97%, 98%, 99% and most preferably 100% sequence identity to SEQ ID No.: 8, SEQ ID No.; 136 or SEQ ID No.: 145. Examples of such variant VL sequences include, without being limited to, SEQ ID No.: 123, SEQ ID No.: 125, SEQ ID No.: 127, SEQ ID No.: 129, SEQ ID No.: 131, SEQ ID No.: 133, SEQ ID No.: 135, SEQ ID No.: 136, SEQ ID No.: 137, SEQ ID No.: 139 or SEQ ID No.: 153.

In one embodiment, the antibody comprises a VH sequence having at least 85%, more preferably 90%, 91%, 92%, 93%, 94%, 95%, 96%, 97%, 98%, 99% and most preferably 100% sequence similarity to SEQ ID No.: 7 or SEQ ID No.; 146. Additionally or alternatively, the antibody comprises a VL sequence having at least 85%, more preferably 90%, 91%, 92%, 93%, 94%, 95%, 96%, 97%, 98%, 99% and most preferably 100% sequence similarity to SEQ ID No.: 8, SEQ ID No.: 136 or SEQ ID No.: 145.

In a much preferred embodiment, the antibody comprises the VH as set forth in to SEQ ID No.: 7 and the VL as set forth in SEQ ID No.: 8. The framework sequences of both SEQ ID No.: 7 and SEQ ID No.: 8 are derived from a human immunoglobulin described in WO 03/097697 A (ESBATech AG). Its VH and VL framework sequences have been modified for humanization and stabilization of rabbit antibodies, see, e.g., WO 2009/155726 A (ESBATech, AN ALCON BIOMEDICAL RESEARCH UNIT LLC); BORRAS, L., et al. Generic approach for the generation of stable humanized single-chain Fv fragments from rabbit monoclonal antibodies. *Journal of Biological Chemistry* 2010, vol. 285, no. 12, p. 9054-9066. In one embodiment, the VL framework of the antibody disclosed herein comprises SEQ ID Nos.: 18-21 or variants thereof. Additionally or alternatively, the VH framework of the antibody comprises SEQ ID Nos.: 22-25, SEQ ID Nos.: 26-29 or SEQ ID Nos.: 30-33 or variants thereof, respectively.

In another preferred embodiment, the antibody comprises the VH as set forth in to SEQ ID No.: 146 and the VL as set forth in SEQ ID No.: 8 or in SEQ ID No.: 145.

In another preferred embodiment, the antibody comprises the VH as set forth in to SEQ ID No.: 146 and the VL as set forth in SEQ ID No.: 136.

The antibody, in particular in case of a scFv, may comprise a linker sequence. Such linker sequence has typically ten to about 25 amino acids. Usually, such linker peptide is rich in glycines, which confer flexibility, as well as serines and/or threonines for improved solubility. In a preferred embodiment, a (GGGGS)$_4$ linker (SEQ ID No.: 9) or a variant thereof is used. Variations of said motif having three to five repeats may also be used. Further suitable linkers are described, e.g., in ALFTHAN, K. Properties of a single-chain antibody containing different linker peptides, *Protein Engineering* 1995, vol. 8, no. 7, p. 725-731.

In certain embodiments variants of the antibodies provided herein are contemplated. For example, it may be desirable to improve antigen binding, antibody-dependent cell-mediated cytotoxicity (ADCC), complement-dependent cytotoxicity (CDC), to increase stability or solubility, to decrease immunogenicity and/or to alter other biological, biochemical or biophysical properties of the antibody. In some embodiments the variant does not show any improvement over the parent antibody.

Variants of the antibodies provided herein may be prepared by protein and/or chemical engineering, introducing appropriate modifications into the nucleic acid sequence encoding the antibody, or by protein/peptide synthesis. Any combination(s) of deletions, substitutions, additions and insertions can be made to the framework or to the CDRs, provided that the generated antibody possesses the desired characteristics for which it can be screened using appropriate methods. Of particular interest are substitutions, preferably conservative substitutions as described above. Preferred conservative substitutions include:

1. Substituting alanine (A) by valine (V);
2. Substituting arginine (R) by lysine (K);
3. Substituting asparagine (N) by glutamine (Q);
4. Substituting aspartic acid (D) by glutamic acid (E);
5. Substituting cysteine (C) by serine (S);
6. Substituting glutamic acid (E) by aspartic acid (D);
7. Substituting glycine (G) by alanine (A);
8. Substituting histidine (H) by arginine (R) or lysine (K);
9. Substituting isoleucine (I) by leucine (L);
10. Substituting methionine (M) by leucine (L);
11. Substituting phenylalanine (F) by tyrosine (Y);
12. Substituting proline (P) by alanine (A);
13. Substituting serine (S) by threonine (T);
14. Substituting tryptophan (W) by tyrosine (Y);
15. Substituting phenylalanine (F) by tryptophan (W); and/or
16. Substituting valine (V) by leucine (L) and vice versa.

The antibody described herein may comprise one or more, such as two, three, four, five, six, seven, eight, nine, ten, eleven, twelve or more of such conservative substitutions.

Non-conservative substitutions may lead to more substantial changes, e.g., with respect to the charge, dipole moment, size, hydrophilicity, hydrophobicity or conformation of the polypeptide. In one embodiment the antibody comprises one or more, such as two, three, four, five, six, seven, eight, nine, ten, eleven, twelve or more of such non-conservative substitutions.

Modifications may be present in the CDRs or in the framework sequences. For example, the CDRs provided herein may comprise one, two, three, four, five or even more modifications. For example, the CDR-L1, CDR-L2 and CDR-L3 sequences taken as a whole are at least 75%, preferably at least 76%, 77%, 78%, 79%, 80%, 85%, 90%, 91%, 92%, 93%, 94%, 95%, 96%, 97%, 98% or more preferably 99% identical to the CDRs provided herein, in particular to (i) SEQ ID Nos.: 4, 5 and 6, or to (ii) SEQ ID Nos.: 161, 162 and 163. Additionally or alternatively, the CDR-H1, CDR-H2 and CDR-H3 sequences taken as a whole are at least 80%, preferably at least 81%, 82%, 83%, 84%, 95%, 90%, 91%, 92%, 93%, 94%, 95%, 96%, 97%, 98% or more 0.5 preferably 99% identical to the CDRs provided herein, in particular to (i) SEQ ID Nos.: 1, 2 and 3, or to (ii) SEQ ID Nos.; 155, 156 and 157.

In one embodiment the CDR-L1, CDR-L2, CDR-L3, CDR-H1, CDR-H2 and CDR-H3 taken as a whole are at least 85%, preferably 90%, 91%, 92%, 93%, 94%, 95%, 96%, 97%, 98% or more preferably 99% similar to the CDRs provided herein. Additionally or alternatively, the CDR-L1, CDR-L2, CDR-L3, CDR-H1, CDR-H2 and CDR-H3 taken as a whole are at least 85%, preferably 90%, 91%, 92%, 93%, 94%, 95%, 96%, 97%, 98% or more preferably 99% similar to the CDRs provided herein.

Therefore, a variant may, e.g., comprise one, two, three, four or five substitutions in SEQ ID No.: 4. Much preferred are substitutions at positions marked with X in SEQ ID No.: 14. The variant may, e.g., comprise:

(i) alanine (A), cysteine (C), aspartic acid (D), glutamic acid (E), phenylalanine (F), glycine (G), histidine (H), isoleucine (I), lysine (K), leucine (L), methionine (M), asparagine (N), proline (I), glutamine (Q), arginine (R), serine (S), threonine (T), valine (V), tryptophan (W), tyrosine (Y) at AHo position 32 of the variable light chain;

(ii) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), serine (S), threonine (T), valine (V), tryptophan (W), tyrosine (Y) at AHo position 33 of the variable light chain; and/or (iii) glutamic acid (E), phenylalanine (F), glycine (G), methionine (M), asparagine (N), glutamine (Q), serine (S), tryptophan (W), tyrosine (Y) at AHo position 40 of the variable light chain.

Additionally or alternatively, a variant comprises one, two, three, or four substitutions in SEQ ID No.: 5. Much preferred are substitutions at positions marked with X in SEQ ID No.: 15. Such variant may, e.g., comprise:

(i) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), tryptophan (W), tyrosine (Y) at AHo position 58 of the variable light chain; and/or (ii) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 69 of the variable light chain.

Additionally or alternatively, a variant comprises one, two, three, four, five or six substitutions in SEQ ID No.: 6. Much preferred are substitutions at positions marked with X in SEQ ID No.: 16. For example, such variant may comprise:

(i) alanine (A), cysteine (C), isoleucine (I), asparagine (N), serine (S), threonine (T), valine (V) at AHo position 109 of the variable light-chain;

(ii) alanine (A), glycine (G), proline (P), serine (S) at AHo position 111 of the variable light chain;

(iii) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 112 of the variable light chain;

(iv) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 135 of the variable light chain; and/or (v) alanine (A), cysteine (C), aspartic acid (D), glutamic acid (E), phenylalanine (F), glycine (G), histidine (H), isoleucine (I), leucine (L), methionine (M), asparagine (N), proline (P), glutamine (Q), arginine (R), serine (S), threonine (T), valine (V), tryptophan (W), tyrosine (Y) at AHo position 136 of the variable light chain.

Additionally or alternatively, a variant comprises one, two, three, or four substitutions in SEQ ID No.: 1 or in SEQ ID No.: 155. Much preferred are substitutions at positions marked with X in SEQ ID No.: 11. Such variant may, e.g., comprise:

(i) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 33 of the variable heavy chain; and/or (ii) alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), arginine (R), serine (S), threonine (T), valine (V), tryptophan (W), tyrosine (Y) at AHo position 39 of the variable heavy chain.

Additionally or alternatively, a variant comprises one, two, three, four, five or six substitutions in SEQ ID No.: 2 or in SEQ ID No.: 156. Much preferred are substitutions at positions marked with X in SEQ ID No.: 12. For example, the variant may comprise:

(i) alanine (A), cysteine (C), glycine (G), methionine (M) or tyrosine (Y) at AHo position 59 of the variable heavy chain;

(ii) aspartic acid (D), asparagine (N) or proline (P) at AHo position 60 of the variable heavy chain; and/or (iii) alanine (A), aspartic acid (D), glutamic acid (E), glycine (G), phenylalanine (F), histidine (H), isoleucine (I), lysine (K), leucine (L), methionine (M), asparagine (N), proline (P), serine (S), threonine (T), tryptophan (W) or tyrosine (Y) at AHo position 69 of the variable heavy chain.

Additionally or alternatively, a variant comprises one, two, three, four, five, six, seven, eight, nine, ten or eleven substitutions in SEQ ID No.: 3 or in SEQ ID No.: 157. Much preferred are substitutions at positions marked with X in SEQ ID No.: 13. Such variant may, e.g., comprise:

(i) alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), arginine (R), serine (S), threonine (T), valine (V), tryptophan (W), tyrosine (Y) at AHo position 110 of the variable heavy chain;

(ii) alanine (A), cysteine (C), aspartic acid (D), phenylalanine (F), glycine (G), histidine (H), isoleucine (I), lysine (K), methionine (M), asparagine (N), proline (P), glutamine (Q), arginine (R), serine (S), threonine (T), valine (V), tryptophan (W), tyrosine (Y) at AHo position 111 of the variable heavy chain;

(iii) alanine (A), cysteine (C), phenylalanine (F), histidine (H), isoleucine (I), leucine (L), methionine (M), asparagine (N), glutamine (Q), serine (S), threonine (T), valine (V), tyrosine (Y) at AHo position 112 of the variable heavy chain;

(iv) phenylalanine (F) or isoleucine (I) at AHo position 113 of the variable heavy chain;

(v) alanine (A), cysteine (C), glutamic acid (E), glycine (G), serine (S), threonine (T), valine (V) at AHo position 114 of the variable heavy chain;

(vi) alanine (A), glycine (G), methionine (M) or asparagine (N) at AHo position 115 of the variable heavy chain;

(Vii) alanine (A), aspartic acid (D), glutamic acid (E), histidine (H), asparagine (N), serine (S), threonine (T) at AHo position 135 of the variable heavy chain;

(Viii) alanine (A), cysteine (C), phenylalanine (F), glycine (G), histidine (H), isoleucine (I), leucine (L), methionine (M), asparagine (N), glutamine (Q), serine (S), threonine (T), valine (V), tryptophan (W), tyrosine (Y) at AHo position 136 of the variable heavy chain;

(ix) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 137 of the variable heavy chain; and/or (x) alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y) at AHo position 138 of the variable heavy chain.

A particularly preferred type of variant is one where one or more entire CDRs are replaced. Typically, the CDR-H3 and CDR-L3 contribute most significantly to antigen binding. For example, the entire CDR-L1, CDR-L2, CDR-H1 and/or CDR-H2 may be replaced by a different CDR of natural or artificial origin. In some embodiments, one or more CDRs are replaced by an alanine-cassette.

In one embodiment, the variant described herein has at least 85%, more preferably 90%, 91%, 92%, 93%, 94%, 95%, 96%, 97%, 98%, 99% and most preferably 100% sequence identity to a sequence selected from the group consisting of SEQ ID No.: 10, SEQ ID No.: 73 and SEQ ID No.: 82.

In one embodiment, the variant described herein has at least 85%, more preferably 90%, 91%, 92%, 93%, 94%, 95%, 96%, 97%, 98%, 99% and most preferably 100% sequence similarity to SEQ ID No.: 10, SEQ ID No.: 73 and SEQ ID No.; 82.

Additionally or alternatively, the VH of the antibody comprises solubility enhancing point mutations. WO2009/155725 (ESBATech, a Novartis company) describes a motif, which has proven to increase the overall solubility of the antibody. The residues are placed at positions located in the interface of the variable domain and the constant domain of an antibody and stabilize antibody fragments, in particular scFv, lacking the constant domain. In particular, one, preferably all three of the following residues are present:

(i) serine (S) at heavy chain amino acid position 12 (according to AHo numbering);

(ii) serine (S) or threonine (T) at heavy chain amino acid position 103 (according to AHo numbering); and/or (iii) serine (S) or threonine (T) at heavy chain amino acid position 144 (according to AHo numbering).

In a preferred embodiment the antibody has a serine at VH position 12; a serine at VH position 103; and a threonine at VH position 144 (all AHo numbering).

Thus, in one embodiment the antibody disclosed herein comprises the VH framework sequences of SEQ ID Nos.: 30-33 or variants thereof.

Preferably, a variant antibody as used herein:

(i) retains specific binding to IL-1 beta, in particular to hIL-1 beta;

(ii) has a potency ($IC_{50}$) with regard to inhibiting the biological effect of human IL-1 beta of lower than 500 pM, preferably lower than 400 pM, 300 pM, 200 pM, 100 pM, 50 pM, more preferably of lower than 25 pM;

(iii) is cross-reactive with cynomolgus IL-1 beta, rhesus monkey IL-1 beta and/or rat IL-1 beta; and/or (iv) competes with the antibody disclosed herein for binding to IL-1 beta, preferably human IL-1 beta, cynomolgus IL-1 beta, rhesus monkey IL-1 beta and/or rat IL-1 beta, most preferably hIL-1 beta.

In one embodiment, the variant comprises a VL sequence selected from the group consisting of SEQ ID No.: 96, SEQ ID No.: 97, SEQ ID No.: 98, SEQ ID No.: 99, SEQ ID No.: 100, SEQ ID No.: 101, SEQ ID No.: 102, SEQ ID No.: 103, SEQ ID No.: 104, SEQ ID No.: 105, SEQ ID No.: 123, SEQ ID No.: 125, SEQ ID No.: 127, SEQ ID No.: 129, SEQ ID No.: 131, SEQ ID No.: 133, SEQ ID No.: 135, SEQ ID No.: 136, SEQ ID No.: 137, SEQ ID No.: 139, SEQ ID No.: 141, SEQ ID No.: 143, SEQ ID No.; 145, SEQ ID No.: 147, SEQ ID No.: 149, SEQ ID No.: 151 and SEQ ID No.: 153.

Additionally or alternatively, the variant comprises a VH sequence selected from the group consisting of SEQ ID No.: 106, SEQ ID No.: 107, SEQ ID No.: 108, SEQ ID No.: 109, SEQ ID No.: 110, SEQ ID No.: 111, SEQ ID No.: 112, SEQ ID No.: 113, SEQ ID No.: 114, SEQ ID No.: 115, SEQ ID No.: 116, SEQ ID No.: 117, SEQ ID No.: 118, SEQ ID No.: 119, SEQ ID No.: 120, SEQ ID No.: 121, SEQ ID No.: 122, SEQ ID No.: 124, SEQ ID No.: 126, SEQ ID No.: 128, SEQ ID No.: 130, SEQ ID No.: 132, SEQ in No.: 134, SEQ ID No.: 138, SEQ ID No.: 140, SEQ ID No.: 142, SEQ ID No.: 144, SEQ ID No.: 146, SEQ ID No.: 148, SEQ ID No.: 150, SEQ ID No.: 152.

Variants may also be prepared by chain shuffling of light and heavy chains. A single light chain can be combined with a library of heavy chains to yield a library of variants. In one embodiment, said single light chain is selected from the group of VL sequences recited above and/or said library of heavy chains comprises one or more of the VH sequences recited above. Likewise, a single heavy chain can be combined with a library of light chains. Preferably, said single heavy chain is selected from the group of VH sequences recited above and/or said library of light chains comprises one or more of the VL sequences recited above.

In one embodiment, the variant comprises the VL of SEQ ID No.: 135 and/or the VI of SEQ ID No.: 7, SEQ ID No.: 142, SEQ ID No.: 146, SEQ ID No.: 150 or SEQ ID No.: 152. Preferably, the variant comprises SEQ ID No.: 67, SEQ ID No.: 85, SEQ ID No.: 86, SEQ ID No.: 87 or SEQ ID No.: 88.

In one embodiment, the variant comprises the VL of SEQ ID No.: 136 and/or the VI of SEQ ID No.: 7, SEQ ID No.: 142, SEQ ID No.: 146, SEQ ID No.: 150 or SEQ ID No.: 152. Preferably, the variant comprises SEQ ID No.: 68, SEQ ID No.: 81, SEQ ID No.: 82, SEQ ID No.: 83 or SEQ ID No.: 84.

In one embodiment, the variant comprises the VL of SEQ ID No.: 137 and/or the VH of SEQ ID No.: 7, SEQ ID No.: 138, SEQ ID No.: 142, SEQ ID No.: 146, SEQ ID No.: 150 or SEQ ID No.: 152. Preferably, the variant comprises SEQ ID No.: 69, SEQ ID No.: 92, SEQ ID No.: 93, SEQ ID No.: 94 or SEQ ID No.: 95.

In one embodiment, the variant comprises the VL of SEQ ID No.: 139 and/or the VH of SEQ ID No.: 140, SEQ ID No.: 142, SEQ ID No.: 146, SEQ ID No.: 150 or SEQ ID No.: 152. Preferably, the variant comprises SEQ ID No.: 70, SEQ ID No.: 77, SEQ ID No.: 78, SEQ ID No.: 79 or SEQ ID No.: 80.

In one embodiment, the variant comprises the VL of SEQ ID No.: 141 and/or the VH of SEQ ID No.: 142. Preferably, the variant comprises SEQ ID No.: 71.

In one embodiment, the variant comprises the VL of SEQ ID No.: 143 and/or the VH of SEQ ID No.: 144. Preferably, the variant comprises SEQ ID No.: 72.

In one embodiment, the variant comprises the VL of SEQ ID No.: 145 and/or the VH of SEQ ID No.: 146. Preferably, the variant comprises SEQ ID No.: 73.

In one embodiment, the variant comprises the VL of SEQ ID No.: 147 and/or the VI of SEQ ID No.; 148. Preferably, the variant comprises SEQ ID No.: 74.

In one embodiment, the variant comprises the VL of SEQ ID No.: 149 and/or the VH of SEQ ID No. 150. Preferably, the variant comprises SEQ ID No.: 75.

In one embodiment, the variant comprises the VL of SEQ ID No.: 151 and/or the VH of SEQ ID No. 152. Preferably, the variant comprises SEQ ID No.: 76.

In one embodiment, the variant comprises the VL of SEQ ID No.: 8 and/or the VH of SEQ ID No.: 121 or of SEQ ID No.: 122. Preferably, the variant comprises SEQ ID No.: 59 or SEQ ID No.: 60.

In one embodiment, the variant comprises the VL of SEQ ID No.: 153 and/or the VH of SEQ ID No.: 142, SEQ ID No.: 146 or SEQ ID No.: 152. Preferably, the variant comprises SEQ ID No. 89, SEQ ID No.: 90 or 91.

In one embodiment, the variant comprises the VL of SEQ ID No.: 8 and/or the VH of SEQ ID No.: 121, SEQ ID No.;

122, SEQ ID No.: 142, SEQ ID No.: 144, SEQ ID No.: 146, SEQ ID No.: 148, SEQ ID No.: 150 or SEQ ID No.: 152.

In one embodiment, the variant comprises the VH of SEQ ID No.: 7 and/or the VL of SEQ ID No.: 135, SEQ ID No.: 136, SEQ ID No.: 137, SEQ ID No.: 139 or SEQ ID No.: 153.

In one embodiment, the variant comprises a sequence selected from the group consisting of SEQ ID No.: 34 to 95 and SEQ ID No.: 154.

A binding member can comprise any of the VL and/or the VH sequences mentioned above. Binding members having a single domain format, such as a nanobody or a VHH, comprise only one of either the VL or VH sequences mentioned above, preferably the VH sequence. Multivalent binding members, in particular F(ab')$_2$ fragments, bis-scFv or diabodies, preferably bispecific binding members, may comprise one or more of the VL sequences mentioned above and/or one or more of the VH sequences mentioned above.

The antibodies of the instant invention are particularly stable. As used herein the term "stability" refers to the biophysical property of the antibody to remain monomeric in solution after prolonged incubation and/or incubation at elevated temperature. Unstable antibodies tend to dimerize or oligomerize and even precipitate, thereby decreasing shelf-life and becoming less suitable for pharmaceutical applications.

The antibodies provided herein and in particular the monovalent antibody fragment above remain monomeric at least to 75%, preferably at least to 80%, 85%, and most preferably to 93% after being incubated for 1 month at 37° C. at a concentration of 1 mg/ml in PBS at pH 7.2. Additionally or alternatively, the antibody remains monomeric at least to 90%, preferably at least to 92%, 94%, 96%, 98% more preferably to 100% after 1 month at room temperature at a concentration of 1 mg/ml in PBS at pH 7.2.

The degree of monomers can, e.g., be determined by SEC-HPLC (Size Exclusion Chromatography-High-Performance Liquid Chromatography). A suitable mobile phase for such testing is, e.g., PBS at pH 7.2. The monomer content can be quantified by peak integration of the UV280 signal measured during the protein chromatography. A suitable system is, e.g., a Dionex Summit HPLC controlled by CHROMELEON® 6.5 software that also allows for subsequent chromatogram analysis and peak quantification.

The antibodies disclosed herein and in particular the monovalent antibody fragment above are also stable at higher concentrations, for example, they remain monomeric at least to 50%, preferably at least to 55%, 60%, 65%, 70% and most preferably to 75% after being incubated for 2 weeks at room temperature and/or 4° C. at a concentration of about 50 mg/ml in PBS at pH 7.2.

Moreover, the antibodies provided herein and in particular the monovalent antibody fragment above are particularly soluble and can therefore be highly concentrated without precipitation due to aggregate formation. Preferably, the antibodies can be concentrated in PBS at pH 7.2 to a concentration of more than 20 mg/ml without precipitation, more preferably to a concentration of 30 mg/ml, 40 mg/ml, 50 mg/ml, 60 mg/ml and most preferably to 70 mg/ml in. PBS at pH 7.2.

In a much preferred embodiment, the antibody has a melting temperature of about 60° C. as determined by differential scanning fluorimetry (DSF), preferably 65° C., 70° C., 71° C., 72° C., 73° C. and most preferably 74° C. This method is based on the properties of certain dyes being fluorescent only in a hydrophobic environment. For example, protein unfolding can be detected as an increase in fluorescence upon binding of the dye SYPRO® Orange to a heat-denatured protein (NIESEN F. H. et al. The use of differential scanning fluorimetry to detect ligand interactions that promote protein stability. *Nature Protocols* 2007, vol. 2, p. 2212-2221). The stability of a protein can thus be analyzed by thermal denaturation.

The antibody has preferably a theoretical isoelectric point (pI) in the range of 5 to 10, preferably 7 to 9, most preferably about 8.3. The theoretical pI can, for example, be calculated by using the ProtParam tool on the ExPASy Server (see also GASTEIGER E. et al. Protein Identification and Analysis Tools on the ExPASy Server. (In) The Proteomics Protocols Handbook. Edited by WALKER J. M. Totowa: Humana Press Inc., 2005. ISBN 9781588295934. p. 571-607).

The antibody can be cross-reactive with IL-1 beta from non-human species, such as, without being limited to, cynomolgus IL-1 beta, rhesus monkey IL-1 beta, rat IL-1 beta, murine IL-1 beta, canine IL-1 beta, feline IL-1 beta, marmoset IL-1 beta, swine IL-1 beta and/or guinea pig IL-1 beta. Preferably, the antibody is cross-reactive with cynomolgus IL-1 beta (e.g., recombinantly produced and available from Sino Biological Inc., cat. no. 90010-CNAE), rhesus monkey IL-1 beta (e.g., recombinantly produced and available from R&D Systems, cat. no. 1318-RL/CF) and/or rat IL-1 beta (e.g., recombinantly produced and available from Peprotech, cat. no. 400-01B).

Preferably, there is no residual activity of IL-1 beta when being neutralized with the antibody disclosed herein in an in vivo and/or an in vitro setting, i.e. the antibody completely inhibits the action of IL-1 beta. "No residual activity" as used herein refers to lower than 2% of the potency assay signal corresponding to the IL-6 release from human fibroblasts induced by 10 pg/ml of IL-1 beta, preferably the assay as described in example 3, in presence of 60 ng/ml of the antibody described herein when compared to antibodies of non-relevant specificity or vehicle control at the same concentration.

The invention also provides a binding member competing with the antibodies disclosed herein for binding to human IL-1 beta.

As used herein, the term "competing" refers to the competition between binding members for binding to the same target. Competition can be determined by competitive binding assays in which the binding member of interest prevents or inhibits or reduces specific binding of the antibodies disclosed herein to a common antigen (here, hIL-1 beta or a fragment thereof). Such competitive binding assays are known in the art and include, without being limited to, solid phase direct or indirect radioimmunoassay (RIA) and solid phase direct or indirect enzyme immunoassay (EIA). Typically, such assay involves the use of purified antigen bound to a solid surface, a. binding member to be tested and the reference antibody as described herein. Competitive inhibition is measured by determining the amount of either: (i) the reference antibody bound to the solid surface in the presence of the binding member to be tested, or (ii) the binding member to be tested bound to the solid surface in the presence of the reference antibody. A competing binding member may bind: (i) to the same epitope as the antibody, (ii) to an overlapping epitope, or (iii) to a different epitope on the same target molecule but sterically hindering binding of the antibody to its target.

Usually, when a competing binding member is present in excess, it will reduce specific binding of the antibody as described herein to IL-1 beta by at least 40-45%, 45-50%, 50-55%, 55-60%, 60-65%, 65-70%, 70-75% or 75% or more. Preferably, binding of the antibody is reduced by at least 80-85%, 85-90%, 90-95%, 95-97%, or 97% or more.

In one embodiment, the competing binding member binds to hIL-1 beta with an affinity $K_D$ of at least about 1 pM, 10 pM, 100 pM, 500 pM, 1 nM, 10 nM.

In one embodiment, the binding member is monovalent, such as a scFv or a Fab fragment. In another embodiment, the binding member is multivalent. Such multivalent molecule can be bivalent (such as a full-length immunoglobulin or a F(ab')$_2$ fragment) or comprises at least three target binding sites.

The multivalent binding member can be a bispecific antibody such as a diabody, a single-chain diabody or a tandem scFv (see, e.g., KONTERMANN, R. E. Methods in Molecular Biology. Edited by LO, B. Totowa, N. J.: Humana Press, 2004. ISBN 1588290921. p. 227-242). Said bispecific antibodies may well use shorter linkers then those described above for scFv, i.e., having only one to three repeats of the basic motif of SEQ ID NO: 14 (see, e.g., HOLLIGER, P., et al. Diabodies: small bivalent and bispecific antibody fragments. PNAS 1993, vol. 90, no. 14, p. 6444-6448). In another embodiment the multivalent binding member is a triabody, a minibody or tetrabody.

The invention also provides T-bodies comprising the antibodies disclosed herein. T-bodies are immunoglobulin T-cell receptors (cIgTCRs) which combine the antigen recognition of antibodies with the signal and effector properties of the T-cell receptor complex. In such constructs the antibody is preferably an antibody fragment such as a Fv, a Fab, a scFv or a scFv-Fc, most preferably a scFv. For further discussion of the general design of T-bodies and their applications, see, e.g., SCHIRRMANN, T. and Pecher, G. Handbook of Therapeutic Antibodies. Edited by DÜBEL, S. Weinheim: Wiley-VCH, 2009. ISBN 3527314539, p. 533-561.

The invention further provides a naïve (i.e., being not engineered for increased affinity or potency) binding member against IL-1 beta having a Monovalent Potency (measured, e.g., as affinity ($K_D$) or biological potency in cell-based assays (IC$_{50}$) in units of mol/l) at a certain Molecular Weight (in g/mol) after normalization to the Number of Binding Sites per binding member, as determined by the equation $$K = \text{Monovalent Potency (mol/l)} \times \text{Molecular Weight (g/mol)} / \text{Number of Binding Sites}$$

As described above, monovalent antibody fragments having potency values in the picomolar range are particular and not routinely obtained. Potency often correlates with the size of the binding member: high potency in the picomolar range can be obtained by full-length immunoglobulins, whereas very small antibody fragments such as nanobodies or minimal recognition units, or small non-antibody scaffolds such as affilins often show lower potency values, i.e., in the nanomolar range. Seemingly, there is a minimum for said function K provided by scFv as described herein: the smaller the binding member, and the higher its monovalent potency or affinity, and the more binding sites per molecule, the smaller K. For example, for scFv as described herein, the lower limit of K equals about 50 ng/l whereas the upper limit of K equals about 12,500 ng/l; for the respective full-length immunoglobulins, the lower limit equals about 150 ng/l and the upper K limit equals about 37,500 ng/l; for other binding members having molecular weights smaller than the scFv as described herein, the K value is K>500,000 ng/l. In a preferred embodiment, the K value is about 50 ng/l, 100 ng/l, 200 ng/l, 500 ng/l, 750 ng/l, 1,000 ng/l, 1,250 ng/l, 1,500 ng/l, 1,750 ng/l, 2,000 ng/l, 2,250 ng/l, or 2,500 ng/l.

Nucleic Acids, Vectors, Host Cells and Method of Production

The antibodies described herein are encoded by a single nucleic acid or by two or more nucleic acids, for example each encoding at least one variable region. Knowing the sequence of the antibody or of its parts, cDNAs encoding the polypeptide sequence can be generated by methods well known in the art, e.g. by gene synthesis. These cDNAs can be cloned by standard cloning and mutagenesis techniques into a suitable vector such as an expression vector or a cloning vector. Optionally, the variable light chain is encoded by a separate nucleic acid than the variable heavy chain of the antibody. Further, additional sequences such as tags (e.g., a His-tag), constant domains for the production of a Fab or a full-length immunoglobulin, linkers, the coding sequence of a second binding specificity or another functional polypeptide such as an enzyme to generate a fusion construct or a bispecific molecule may be included into the genetic construct.

Based on the cloning strategy chosen, genetic constructs may generate an antibody having one or more additional residues at the N-terminal or C-terminal end. For example, an N-terminal methionine derived from the start codon or an additional alanine may be present in an expressed polypeptide, unless it has been clipped off post-translationally. It is therefore to be understood that the antibodies disclosed herein comprise the disclosed sequences rather than consist of them.

In one embodiment, the invention provides a nucleic acid sequence comprising at least 300 nucleobases, more preferably at least 350, 400, 450, or 500 nucleobases and having at least 85%, more preferably at least 90%, 91%, 92%, 93%, 94%, 95%, 96%, 97%, 98% or 99% sequence identity to SEQ ID No.: 17. In a much preferred embodiment the nucleic acid sequence is SEQ ID No.: 17.

Additionally or alternatively, the invention provides a nucleic acid sequence comprising at least 300 nucleobases, more preferably at least 350, 400, 450, or 500 nucleobases, which hybridizes with the nucleic acid of SEQ ID No.; 17 under high stringency conditions.

Basic protocols of standard cloning, mutagenesis and molecular biology techniques are described in, e.g., Molecular Cloning, A Laboratory Manual (GREEN, M. and Sambrook, J. Molecular Cloning: a Laboratory Manual. 4th edition. Cold Spring Harbor Laboratory, 2012. ISBN 1936113422).

Appropriate host cells for the expression of the genetic constructs can be prokaryotic or eukaryotic. Suitable prokaryotic host cells are gram-negative or gram-positive and include species of the *Escherichia, Erwinina, Enterobacter, Klebsiella, Pseudomonas* or *Bacillus* families. Much preferred is *Escherichia coli*, in particular *E. coli* strains BL21 (DE3) (LIFE TECHNOLOGIES™, cat. no. C6000.03) and ORIGAMI™ 2(DE3) (Novagen, cat. no 71345).

If post-translational modifications such as glycosylation or phosphorylation are desired, eukaryotic host cells are preferable. For example, eukaryotic microbes such as commonly used *Saccharomyces cerevisiae* or *Pichia pastoris* strains may serve as host cells. Host cells can also include plant or animal cells, in particular insect or mammalian cells. Suitable mammalian cells include, without being limited to, Chinese Hamster Ovary Cells (CHO), Human Embryonic Kidney Cells (HEK), Human Umbilical Vein Endothelial Cells (HUVEC) or NS0 myeloma cells.

The antibody can be produced by expression in a suitable host cell. For example, the expression vectors described above are introduced into a host cell by standard techniques such as electroporation or chemical transformation. The transformed cells are then cultivated under conditions adequate for recombinant protein expression, typically in appropriate nutritional media, optionally modified for inducing promoters, selecting transformants, or amplifying encoding sequences of interest. The antibody is recovered from the culture and optionally purified using standard techniques in the art. The yield of recombinant protein may be improved by optimizing media and culture conditions such as temperature or oxygen supply. In prokaryotes the antibody can be produced in the periplasm, intracellularly as inclusion bodies or be secreted into the medium. Upon harvest, the protein can be purified using methods well known in that art such as gel filtration, ion exchange chromatography, reversed phase chromatography, hydrophobic interaction, mixed mode chromatography and/or affinity chromatography.

In one embodiment the antibody is produced in a cell-free system. This typically involves in vitro transcription followed by in vitro translation of nucleic acid product templates encoding the proteins described herein, e.g., plasmid DNA or PCR product templates. For example, crude lysates from growing cells are used, providing the necessary enzymes as well as the cellular protein synthesis machinery. The necessary building blocks such as amino acids or nucleobases as well as energy delivering molecules and others can be exogenously supplied. Cell-free expression systems can, for example, be based on lysed rabbit reticulocytes (e.g., Rabbit Reticulocyte Lysate System, Promega, cat. no. L4540), HeLa cells (e.g., 1-Step Human In Vitro Translation Kit, Thermo Scientific, cat. no. 88881), insect cells (e.g., EasyXpress Insect Kit II, Qiagen, cat. no. 32561), wheat germs (e.g., Wheat Germ Extract, Promega, cat. no, L4380), or *E. coli* cells (e.g., PUREXPRESS® In Vitro Protein Synthesis Kit, NEB, cat. no. E6800S). Also, optimized cell-free antibody expression systems for improved disulfide bond generation can be used for production. Commercially available kits include insect cell lysates (e.g., EasyXpress Disulfide Insect Kit, Qiagen, cat. no. 32582) or *E. coli* cell lysates (e.g., EasyXpress Disulfide *E. coli* Kit, Qiagen, cat. no. 32572). Cell-free protein synthesis has, e.g., the advantage of being fast, achieving high product yields, allowing for easy modification of reaction conditions, forming a low degree of or even no byproducts. Cell-free protein synthesis may involve biological and/or chemical steps which cannot be conducted in purely biological or chemical production systems. For example, non-natural or chemically-modified amino acids can be incorporated into the protein at desired positions. ScFv-toxin fusion proteins have been successfully produced in cell-free systems (NICHOLLS, P. J., et al. Characterization of single-chain antibody (sFv)-toxin fusion proteins produced in vitro in rabbit reticulocyte lysate. *Journal of Biological Chemistry* 1993, vol. 268, pp. 5302-5308). Thus, in one embodiment a method of producing the antibody described herein, the binding member above or the T-body above is provided comprising the steps of: (a) providing a cell-free system, (b) providing a nucleic acid product template encoding the antibody described herein, the binding member above or the T-body above, (c) allowing for transcription and translation of said nucleic acid product template; (d) recovering, and optionally (e) purifying said antibody, said binding member or said T-body, respectively.

Additionally or alternatively, a method of producing the antibody described herein comprises at least one step of chemical synthesis. For example, the method may be entirely chemical. In another embodiment, the cell-based or the cell-free production systems described above comprise such at least one step of chemical synthesis.

In a preferred embodiment the antibodies described herein are produced in a cell-based system using an expression vector for intracellular expression in *E. coli*. Upon expression the polypeptide is generated as inclusion bodies within the cells which are separated from further cell particles followed by solubilisation in a denaturing agent such as guanidine hydrochloride (GndHCl) and refolded by renaturation procedures well known to the skilled person.

It is to be understood that the nucleic acids, vectors, host cells and method of production described above also apply to the binding members (insofar as they are a protein) and/or to T-bodies described herein.

Chemical and/or Biological Modifications

In one aspect the antibody of the instant invention is chemically and/or biologically modified. Such modification may comprise, but is not limited to, glycosylation, PEGylation, HESylation, Albumin fusion technology, PASylation, labelling with dyes and/or radioisotopes, conjugation with enzymes and/or toxins, phosphorylation, hydroxylation and/or sulfation. Likewise, any binding member, the nucleic acid sequence, the vector and/or the host cell described above can be modified accordingly.

Chemical and/or biological modifications may be conducted to optimize pharmacodynamics or water solubility of the protein or to lower its side effects. For example, PEGylation, PASylation and/or HESylation may be applied to slow down renal clearance and thereby increase plasma half-life time of the antibody. Additionally or alternatively, a modification may add a different functionality to the protein, e.g. a toxin to more efficiently combat cancer cells, or a detection molecule for diagnostic purposes.

Glycosylation refers to a process that attaches carbohydrates to proteins. In biological systems, this process is performed enzymatically within the cell as a form of co-translational and/or post-translational modification. A protein, here the antibody, can also be chemically glycosylated. Typically, but not limited to, glycosylation is (i) N-linked to a nitrogen of asparagine or arginine side-chains; (ii) O-linked to the hydroxy oxygen of serine, threonine, tyrosine, hydroxylysine, or hydroxyproline side-chains; (iii) involves the attachment of xylose, fucose, mannose, and N-acetylglucosamine to a phospho-serine; or (iv) in form of C-mannosylation wherein a mannose sugar is added to a tryptophan residue found in a specific recognition sequence. Glycosylation patterns can, e.g., be controlled by choosing appropriate cell lines, culturing media, protein engineering manufacturing modes and process strategies (HOSSLER, P. Optimal and consistent protein glycosylation in mammalian cell culture. *Glycobiology* 2009, vol. 19, no. 9, p. 936-949).

Protein engineering to control or alter the glycosylation pattern may involve the deletion and/or the addition of one or more glycosylation sites. The creation of glycosylation sites can conveniently be accomplished by introducing the corresponding enzymatic recognition sequence into the amino acid sequence of the antibody or by adding or substituting one or more of the above enumerated amino acid residues.

It may be desirable to PEGylate the antibody. PEGylation may alter the pharmacodynamic and pharmacokinetic properties of a protein. Polyethylene-glycol (PEG) of an appropriate molecular weight is covalently attached to the protein backbone (see, e.g., PASUT, G. and Veronese, F. State of the art in PEGylation: the great versatility achieved after forty years of research. *Journal of Controlled Release* 2012, vol. 161, no. 2, p. 461-472). PEGylation may additionally reduce the immunogenicity by shielding the PEGylated protein from the immune system and/or alter its pharmacokinetics by, e.g. increasing the in vivo stability of the antibody, protecting it from proteolytic degradation, extending its half-life time and by altering its biodistribution.

Similar effects may be achieved by PEG Mimetics, e.g., HESylating or PASylating the antibody. HESylation utilises hydroxyethyl starch ("HES") derivatives, whereas during PASylation the antibody becomes linked to conformationally disordered polypeptide sequences composed of the amino acids proline, alanine and serine. Said PEG Mimetics and related compounds are, e.g., described in BINDER, U. and Skerra, A. Half-Life Extension of Therapeutic Proteins via Genetic Fusion to Recombinant PEG Mimetics, in Therapeutic Proteins: Strategies to Modulate Their Plasma Half-Lives. Edited by KONTERMANN, R., Weinheim, Germany: Wiley-VCH, 2012. ISBN: 9783527328499. p. 63-81.

The antibody may include an epitope and in particular a salvage receptor binding epitope. Such salvage receptor binding epitope typically refers to an epitope of the Fc region of an IgG molecule (e.g., IgG1, IgG2, IgG3, or IgG4) and has the effect of increasing the in vivo half-life of the molecule.

Additionally or alternatively, the antibody is labelled with or conjugated to a second moiety which ascribes ancillary functions following target binding. Said second moiety may, e.g., have an additional immunological effector function, be effective in drug targeting or useful for detection. The second moiety can, e.g., be chemically linked or fused genetically to the antibody using known methods in the art.

Molecules which may serve as second moiety include, without being limited to, radionuclides, also called radioisotopes (e.g., $^{35}S$ $^{32}P$, $^{14}C$, $^{18}F$, $^{125}I$); apoenzymes; enzymes (such as alkaline phosphatase, horseradish peroxidase, beta-galactosidase or angiogenin); co-factors; peptides (e.g., HIS-tags); proteins (incl. lectins); carbohydrates (incl. mannose-6-phosphate tag); fluorophores (including fluorescein isothiocyanate (FITC); phycoerythrin; green/blue/red and other fluorescent proteins; allophycocyanin (APC)); chromophores; vitamins (including biotin); chelators; antimetabolites (e.g., methotrexate), liposomes; toxins including cytotoxic drugs such as taxol, gramicidin D or colchicine; or a radiotoxin.

A labelled antibody is particularly useful for in vitro and in vivo detection or diagnostic purposes. For example, an antibody labelled with a suitable radioisotope, enzyme, fluorophore or chromophore can be detected by radioimmunoassay (RIA), enzyme-linked immunosorbent assay (ELISA), or flow cytometry-based single cell analysis (e.g., FACS analysis), respectively. Similarly, the nucleic acids and/or vectors disclosed herein can be used for detection or diagnostic purposes, e.g. using labelled fragments thereof as probes in hybridization assays. Labelling protocols may, e.g., be found in JOHNSON, I. and Spence, M. T. Z. Molecular Probes Handbook, A Guide to Fluorescent Probes and Labeling Technologies. Life Technologies, 2010. ISBN: 0982927916.

Compositions

The antibody of the instant invention, any binding member, the nucleic acid sequences or the vector disclosed herein can be provided in a composition which further comprises a suitable carrier, excipient or diluent. Much preferred is a composition comprising an antibody described herein.

Such composition can, e.g., be a diagnostic, a cosmetic or a pharmaceutical composition. For therapeutic or cosmetic purposes, said composition is a pharmaceutical composition comprising a pharmaceutical carrier, excipient or diluent, i.e. not being toxic at the dosages and a concentration employed.

Suitable "carrier", "excipients" or "diluents" include, without being limited to: (i) buffers such as phosphate, citrate, or other, organic acids; (ii) antioxidants such as ascorbic acid and tocopherol; (iii) preservatives such as 3-pentanol, hexamethonium chloride, benzalkonium chloride, benzyl alcohol, alkyl paraben, catechol, or cyclohexanol; (iv) amino acids, such as e.g. histidine, arginine; (v) peptides, preferably up to 10 residues such as polylysine; (vi) proteins, such as bovine or human serum albumin: (vii) hydrophilic polymers such as polyvinylpyrrolidone; (viii) monosaccharides, disaccharides, polysaccharides and/or other carbohydrates including glucose, mannose, sucrose, mannitol, trehalose, sorbitol, aminodextran or polyamidoamines; (ix) chelating agents, e.g. EDTA; (x) salt-forming ions such as sodium; (xi) metal complexes (e.g. Zn-protein complexes); and/or (xii) ionic and non-ionic surfactants such as TWEEN™, PLURONICS™ or polyethylene glycol (PEG).

Many of said exemplary compounds have different functions and may, e.g., act as carrier and as diluent. It is also to be understood that the composition may comprise more than one of each carrier, diluent or excipient.

The antibody, the binding member, the nucleic acid sequences or the vector may be provided on solid support materials such as beads and microparticles. Typically, the molecules are linked to such carrier via a covalent bond (optionally involving a linker), noncovalently or admixture. Said beads and microparticles can comprise, for example, starch, cellulose, polyacrylate, polylacetate polyglycolate, poly(lactide-co-glycolide), latex, or dextran.

Therapeutic Applications

The molecules described herein, in particular the antibody, binding member, nucleic acid or vector, are useful as a medicament. Typically, such medicament comprises a therapeutically effective amount of the molecules provided herein. Accordingly, said molecules can be used for the production of a medicament useful in the treatment of IL-1 beta-related disorders.

In one aspect, a method of treating an IL-1 beta-related disorder is provided comprising the steps of administering a pharmaceutically effective amount of the molecules described herein, in particular the antibody, to a subject in need thereof. In one embodiment, the pharmaceutical composition above (i.e., medicament) comprising such pharmaceutically effective amount of the antibody is administered to said subject.

The term "treat" or "treatment" as used herein refers to the administration of a pharmaceutically effective amount of the antibody, binding member, nucleic acid, vector or host cell of the instant invention, to a subject in need thereof to prevent, cure, delay the onset and/or progression, reduce the severity of, stabilize, modulate, cure or ameliorate one or more symptoms of an IL-1 beta-related disorder. Typically, the antibody, binding member, nucleic acid, vector or host cell is provided in a pharmaceutical composition including those previously described herein.

A "therapeutically effective amount" refers to an amount which at the dosage regimen applied yields the desired therapeutic effect, i.e., to reach treatment goals as defined above. The dosage will depend on various factors including patient and clinical factors (e.g., age, weight, gender, clinical history of the patient, severity of the disorder and/or response to the treatment), the nature of the disorder being treated, the particular composition to be administered, the route of administration, and other factors.

The subject in need of such treatment can be a human or a non-human animal, e.g., a mouse, rat, rabbit, monkey, dog, horse, cow, chicken, guinea pig or pig. Typically, the subject is diagnosed with an IL-1 beta-related disorder or may acquire such a disorder.

Examples of IL-1 beta-related disorders, in which antagonist of IL-1 beta have shown therapeutic effects include, without being limited to, proliferative diabetic retinopathy, gouty arthritis, Schnitzler syndrome, systemic juvenile idiopathic arthritis, rheumatoid arthritis, acute gouty arthritis, chronic gouty arthritis, urticaria, vasculitis, type 1 diabetes, type 2 diabetes, ankylosing spondylitis, recurrent multifocal osteomyelitis, relapsing polychondritis, cyropyrin-associated periodic syndrome (CAPS), Behçet's disease, familial mediterranean fever, chronic obstructive pulmonary disease, polymyalgia rheumatic, NALP3-mutations, pyoderma gangrenosum, chronic idiopathic urticarial, osteoarthritis, wet age-related macular degeneration, dry eye syndrome, pustular psoriasis, synovitis-acne-pustulosis-hyperostosis-osteitis syndrome, macrophage activation syndrome, periodic fever, adenitis, pharyngitis, aphthous ulcer syndrome, adult-onset Still's disease, mevalonate kinase deficiency, atherosclerosis, TNF-receptor associated periodic syndrome (TRAPS), acne vulgaris and/or acne inversa.

The term "CAPS" or cryopyrin-associated periodic syndrome is to be understood to include each of familial cold autoinflammatory syndrome (FCAS), Muckle-Wells syndrome (MWS) and neonatal-onset multisystem inflammatory disease, also known as chronic infantile neurological, cutaneous and articular (CINCA) syndrome.

The pharmaceutical composition may be applied by different administration routes. Administration can be conducted, for example, but not limited to, parenterally, e.g., intramuscularly, subcutaneously, intravenously as a bolus or by continuous infusion, intraarticularly, intrasynovially, intracerebrally, intracerebrospinally, intrathecally, epidurally, or intraperitoneally; orally; rectally; locally, urogenitally; topically, e.g., to the skin or the eye; Intravitreally; intravenously; intraocularly; oticly; intranasally; by inhalation; dermally such as intradermally, subcutaneously or transdermally; sublingually; buccally, for example. Preferred are the topical, rectal, local, intranasal, intravenous and/or intradermal routes of administration.

The antibody of the instant invention, the binding member, the nucleic acid sequences, the vector or host cell can be combined with one or more further therapeutically effective compound. Said compound may either be capable of disrupting signalling via the IL-1 receptor, or alternatively inhibit one or more different targets such as, e.g., other mediators of inflammatory responses. Such compound(s) can be administered simultaneously or sequentially.

For therapeutic applications, the antibody may also be radiolabelled or linked to a toxin or linked to another effector function as described above.

Diagnostic Applications and/or Detection Purposes

The antibody of the instant invention may be used for detection or diagnostic purposes in vivo and/or in vitro. For example, a wide range of immunoassays involving antibodies for detecting the expression in specific cells or tissues are known to the skilled person. Likewise, any binding member, the nucleic acid sequence, the vector and/or the host cell described previously can be used accordingly as detailed in this section.

For such applications the antibody, binding member, the nucleic acid sequence, the vector or the host cell disclosed herein may be either labelled or unlabelled. E.g., an unlabelled antibody may be used and detected by a secondary antibody recognizing an epitope on the antibody described herein.

In another embodiment the antibody, binding member, nucleic acid sequence, vector and/or host cell is conjugated with one or more substances which can be recognized by a detector substance(s), e.g., the antibody being conjugated with biotin which can be detected by streptavidin. Likewise, the nucleic acids and/or vectors disclosed herein can be used for detection or diagnostic purposes, e.g., by using labelled fragments thereof as probes in hybridization assays.

In certain embodiments, any of the molecules provided herein, in particular the antibody, is useful for detecting the presence of IL-1 beta, preferably including full-length IL-1 beta, fragments thereof and/or precursors thereof, in a sample, preferably biological sample. The term "detecting" encompasses quantitative and/or qualitative detection. In certain embodiments a biological sample comprises a cell or tissue from human patients. Non limiting examples of biological samples include blood, urine, cerebrospinal fluid, biopsy, lymph and/or non-blood tissues.

In certain embodiments, the method comprises contacting the biological sample with an anti-IL-1 beta antibody as described herein under conditions permissive for binding of the antibody to IL-1 beta, if present, and detecting whether a complex is formed between the antibody and IL-1 beta. Such method may be an in vitro or in vivo method. In one embodiment an anti-IL-1 beta antibody is used to select subjects eligible for therapy with the antibody described herein, e.g., where IL-1 beta is a biomarker for selection of patients. Similarly, instead of the antibody, such method may involve the use of the binding member above or a T-body described herein.

In another aspect, the antibody is used in cosmetic applications, e.g., for improving the aesthetic appearance of skin.

In a further aspect, a kit is provided comprising the antibody, a packaged combination of reagents with instructions for performing the detection or diagnostic assay. The reagents are typically provided in predetermined amounts of dry powders, usually lyophilized, including excipients which after dissolution will provide a reagent solution having the appropriate concentration. Other additives such as stabilizers and/or buffers may also be included. If the antibody is labelled with an enzyme, the kit will typically include the according substrates and cofactors. Likewise, any binding member, the nucleic acid sequence, the vector and/or the host cell described previously can be used accordingly as detailed in this section.

---

Sequence listing

The sequences disclosed herein are:
SEQ ID No: 1- VH CDR1
FSLSSAAMA

SEQ ID No: 2- VH CDR2
IIYDSASTYYASWAKG

SEQ ID No: 3- VH CDR3
ERAIFSGDFVL

Sequence listing

SEQ ID No: 4- VL CDR1
QASQSIDNWLS

SEQ ID No: 5- VL CDR2
RASTLAS

SEQ ID No: 6- VL CDR3
QNTGGGVSIA

SEQ ID No: 7- VH
EVQLVESGGGLVQPGGSLRLSCTASGFSLSSAAMAWVRQAPGKGLEWVGI
IYDSASTYYASWAKGRFTISRDTSKNTVYLQIfNSLRAEDTAVYYCARE
RAIFSGDFVLWGQGTLVTVSS

SEQ ID No: 8- VL
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLG

SEQ ID No: 9- linker
GGGGSGGGGSGGGGSGGGGS

SEQ ID No: 10- DLX2323
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERAIFSGDFVLWGQGTLVTVSS

SEQ ID No: 11- CDR variant of VH CDR1
FSLSXXAMA

SEQ ID No: 12- CDR variant of VH CDR2
IIXXSASTXYASWAKG

SEQ ID No: 13- CDR variant of VH CDR3
EXXXXXXXXX

SEQ ID No: 14- CDR variant of VL CDR1
QASQSIXXXLS

SEQ ID No: 15- CDR variant of VL CDR2
XASXLAS

SEQ ID No: 16- CDR variant of VL CDR3
QNXGXXXXIA

SEQ ID No: 17- DNA sequence of DLX2323
GAAATTGTTATGACCCAGAGCCCGAGCACCCTGAGCGCAAGCGTTGGTGA
TCGTGTGATTATTACCTGTCAGGCAAGCCAGAGCATTGATAATTGGCTGA
GCTGGTATCAGCAGAAACCGGGTAAAGCACCGAAACTGCTGATTTATCGT
GCAAGCACCCTGGCAAGCGGTGTTCCGAGCCGTTTTAGCGGTAGCGGTAG
TGGTGCAGAATTTACCCTGACCATTAGCAGCCTGCAGCCGGATGATTTTG
CAACCTATTATTGTCAGAATACCGGTGGTGGTGTTAGCATTGCATTTGGT
CAGGGCACCAAACTGACCGTTCTGGGTGGTGGCGGTGGATCCGGTGGGGG
TGGTAGCGGAGGTGGTGGTTCAGGCGGTGGTGGCAGCGAAGTTCAGCTGG
TTGAAAGTGGTGGTGGTCTGGTTCAGCCTGGTGGTAGCCTGCGTCTGAGC
TGTACCGCAAGCGGTTTTAGCCTGAGCAGCGCAGCAATGGCATGGGTTCG
TCAGGCACCTGGTAAAGGTCTGGAATGGGTTGGTATTATCTATGATAGCG
CAAGCACCTATTATGCAAGCTGGGCAAAAGGTCGTTTTACCATTAGCCGT
GATACCAGTAAAAATACCGTTTACCTGCAGATGAATAGTCTGCGTGCAGA
GGATACCGCAGTGTATTATTGTGCACGTGAACGTGCAATTTTCAGCGGTG
ATTTTGTTCTGTGGGGTCAGGGAACCCTGGTTACCGTTAGCAGC SEQ ID No.: 18- FR-L1 of FW1.4
EIVMTQSPSTLSASVGDRVIITC SEQ ID No.: 19- FR-L2 of FW1.4
WYQQKPGKAPKLLIY SEQ ID No.: 20- FR-L3 of FW1.4
GVPSRFSGSGSGAEFTLTISSLQPDDFATYYC SEQ ID No.: 21- FR-L4 of FW1.4
FGQGTKLTVLG SEQ ID No.: 22- FR-H1 of rFW1.4
EVQLVESGGGLVQPGGSLRLSCTASG SEQ ID No.: 23- FR-H2 of rFW1.4
WVRQAPGKGLEWVG SEQ ID No.: 24- FR-H3 of rFW1.4
RFTISRDTSKNTVYLQMNSLRAEDTAVYYCAR SEQ ID No.: 25- FR-H4 of rFW1.4
WGQGTLVTVSS SEQ ID No.: 26- FR-H1 of rFW1.4(V2)
EVQLVESGGGLVQPGGSLRLSCTVSG SEQ ID No.: 27- FR-H2 of rFW1.4(V2)
WVRQAPGKGLEWVG SEQ ID No.: 28- FR-H3 of rFW1.4(V2)
RFTISKDTSKNTVYLQMNSLRAEDTAVYYCAR SEQ ID No.: 29- FR-H4 of rFW1.4(V2)
WGQGTLVTVSS SEQ ID No.: 30- FR-H1 of rFW1.4-SST
EVQLVESGGGSVQPGGSLRLSCTASG SEQ ID No.: 31- FR-H2 of rFW1.4-SST
WVRQAPGKGLEWVG SEQ ID No.: 32- FR-H3 of rFW1.4-SST
RFTISRDTSKNTVYLQMNSLRAEDTASYYCAR SEQ ID No.: 33- FR-H4 of rFW1.4-SST
WGQGTTVTVSS SEQ ID No.: 34- CDR-L1_D32X
EIVMTQSPSTLSASVGDRVIITCQASQSIXNWLSWYQQKPGKAPKLLIYR
ASTLASGVPSRFSGSGSGAEFTLTISSLQPDDFATYYCQNTGGGVSIAFG

Sequence listing

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 35- CDR-L1_N33X
EIVMTQSPSTLSASVGDRVIITCQASQSIDXWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), serine (S),
threonine (T), valine (V), tryptophan (W) and
tyrosine (Y).

SEQ ID No.: 36- CDR-L1_W40X
EIVMTQSPSTLSASVGDRVIITCQASQSIDNXLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of glutamic acid (E), phenylalanine
(F), glycine (G), methionine (M), asparagine (N),
glutamine (Q), serine (S), tryptophan (W) and
tyrosine (Y).

SEQ ID No.: 37- CDR-L2_R58X
EIVMTQSPSTLSASVGDRVIITCQASQSIDNWLSWYQQKPGKAPKLLIYX

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), tryptophan (W) and tyrosine
(Y).

SEQ ID No.: 38- CDR-L2_T69X
EIVMTQSPSTLSASVGDRVIITCQASQSIDNWLSWYQQKPGKAPKLLIYR

ASXLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 39- CDR-L3_T109X
EIVMTQSPSTLSASVGDRVIITCQASQSIDNWLSWYQQKPGKAPKLLIYR

ASTLASGVPSRFSGSGSGAEFTLTISSLQPDDFATYYCQNXGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C),
isoleucine (I), asparagine (N), serine (S),
threonine (T) and valine (V).

SEQ ID No.: 40- CDR-L3_G111X
EIVMTQSPSTLSASVGDRVIITCQASQSIDNWLSWYQQKPGKAPKLLIYR

ASTLASGVPSRFSGSGSGAEFTLTISSLQPDDFATYYCQNTGXGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), glycine (G), proline
(P) and serine (S).

SEQ ID No: 41- CDR-L3_G112X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGXVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 42- CDR-L3_V135X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGXSIAFG

Sequence listing

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No: 43- CDR-L3_S136X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVXIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I),
leucine (L), methionine (M), asparagine (N),
proline (P), glutamine (Q), arginine (R), serine
(S), threonine (T), valine (V), tryptophan (W) and
tyrosine (Y).

SEQ ID No.: 44- CDR-H1_S33X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSXAAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 45- CDR-H1_A39X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSXAMAWVRQAPGKGLEWVGIIYDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
glutamine (Q), arginine (R), serine (S),
threonine (T), valine (V), tryptophan (W) and
tyrosine (Y).

SEQ ID No.: 46- CDR-H2_Y59X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIXDSASTYYASWAKGRFTISR

DTSKNTVYLQMNSLRAEDTAVYYCARERAIFSGDFVLWGQGTLVTVSS
Preferably, X is selected from the group
consisting of alanine (A), cysteine (C), glycine
(G), methionine (M) and tyrosine (Y).

SEQ ID No: 47- CDR-H2_D60X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYXSASTYYASWAKGRFTISR

DTSKNTVYLQMNSLRAEDTAVYYCARERAIFSGDFVLWGQGTLVTVSS
Preferably, X is selected from the group
consisting of aspartic acid (D), asparagine (N)
and proline (P).

SEQ ID No.: 48- CDR-H2_Y69X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTXYASWAKGRFTISR

DTSKNTVYLQMNSLRAEDTAVYYCARERAIFSGDFVLWGQGTLVTVSS
Preferably, X is selected from the group
consisting of alanine (A), aspartic acid (D),
glutamic acid (E), glycine (G), phenylalanine (F),
histidine (H), isoleucine (I), lysine (K), leucine
(L), methionine (M), proline (P), asparagine (N),
serine (S), threonine (T), tryptophan (W) and
tyrosine (Y).

SEQ ID No: 49- CDR-H3_R110X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCAREXAIFSGDFVLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
glutamine (Q), arginine (R), serine (S),
threonine (T), valine (V), tryptophan (W) and
tyrosine (Y).

SEQ ID No.: 50- CDR-H3_A111X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

Sequence listing

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERXIFSGDFVLWGQGTLVTVSS
Preferably, X is selected from the group
consisting of alanine (A), cysteine (C), aspartic
acid (D), phenylalanine (F), glycine (G),
histidine (H), isoleucine (I), lysine (K),
methionine (M), asparagine (N), proline (P),
glutamine (Q), arginine (R), serine (S), threonine
(T), valine (V), tryptophan (W) and tyrosine (Y).

SEQ ID No.: 51- CDR-H3_I112X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAXFSGDFVLWGQGTLVTVSS
Preferably, X is selected from the group
consisting of alanine (A), cysteine (C),
phenylalanine (F), histidine (H), isoleucine (I),
leucine (L), methionine (M), asparagine (N),
glutamine (Q), serine (S), threonine (T), valine
(V) and tyrosine (Y).

SEQ ID No.: 52- CDR-H3_F113X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIXSGDFVLWGQGTLVTVSS
Preferably, X is selected from the group
consisting of phenylalanine (F) and isoleucine
(I).

SEQ ID No.: 53- CDR-H3_S114X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERA1FXGDFVLWGQGTLVTVSS
Preferably, X is selected from the group
consisting of alanine (A), cysteine (C),
glutamic acid (E), glycine (G), serine (S),
threonine (T) and valine (V).

SEQ ID No.: 54- CDR-H3_G115X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSXDFVLWGQGTLVTVSS
Preferably, X is selected from the group
consisting of alanine (A), glycine (G),
methionine (M) and asparagine (N).

SEQ ID No.: 55- CDR-H3_D135X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGXFVLWGQGTLVTVSS
Preferably, X is selected from the group
consisting of alanine (A), aspartic acid (D),
glutamic acid (E), histidine (H), asparagine (N),
serine (S) and threonine (T).

SEQ ID No: 56- CDR-H3_F136X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDXVLWGQGTLVTVSS
Preferably, X is selected from the group
consisting of alanine (A), cysteine (C),
phenylalanine (F), glycine (G), histidine (H),
isoleucine (I), leucine (L), methionine (M),
asparagine (N), glutamine (Q), serine (S),
threonine (T), valine (V), tryptophan (W) and
tyrosine (Y).

SEQ ID No.: 57- CDR-H3_V137X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFXLWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 58- CDR-H3_L138X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERAIFSGDFVXWGQGTLVTVSS
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No.: 59- DLX2464
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLGGGGSGGGGSGGGGSGGGGSEVQLVESGGGLVQPGGSLRLS

CTASGFSLSSAAMAWVRQAPGKGLEWVGIIYDSASTYYASWAKGRFTISR

DTSKNTVYLQMNSLRAEDTAVYYCARERQIFSGDMAGWGQGTLVTVSS

Sequence listing

SEQ ID No.: 60- DLX2465
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERNIFSGDMDLWGQGTLVTVSS

SEQ ID No.: 61- DLX2466
EIVMTQSPSTLSASVGDRVIITCQASQSIGKYLSWYQQKPGKAPKLLIYR
ASTLASGVPSRFSGSGSGAEFTLTISSLQPDDFATYYCQNAGGGVSIAFG
QGTKLTVLGGGGSGGGGSGGGGSGGGGSEVQLVESGGGLVQPGGSLRLS
CTASGFSLSSDAMAWVRQAPGKGLEWVGIIYDSASTYYASWAKGRFTISR
DTSKNTVYLQMNSLRAEDTAVYYCARERNIFSGDMAGWGQGTLVTVSS

SEQ ID No.: 62- DLX2467
EIVMTQSPSTLSASVGDRVIITCQASQSIHNWLSWYQQKPGKAPKLLIYR
ASNLASGVPSRFSGSGSGAEFTLTISSLQPDDFATYYCQNTGGGSSIAFG
QGTKLTVLGGGGSGGGGSGGGGSGGGGSEVQLVESGGGLVQPGGSLRLS
CTASGFSLSRAAMAWVRQAPGKGLEWVGIIYDSASTYYASWAKGRFTISR
DTSKNTVYLQMNSLRAEDTAVYYCARERMIFSGDFVLWGQGTLVTVSS

SEQ ID No.: 63- DLX2468
EIVMTQSPSTLSASVGDRVIITCQASQSIGNYLSWYQQKPGKAPKLLIYR
ASTLASGVPSRFSGSGSGAEFTLTISSLQPDDFATYYCQNAGGGTSIAFG
QGTKLTVLGGGGSGGGGSGGGGSGGGGSEVQLVESGGGLVQPGGSLRLS
CTASGFSLSSSAMAWVRQAPGKGLEWVGIIYDSASTYYASWAKGRFTISR
DTSKNTVYLQMNSLRAEDTAVYYCARERNIFSGDMVLWGQGTLVTVSS

SEQ ID No.: 64- DLX2475
EIVMTQSPSTLSASVGDRVIITCQASQSIDKWLSWYQQKPGKAPKLLIYQ
ASTLASGVPSRFSGSGSGAEFTLTISSLQPDDFATYYCQNTGGGVHIAFG
QGTKLTVLGGGGSGGGGSGGGGSGGGGSEVQLVESGGGLVQPGGSLRLS
CTASGFSLSSYAMAWVRQAPGKGLEWVGIIYDSASTYYASWAKGRFTISR
DTSKNTVYLQMNSLRAEDTAVYYCARERAIFSGDFKLWGQGTLVTVSS

SEQ ID No.: 65- DLX2476
EIVMTQSPSTLSASVGDRVIITCQASQSISSWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERDIFSGDFVGWGQGTLVTVSS

SEQ ID No.: 66- DLX2480
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGINIAFG
QGTKLTVLGGGGSGGGGSGGGGSGGGGSEVQLVESGGGLVQPGGSLRLS
CTASGFSLSDAAMAWVRQAPGKGLEWVGIIYDSASTYYASWAKGRFTISR
DTSKNTVYLQMNSLRAEDTAVYYCARERQIFSGDFVLWGQGTLVTVSS

SEQ ID No: 67- DLX2543
EIVMTQSPSTLSASVGDRVTITCQASQSISSWLSWYQQKPGKAPKLLIYK
ASTLASGVPSRFSGSGSGTEFTLTISSLQPDDFATYYCQNAGGGVSIAFG
QGTKLTVLGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERAIFSGDFVLWGQGTLVTVSS

SEQ ID No.: 68- DLX2529
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERAIFSGDFVLWGQGTLVTVSS

SEQ ID No.: 69- DLX2547
ADIVMTQSPSTLSASVGDRVTITCQASQSISSYLSWYQQKPGKAPKLLIY
RASTLASGVPSRFSGSGSGAEFTLTISSLQPDDFATYYCQNTGGGINIAF
GQGTKLEIKRGGGGSGGGGSGGGGSGGGGSEVQLVESGGGLVQPGGSLRL
SCTASGFSLSSAAMAWVRQAPGKGLEWVGIIYDSASTYYASWAKGRFTIS
RDTSKNTVYLQMNSLRAEDTAVYYCARERAIFSGDFVLWGQGTLVTVSS

SEQ ID No.: 70- DLX2528
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLGGGGSGGGGSGGGGSGGGGSEVQLVESGGGLVQPGGSLRLS
CTASGFSLSSAAMAWVRQAPGKGLEWVGIIYDSASTYYASWAKGRFTISR
DTSKNTVYLQMNSLRAEDTAVYYCARERAIFSGDFVLWGQGTLVTVSS

SEQ ID No.: 71- DLX2585
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTVSGFSLSSYAMSWVRQAPGKGLEWVGIIYDSASTYYASWAKGRFTISK
DTSKNTVYLQMNSLRAEDTAVYYCARERAIFSGDFDYWGQGTLVTVSS

SEQ ID No.: 72- DLX2545
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTASGFSLSSAAMAWVRQAPGKGLEWIGIIYDSASTYYASWAKGRFTISR
DTSKNTLYLQMNSLRAEDTAVYFCARERNIFSGDMVLWGQGTTVTVSS

SEQ ID No.: 73- DLX2531
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGNVQPGGSLRLS
CTASGFSLSNSAMAWVRQAPGKGLEWVGIIYDSASTYYASWAKGRFTISR
DNSKNTVYLQMNSLRAEDTATYYCARERAIFSGDFALWGQGTLVTVSS

Sequence listing

SEQ ID No.: 74- DLX2586
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTVYLQMNSLRAEDTAVYFCARERQIFSGDMDGWGQGTLVTVSS

SEQ ID No.: 75- DLX2530
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGNVQPGGSLRLS
CTASGFSLSDAAMAWVRQAPGKGLEWVGIIYDSASTFYASWAKGRFTISR
DNSKNTLYLQMNSLRAEDTATYYCARERNIFSGDMALWGQGTTVTVSS

SEQ ID No.: 76- DLX2548
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTLYLQMNSLRAEDTAVYFCARERQIFSGDMDGWGQGTTVTVSS

SEQ ID No.: 77- DLX2676
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLGGGGSGGGGSGGGGSGGGGSEVQLVESGGGNVQPGGSLRLS
CTASGFSLSDAAMAWVRQAPGKGLEWVGIIYDSASTFYASWAKGRFTISR
DNSKNTLYLQMNSLRAEDTATYYCARERNIFSGDMALWGQGTTVTVSS

SEQ ID No.: 78- DLX2677
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLGGGGSGGGGSGGGGSGGGGSEVQLVESGGGNVQPGGSLRLS
CTASGFSLSNSAMAWVRQAPGKGLEWVGIIYDSASTYYASWAKGRFTISR
DNSKNTVYLQMNSLRAEDTATYYCARERAIFSGDFALWGQGTLVTVSS

SEQ ID No.: 79- DLX2678
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTVYLQMNSLRAEDTAVYFCARERQIFSGDMDGWGQGTLVTVSS

SEQ ID No.: 80- DLX2679
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTVYLQMNSLRAEDTAVYYCARERAIFSGDFDYWGQGTLVTVSS

SEQ ID No.: 81- DLX2680
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLGGGGSGGGGSGGGGSGGGGSEVQLVESGGGNVQPGGSLRLS
CTASGFSLSDAAMAWVRQAPGKGLEWVGIIYDSASTFYASWAKGRFTISR
DNSKNTLYLQMNSLRAEDTATYYCARERNIFSGDMALWGQGTTVTVSS

SEQ ID No.: 82- DLX2681
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLGGGGSGGGGSGGGGSGGGGSEVQLVESGGGNVQPGGSLRLS
CTASGFSLSNSAMAWVRQAPGKGLEWVGIIYDSASTYYASWAKGRFTISR
DNSKNTVYLQMNSLRAEDTATYYCARERAIFSGDFALWGQGTLVTVSS

SEQ ID No.: 83- DLX2682
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTLYLQMNSLRAEDTAVYFCARERQIFSGDMDGWGQGTTVTVSS

SEQ ID No.: 84- DLX2683
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTVYLQMNSLRAEDTAVYYCARERAIFSGDFDYWGQGTLVTVSS

SEQ ID No.: 85- DLX2684
EIVMTQSPSTLSASVGDRVTITCQASQSISSWLSWYQQKPGKAPKLLIYK
ASTLASGVPSRFSGSGSGTEFTLTISSLQPDDFATYYCQNAGGGVSIAFG
QGTKLTVLGGGGSGGGGSGGGGSGGGGSEVQLVESGGGNVQPGGSLRLS
CTASGFSLSDAAMAWVRQAPGKGLEWVGIIYDSASTFYASWAKGRFTISR
DNSKNTLYLQMNSLRAEDTATYYCARERNIFSGDMALWGQGTTVTVSS

SEQ ID No.: 86- DLX2685
EIVMTQSPSTLSASVGDRVTITCQASQSISSWLSWYQQKPGKAPKLLIYK
ASTLASGVPSRFSGSGSGTEFTLTISSLQPDDFATYYCQNAGGGVSIAFG
QGTKLTVLGGGGSGGGGSGGGGSGGGGSEVQLVESGGGNVQPGGSLRLS
CTASGFSLSNSAMAWVRQAPGKGLEWVGIIYDSASTYYASWAKGRFTISR
DNSKNTLYLQMNSLRAEDTATYYCARERAIFSGDFALWGQGTLVTVSS

SEQ ID No.: 87- DLX2686
EIVMTQSPSTLSASVGDRVTITCQASOSISSWLSWYQQKPGKAPKLLIYK
ASTLASGVPSRFSGSGSGTEFTLTISSLQPDDFATYYCQNAGGGVSIAFG
QGTKLTVLGGGGSGGGGSGGGGSGGGGSEVQLVESGGGLVQPGGSLRLS
CTVSGFSLSSYAMSWVRQAPGKGLEWIGIIYDSASTYYASWAKGRFTISK
DTSKNTLYLQMNSLRAEDTAVYFCARERQIFSGDMDGWGQGTTVTVSS

Sequence listing

SEQ ID No.: 88- DLX2687
EIVMTQSPSTLSASVGDRVTITCQASQSISSWLSWYQQKPGKAPKLLIYK
ASTLASGVPSRFSGSGSGTEFTLTISSLQPDDFATYYCQNAGGGVSIAFG
QGTKLTVLGGGGSGGGGSGGGGSGGGGSEVQLVESGGGLVQPGGSLRLS
CTVSGFSLSSYAMSWVRQAPGKGLEWVGIIYDSASTYYASWAKGRFTISK
DTSKNTVYLQMNSLRAEDTAVYYCARERAIFSGDFDYWGQGTLVTVSS

SEQ ID No.: 89- DLX2689
ADIVMTQSPSTLSASVGDRVTITCQASQSISSYLSWYQQKPGKAPKLLIY
KASTLASGVPSRFSGSGSGTDFTLTISSLQPEDFATYYCQNAGGGINIAF
GQGTKVEEKRGGGGSGGGGSGGGGSGGGGSEVQLVESGGGNVQPGGSLRL
SCTASGFSLSNSAMAWVRQAPGKGLEWVGIIYDSASTYYASWAKGRFTIS
RDNSKNTVYLQMNSLRAEDTATYYCARERAIFSGDFALWGQGTLVTVSS

SEQ ID No.: 90- DLX2690
ADIVMTQSPSTLSASVGDRVTITCQASQSISSYLSWYQQKPGKAPKLLIY
KASTLASGVPSRFSGSGSGTDFTLTISSLQPEDFATYYCQNAGGGINIAF
GQGTKVEIKRGGGGSGGGGSGGGGSGGGGSEVQLVESGGGLVQPGGSLRL
SCTVSGFSLSSYAMSWVRQAPGKGLEWIGIIYDSASTYYASWAKGRFTIS
KDTSKNTLYLQMNSLRAEDTAVYFCARERQIFSGDMDGWGQGTTVTVSS

SEQ ID No.: 91- DLX2691
ADIVMTQSPSTLSASVGDRVTITCQASQSISSYLSWYQQKPGKAPKLLIY
KASTLASGVPSRFSGSGSGTDFTLTISSLQPEDFATYYCQNAGGGINIAF
GQGTKVEIKRGGGGSGGGGSGGGGSGGGGSEVQLVESGGGLVQPGGSLRL
SCTVSGFSLSSYAMSWVRQAPGKGLEWVGIIYDSASTYYASWAKGRFTIS
KDTSKNTVYLQMNSLRAEDTAVYYCARERAIFSGDFDYWGQGTLVTVSS

SEQ ID No.: 92- DLX2692
ADIVMTQSPSTLSASVGDRVTITCQASQSISSYLSWYQQKPGKAPKLLIY
RASTLASGVPSRFSGSGSGAEFTLTISSLQPDDFATYYCQNTGGGIN1AF
GQGTKLEIKRGGGGSGGGGSGGGGSGGGGSEVQLVESGGGNVQPGGSLRL
SCTASGFSLSDAAMAWVRQAPGKGLEWVGIIYDSASTFYASWAKGRFTIS
RDNSKNTLYLQMNSLRAEDTATYYCARERNIFSGDMALWGQGTTVTVSS

SEQ ID No.: 93- DLX2693
ADIVMTQSPSTLSASVGDRVTITCQASQSISSYLSWYQQKPGKAPKLLIY
RASTLASGVPSRFSGSGSGAEFTLTISSLQPDDFATYYCQNTGGGINIAF
GQGTKLEIKRGGGGSGGGGSGGGGSGGGGSEVQLVESGGGNVQPGGSLRL
SCTASGFSLSNSAMAWVRQAPGKGLEWVGIIYDSASTYYASWAKGRFTIS
RDNSKNTVYLQMNSLRAEDTATYYCARERAIFSGDFALWGQGTLVTVSS

SEQ ID No.: 94- DLX2694
ADIVMTQSPSTLSASVGDRVTITCQASQSISSYLSWYQQKPGKAPKLLIY
RASTLASGVPSRFSGSGSGAEFTLTISSLQPDDFATYYCQNTGGGINIAF
GQGTKLEIKRGGGGSGGGGSGGGGSGGGGSEVQLVESGGGLVQPGGSLRL
SCTVSGFSLSSYAMSWVRQAPGKGLEWIGIIYDSASTYYASWAKGRFTIS
KDTSKNTLYLQMNSLRAEDTAVYFCARERQIFSGDMDGWGQGTTVTVSS

SEQ ID No: 95- DLX2695
ADIVMTQSPSTLSASVGDRVTITCQASQSISSYLSWYQQKPGKAPKLLIY
RASTLASGVPSRFSGSGSGAEFTLTISSLQPDDFATYYCQNTGGGINIAF
GQGTKLEIKRGGGGSGGGGSGGGGSGGGGSEVQLVESGGGLVQPGGSLRL
SCTVSGFSLSSYAMSWVRQAPGKGLEWVGIIYDSASTYYASWAKGRFTIS
KDTSKNTVYLQMNSLRAEDTAVYYCARERAIFSGDFDYWGQGTLVTVSS

SEQ ID No.: 96- VL CDR-L1_D32X
EIVMTQSPSTLSASVGDRVIITCQASQSIXNWLSWYQQKPGKAPKLLIYR
ASTLASGVPSRFSGSGSGAEFTLTISSLQPDDFATYYCQNTGGGVSIAFG
QGTKLTVLG
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), valine (V), tryptophan (W) and
tyrosine (Y).

SEQ ID No: 97- VL CDR-L1_N33X
EIVMTQSPSTLSASVGDRVIITCQASQSIDXWLSWYQQKPGKAPKLLIYR
ASTLASGVPSRFSGSGSGAEFTLTISSLQPDDFATYYCQNTGGGVSIAFG
QGTKLTVLG
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), serine (S),
threonine (T), valine (V), tryptophan (W) and
tyrosine (Y).

SEQ ID No: 98- VL CDR-L1_W40X
EIVMTQSPSTLSASVGDRVIITCQASQSIDNXLSWYQQKPGKAPKLLIYR
ASTLASGVPSRFSGSGSGAEFTLTISSLQPDDFATYYCQNTGGGVSIAFG
QGTKLTVLG
Preferably, X is selected from the group
consisting of glutamic acid (E), phenylalanine
(F), glycine (G), methionine (M), asparagine (N),
glutamine (Q), serine (S), tryptophan (W) and
tyrosine (Y).

SEQ ID No.: 99- VL CDR-L2_R58X
EIVMTQSPSTLSASVGDRVIITCQASQSIDNWLSWYQQKPGKAPKLLIYX
ASTLASGVPSRFSGSGSGAEFTLTISSLQPDDFATYYCQNTGGGVSIAFG
QGTKLTVLG
Preferably, X is selected from the group
consisting of alanine (A), cysteine (C), aspartic
acid (D), glutamic acid (E), phenylalanine (F),
glycine (G), histidine (H), isoleucine (I), lysine
(K), leucine (L), methionine (M), asparagine (N),
proline (P), glutamine (Q), arginine (R), serine
(S), threonine (T), tryptophan (W) and tyrosine
(Y).

SEQ ID No.: 100- VL CDR-L2_T69X
EIVMTQSPSTLSASVGDRVIITCQASQSIDNWLSWYQQKPGKAPKLLIYR
ASXLASGVPSRFSGSGSGAEFTLTISSLQPDDFATYYCQNTGGGVSIAFG
QGTKLTVLG

| Sequence listing |
|---|
| Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).
SEQ ID No.: 101- VL CDR-L3_T109X
EIVMTQSPSTLSASVGDRVIITCQASQSIDNWLSWYQQKPGKAPKLLIYR

ASTLASGVPSRFSGSGSGAEFTLTISSLQPDDFATYYCQNXGGGVSIAFG

QGTKLTVLG
Preferably, X is selected from the group consisting of alanine (A), cysteine (C), isoleucine (I), asparagine (N), serine (S), threonine (T) and valine (V).
SEQ ID No.: 102- VL CDR-L3_G111X
EIVMTQSPSTLSASVGDRVIITCQASQSIDNWLSWYQQKPGKAPKLLIYR

ASTLASGVPSRFSGSGSGAEFTLTISSLQPDDFATYYCQNTGXGVSIAFG

QGTKLTVLG
Preferably, X is selected from the group consisting of alanine (A), glycine (G), proline (P) and serine (S).
SEQ ID No.: 103- VL CDR-L3_G112X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGXVSIAFG

QGTKLTVLG
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).
SEQ ID No.: 104- VL CDR-L3_V135X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGXSIAFG

QGTKLTVLG
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).
SEQ ID No.: 105- VL CDR-L3_S136X
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVXIAFG

QGTKLTVLG
Preferably, X is selected from the group consisting of alanine (A), cysteine (C), aspartic acid (D), glutamic acid (E), phenylalanine (F), glycine (G), histidine (H), isoleucine (I), leucine (L), methionine (M), asparagine (N), proline (P), glutamine (Q), arginine (R), serine (S), threonine (T), valine (V), tryptophan (W) and tyrosine (Y).
SEQ ID No.: 106- VH CDR-H1_S33X
EVQLVESGGGLVQPGGSLRLSCTASGFSLSXAAMAWVRQAPGKGLEWVGI

IYDSASTYYASWAKGRFTISRDTSKNTVYLQMNSLRAEDTAVYYCARERA

IFSGDFVLWGQGTLVTVSS
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).
SEQ ID No.: 107- VH CDR-H1_A39X
EVQLVESGGGLVQPGGSLRLSCTASGFSLSSXAMAWVRQAPGKGLEWVGI

IYDSASTYYASWAKGRFTISRDTSKNTVYLQMNSLRAEDTAVYYCARERA

IFSGDFVLWGQGTLVTVSS
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).
SEQ ID No.: 108- VH CDR-H2_Y59X
EVQLVESGGGLVQPGGSLRLSCTASGFSLSSAAMAWVRQAPGKGLEWVGI

IXDSASTYYASWAKGRFTISRDTSKNTVYLQMNSLRAEDTAVYYCARERA

IFSGDFVLWGQGTLVTVSS
Preferably, X is selected from the group consisting of alanine (A), cysteine (C), glycine (G), methionine (M) and tyrosine (Y).
SEQ ID No: 109- VH CDR-H2_D60X
EVQLVESGGGLVQPGGSLRLSCTASGFSLSSAAMAWVRQAPGKGLEWVGI

IYXSASTYYASWAKGRFTISRDTSKNTVYLQMNSLRAEDTAVYYCARERA

IFSGDFVLWGQGTLVTVSS
Preferably, X is selected from the group consisting of aspartic acid (D), asparagine (N) and proline (P).
SEQ ID No.: 110- VH CDR-H2_Y69X
EVQLVESGGGLVQPGGSLRLSCTASGFSLSSAAMAWVRQAPGKGLEWVGI

IYDSASTXYASWAKGRFTISRDTSKNTVYLQMNSLRAEDTAVYYCARERA

IFSGDFVLWGQGTLVTVSS
Preferably, X is selected from the group consisting of alanine (A), aspartic acid (D), glutamic acid (E), glycine (G), phenylalanine (F), histidine (H), isoleucine (I), lysine (K), leucine (L), methionine (M), proline (P), asparagine (N), serine (S), threonine (T), tryptophan (W) and tyrosine (Y).
SEQ ID No.: 111- VH CDR-H3_R110X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCAREXA

IFSGDFVLWGQGTLVTVSS
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), glutamine (Q), arginine (R), serine (S), threonine (T), valine (V), tryptophan (W) and tyrosine (Y). |

Sequence listing

SEQ ID No.: 112- VH CDR-H3_A111X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERX

IFSGDFVLWGQGTLVTVSS
Preferably, X is selected from the group consisting of alanine (A), cysteine (C), aspartic acid (D), phenylalanine (F), glycine (G), histidine (H), isoleucine (I), lysine (K), methionine (M), asparagine (N), proline (P), glutamine (Q), arginine (R), serine (S), threonine (T), valine (V), tryptophan (W) and tyrosine (Y).

SEQ ID No.: 113- VH CDR-H3_I112X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

XFSGDFVLWGQGTLVTVSS
Preferably, X is selected from the group consisting of alanine (A), cysteine (C), phenylalanine (F), histidine (H), isoleucine (I), leucine (L), methionine (M), asparagine (N), glutamine (Q), serine (S), threonine (T), valine (V) and tyrosine (Y).

SEQ ID No.: 114- VH CDR-H3_F113X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IXSGDFVLWGQGTLVTVSS
Preferably, X is selected from the group consisting of phenylalanine (F) and isoleucine (I).

SEQ ID No.: 115- VH CDR-H3_S114X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFXGDFVLWGQGTLVTVSS
Preferably, X is selected from the group consisting of alanine (A), cysteine (C), glutamic acid (E), glycine (G), serine (S), threonine (T) and valine (V).

SEQ ID No.: 116- VH CDR-H3_G115X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFSXDFVLWGQGTLVTVSS
Preferably, X is selected from the group consisting of alanine (A), glycine (G), methionine (M) and asparagine (N).

SEQ ID No.: 117- VH CDR-H3_D135X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFSGXFVLWGQGTLVTVSS
Preferably, X is selected from the group consisting of alanine (A), aspartic acid (D), glutamic acid (E), histidine (H), asparagine (N), serine (S) and threonine (T).

SEQ ID No.: 118- VH CDR-H3_F136X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFSGDXVLWGQGTLVTVSS
Preferably, X is selected from the group consisting of alanine (A), cysteine (C), phenylalanine (F), glycine (G), histidine (H), isoleucine (I), leucine (L), methionine (M), asparagine (N), glutamine (Q), serine (S), threonine (T), valine (V), tryptophan (W) and tyrosine (Y).

SEQ ID No.: 119- VH CDR-H3_V137X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFSGDFXLWGQGTLVTVSS
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).

SEQ ID No.: 120- VH CDR-H3_L138X
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERA

IFSGDFVXWGQGTLVTVSS
Preferably, X is selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W) and tyrosine (Y).

SEQ ID No.: 121- VH DLX2464
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERQ

IFSGDMAGWGQGTLVTVSS

SEQ ID No.: 122- VH DLX2465
EVQLVESGGGLVQPGGSLRLSCTASGFSLSSAAMAWVRQAPGKGLEWVGI

IYDSASTYYASWAKGRFTISRDTSKNTVYLQMNSLRAEDTAVYYCARERN

IFSGDNIDLWGQGTLVTVSS

SEQ ID No.: 123- VL DLX2466
EIVMTQSPSTLSASVGDRVIITCQASQSIGKYLSWYQQKPGKAPKLLIYR

ASTLASGVPSRFSGSGSGAEFTLTISSLQPDDFATYYCQNAGGGVSIAFG

QGTKLTVLG

SEQ ID No.: 124- VH DLX2466
EVQLVESGGGLVQPGGSLRLSCTASGFSLSSDAMAWVRQAPGKGLEWVGI

IYDSASTYYASWAKGRFTISRDTSKNTVYLQMNSLRAEDTAVYYCARERN

IFSGDMAGWGQGTLVTVSS

Sequence listing

SEQ ID No.: 125- VL DLX2467
EIVMTQSPSTLSASVGDRVIITCQASQSIHNWLSWYQQKPGKAPKLLIYR
ASNLASGVPSRFSGSGSGAEFTLTISSLQPDDFATYYCQNTGGGSSIAFG
QGTKLTVLG

SEQ ID No.: 126- VH DLX2467
EVQLVESGGGLVQPGGSLRLSCTASGFSLSRAAMAWVRQAPGKGLEWVGI
IYDSASTYYASWAKGRFTISRDTSKNTVYLQMNSLRAEDTAVYYCARERM
IFSGDFVLWGQGTLVTVSS

SEQ ID No.: 127- VL DLX2468
EIVMTQSPSTLSASVGDRVIITCQASQSIGNYLSWYQQKPGKAPKLLIYR
ASTLASGVPSRFSGSGSGAEFTLTISSLQPDDFATYYCQNAGGGTSIAFG
QGTKLTVLG

SEQ ID No.: 128- VH DLX2468
EVQLVESGGGLVQPGGSLRLSCTASGFSLSSSAMAWVRQAPGKGLEWVGI
IYDSASTYYASWAKGRFTISRDTSKNTVYLQMNSLRAEDTAVYYCARERN
IFSGDMVLWGQGTLVTVSS

SEQ ID No.: 129- VL DLX2475
EIVMTQSPSTLSASVGDRVIITCQASQSIDKWLSWYQQKPGKAPKLLIYQ
ASTLASGVPSRFSGSGSGAEFTLTISSLQPDDFATYYCQNTGGGVHIAFG
QGTKLTVLG

SEQ ID No.: 130- VH DLX2475
EVQLVESGGGLVQPGGSLRLSCTASGFSLSSYAMAWVRQAPGKGLEWVGI
IYDSASTYYASWAKGRFTISRDTSKNTVYLQMNSLRAEDTAVYYCARERA
IFSGDFKLWGQGTLVTVSS

SEQ ID No.: 131- VL DLX2476
EIVMTQSPSTLSASVGDRVIITCQASQSISSWLSWYQQKPGKAPKLLIYR
ASTLASGVPSRFSGSGSGAEFTLTISSLQPDDFATYYCQNTGGGVSIAFG
QGTKLTVLG

SEQ ID No.: 132- VH DLX2476
EVQLVESGGGLVQPGGSLRLSCTASGFSLSSAAMAWVRQAPGKGLEWVGI
IYDSASTYYASWAKGRFTISRDTSKNTVYLQMNSLRAEDTAVYYCARERD
IFSGDFVGWGQGTLVTVSS

SEQ ID No.: 133- VL DLX2480
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGINIAFG
QGTKLTVLG

SEQ ID No.: 134- VH DLX2480
EVQLVESGGGLVQPGGSLRLSCTASGFSLSDAAMAWVRQAPGKGLEWVGI
IYDSASTYYASWAKGRFTISRDTSKNTVYLQMNSLRAEDTAVYYCARERQ
IFSGDFVLWGQGTLVTVSS

SEQ ID No.: 135- VL DLX2543
EIVMTQSPSTLSASVGDRVTITCQASQSISSWLSWYQQKPGKAPKLLIYK
ASTLASGVPSRFSGSGSGTEFTLTISSLQPDDFATYYCQNAGGGVSIAFG
QGTKLTVLG

SEQ ID No.: 136- VL DLX2529
EIVMTQSPSTLSASVGDRVIITCRASQSIGNWLSWYQQKPGKAPKLLIYR
ASNLASGVPSRFSGSGSGAEFTLTISSLQPEDFATYYCQNTGGGINIAFG
QGTKLTVLG

SEQ ID No.: 137- VL DLX2547
ADIVMTQSPSTLSASVGDRVTITCQASQSISSYLSWYQQKPGKAPKLLIY
RASTLASGVPSRFSGSGSGAEFTLTISSLQPDDFATYYCQNTGGGINIAF
GQGTKLEIKR

SEQ ID No.: 138- VH DLX2547
EVQLVESGGGLVQPGGSLRLSCTASGFSLSSAAMAWVRQAPGKGLEWVGI
IYDSASTYYASWAKGRFTISRDTSKNTVYLQMNSLRAEDTAVYYCARERA
IFSGDFVLWGQGTLVTVSS

SEQ ID No.: 139- VL DLX2528
EIVMTQSPSTLSASVGDRVTITCQASQSIGNWLAWYQQKPGKAPKLLIYQ
ASNLASGVPSRFSGSGSGTDFTLTISSLQPDDFATYYCQNAGGATTIAFG
QGTKLTVLG

SEQ ID No.: 140- VH DLX2528
EVQLVESGGGLVQPGGSLRLSCTASGFSLSSAAMAWVRQAPGKGLEWVGI
IYDSASTYYASWAKGRFTISRDTSKNTVYLQMNSLRAEDTAVYYCARERA
IFSGDFVLWGQGTLVTVSS

SEQ ID No.: 141- VL DLX2585
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLG

SEQ ID No.: 142- VH DLX2585
EVQLVESGGGLVQPGGSLRLSCTVSGFSLSSYAMSWVRQAPGKGLEWVGI
IYDSASTYYASWAKGRFTISKDTSKNTVYLQMNSLRAEDTAVYYCARERA
IFSGDFDYWGQGTLVTVSS

SEQ ID No.: 143- VL DLX2545
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLG

SEQ ID No.: 144- VH DLX2545
EVQLVESGGGLVQPGGSLRLSCTASGFSLSSAAMAWVRQAPGKGLEWIGI
IYDSASTYYASWAKGRFTISRDTSKNTLYLQMNSLRAEDTAVYFCARERN
IFSGDMVLWGQGTTVTVSS

SEQ ID No.: 145- VL DLX2531
EIVMTQSPSTLSASVGDRVIITCQASQSIDNWLSWYQQKPGKAPKLLIYR
ASTLASGVPSRFSGSGSGAEFTLTISSLQPDDFATYYCQNTGGGVSIAFG
QGTKLTVLG

SEQ ID No.: 146- VH DLX2531
EVQLVESGGGNVQPGGSLRLSCTASGFSLSNSAMAWVRQAPGKGLEWVGI
IYDSASTYYASWAKGRFTISRDNSKNTVYLQMNSLRAEDTATYYCARERA
IFSGDFALWGQGTLVTVSS

Sequence listing

SEQ ID No.: 147- VL DLX2586
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLG

SEQ ID No.: 148- VH DLX2586
EVQLVESGGGLVQPGGSLRLSCTVSGFSLSSYAMSWVRQAPGKGLEWIGI

IYDSASTYYASWAKGRFTISKDTSKNTVYLQMNSLRAEDTAVYFCARERQ

IFSGDMDGWGQGTLVTVSS

SEQ ID No.: 149- VL DLX2530
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLG

SEQ ID No.: 150- VH DLX2530
EVQLVESGGGNVQPGGSLRLSCTASGFSLSDAAMAWVRQAPGKGLEWVGI

IYDSASTFYASWAKGRFTISRDNSKNTLYLQMNSLRAEDTATYYCARERN

IFSGDMALWGQGTTVTVSS

SEQ ID No.: 151- VL DLX2548
EIVMTQSPSTLSASVGDRVIITCQASQSIDNWLSWYQQKPGKAPKLLIYR

ASTLASGVPSRFSGSGSGAEFTLTISSLQPDDFATYYCQNTGGGVSIAFG

QGTKLTVLG

SEQ ID No.: 152- VH DLX2548
EVQLVESGGGLVQPGGSLRLSCTVSGFSLSSYAMSWVRQAPGKGLEWIGI

IYDSASTYYASWAKGRFTISKDTSKNTLYLQMNSLRAEDTAVYFCARERQ

IFSGDMDGWGQGTTVTVSS

SEQ ID No.: 153- VL DLX2544
ADIVMTQSPSTLSASVGDRVTITCQASQSISSYLSWYQQKPGKAPKLLIY

KASTLASGVPSRFSGSGSGTDFTLTISSLQPEDFATYYCQNAGGGINIAF

GQGTKVEKR

SEQ ID No.: 154- DLX2544
ADIVMTQSPSTLSASVGDRVTITCQASQSISSYLSWYQQKPGKAPKLLIY

KASTLASGVPSRFSGSGSGTDFTLTISSLQPEDFATYYCQNAGGGINIAF

GQGTKVEIKRGGGGSGGGGSGGGGSGGGGSEVQLVESGGGLVQPGGSLRL

SCTASGFSLSSAAMAWVRQAPGKGLEWVGIIYDSASTYYASWAKGRFTIS

RDTSKNTVYLQMNSLRAEDTAVYYCARERAIFSGDFVLWGQGTLVTVSS

SEQ ID No.: 155- CDR-H1 of DLX2531
FSLSNSAMA

SEQ ID No.: 156- CDR-H2 of DLX2531
IIYDSASTYYASWAKG

SEQ ID No.: 157- CDR-H3 of DLX2531
ERAIFSGDFAL

SEQ ID No.: 158- CDR-L1 of DLX2531
QASQSIDNWLS

SEQ ID No.: 159- CDR-L2 of DLX2531
RASTLAS

SEQ ID No.: 160- CDR-L3 of DLX2531
QNTGGGVSIA

SEQ ID No.: 161- CDR-L1 of DLX2681
RASQSIGNWLS

SEQ ID No.: 162- CDR-L2 of DLX2681
RASNLAS

SEQ ID No.: 163- CDR-L3 of DLX2681
QNTGGGINIA

EXAMPLES

Example 1

Identification of rhIL-1 Beta Neutralizing scFv

Immunization of rabbits: Rabbits were immunized with recombinant human IL-1 beta protein (Peprotech, USA, cat. no. 200-01B), Lymph node and spleen cells were isolated after the final boost and the cells were cryopreserved.

Flow cytometry sorting of rabbit B cells and culturing: IL-1 beta-specific memory B cells were sorted as single cells into 96-well microplates using FACSAria III (BD Biosciences). Single B cell clones were cultured in the presence of feeder cells.

Screening of B cell clones: Cell culture supernatants were analyzed by ELISA for the presence of anti-IL-1 beta-specific IgGs. Briefly, rhIL-1 beta (Peprotech, cat. no. 200-01B) was coated at a concentration of 2 mcg/ml overnight at 4° C. on Maxisorp 96-well microplates in PBS. After blocking with 5% non-fat dry milk, cell culture supernatants were added. IL-1 beta-specific IgGs were detected by anti-rabbit IgG-HRP (Southern Biotech, cat. no. 4050-05). The ELISA was developed with BM Blue POD substrate (Roche Applied Science). B cell clones specific for rhIL-1 beta were further analyzed for their neutralization capacity in a human fibroblast assay.

Sequencing of IL-1 beta-neutralizing IgGs: all rabbit B cell clones producing neutralizing anti-IL-1 beta antibodies were subjected to mRNA isolation using the RNeasy Mini Kit (Qiagen Germany, cat. no. 74106). mRNA was used as template for reverse transcription according to the manufacture's protocol (OneStep RT-PCR kit, Qiagen Germany, cat. no. 21.0212). Subsequently, PCR reactions using oligonucleotides to specifically amplify rabbit IgG heavy and light chain encoding sequences were carried out (Biometra Thermocycler T3). Heavy and light chain PCR fragments were independently sequenced (ABI, Sanger 3730xl; Microsynth AG, Balgach, Switzerland), and obtained DNA sequences were translated into protein sequences using EMBOSS Transeq and aligned using CLUSTALW2.

Construction of anti-IL-1 beta scFv genes, and scFv protein expression: rabbit IgG CDR regions of the light and the heavy chains as defined above were identified and grafted into the human light and heavy chain acceptor frameworks comprising SEQ ID Nos.: 18-21 and 22-25, respectively. Bacterial expression vectors were generated encoding scFv proteins with the N-terminal variable light chain linked by the sequence SEQ ID No: 9 to the C-terminal variable heavy chain. ScFv proteins were expressed in *E. coli* BL21 (DE3); Novagen, USA, cat. no. 69450-3) as inclusion bodies, which were purified, solubilized and the proteins were refolded. The refolded scFvs were purified by standard size exclusion chromatography and monomeric peak fractions were collected. Purified scFvs were analyzed for IL-1 beta binding by ELISA. ScFv that were found to specifically bind rhIL-1 beta were tested for IL-1 beta neutralization in a human fibroblast assay. By this procedure, the scFv DLX2323 and other anti-IL-1 beta scFvs were identified as potent inhibitors of IL-1 beta.

Example 2

Recognition of Human IL-1 Beta

Firstly, the specific recognition of rhIL-1 beta by DLX2323 was confirmed by ELISA (FIG. 1). Briefly, rhIL-1 beta (Peprotech, cat. no. 200-01B) was coated at a concentration of 2 mcg/mil overnight at 4° C. on Maxisorp 96-well microplates in PBS. After blocking with 5% non-fat dry milk, increasing concentrations of scFvs (10 to 300 ng/ml) were added, and scFvs were detected by Protein L-HRP (Sigma-Aldrich, cat. no. P3226). The ELISA was developed with BM Blue POD substrate (Roche Applied Science). As a negative control, scFv of irrelevant specificity was used. This result shows that DLX2323 specifically binds to rhIL-1 beta.

To confirm that DLX2323 and the control scFv were recognized by Protein L-HRP and, thus, a lack of signal for rhIL-1 beta binding in the ELISA above was not due to a detection problem, another experiment was conducted. The scFvs were directly coated on the plate and detected by Protein L-HRP as described above. All scFvs were coated at a concentration of 2 mcg/ml in PBS. This ELISA experiment showed that DLX2323 and the control scFv are recognized by the detection agent Protein L-HRP.

Figure 2:
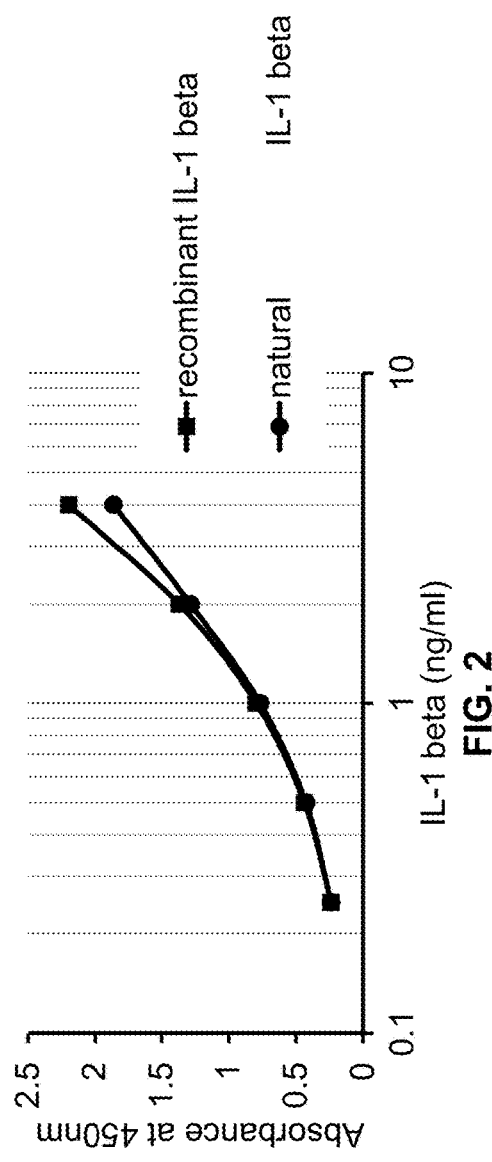
FIG. 2 is a graph depicting the results of DLX2323 binding to natural human IL-11 beta in comparison to binding to rhIL-1 beta. Natural human IL-1 beta was derived from supernatant of activated THP-1 cells.

In another ELISA (FIG. 2), the recognition of human natural IL-1 beta by DLX2323 was confirmed. As commonly known, expression of human proteins in cells other than human cells might cause changes, e.g., in post-translational modifications and/or conformation. This might lead to a differential recognition of recombinant and natural proteins by antibodies. Natural human IL-1 beta was secreted by THP-1 cells (DSMZ Germany, cat. no. ACC 16) after stimulation with 10 ng/ml of PMA (Sigma-Aldrich, cat. no. P1585), 1 mg/ml of LPS (Sigma-Aldrich, cat. no. L4391) and 2 mM of ATP (Sigma-Aldrich, cat. no. A6559-25UMO). Cell supernatants were harvested and secreted human natural IL-1 beta was quantified using the Human IL-1 beta/IL-1F2 ELISA DuoSet (R&D Systems, cat no. DY201). DLX2323 was coated on 96-well microplates (Maxisorp, Nunc) at a coating density of 5 mcg/ml in DPBS (pH 7.4). Human IL-1 beta either as recombinantly expressed version (Peprotech, cat, no. 200-01B) or as natively secreted version were applied at final concentrations ranging from 0.5 to 4 ng/ml. Bound IL-1 beta was detected by a biotinylated goat anti-hIL-1 beta antibody (R&D Systems, cat. no. DY201) and Streptavidin-HRP (BD Pharmingen, cat. no. 554060). The ELISA was developed using BM Blue POD substrate (Roche Applied Science). For quantification purposes the absorbance was measured at 450 nm using a VersaMax microplate reader (Molecular Devices, USA). The result (see FIG. 2) shows that both, recombinant and natural human IL-1 beta are recognized by DLX2323 at comparable levels.

Example 3

Neutralization of rhIL-1 Beta Biological Activity

Antibodies and scFvs were tested for their IL-1 beta neutralization capacity in a human dermal fibroblast assay (NHDF-Neo, cat. no. CC-2509, Lonza Walkersville USA). Activation of such fibroblasts with IL-1 beta leads to specific IL-6 release which is quantified by ELISA. Inhibition of IL-1 beta by specific antibodies decreases the amount of IL-6 released from such fibroblasts. The inhibitory potency of the anti-IL-1 beta antibody is quantified by measuring the half-maximal reduction ($IC_{50}$) of IL-1 beta-induced IL-6 release. Human dermal fibroblasts were seeded in 96-well microplates at 5,000 cells/well 16-20 hours prior to addition of IL-1 beta. The fibroblasts were cultured in fibroblast basal medium (FBM; Lonza, cat. no. CC-3131) with supplements (hFGF-B, Insulin, FBS, GA-1000) as described by the cell supplier (Lonza Walkersville USA: CLONETICS™ Dermal Fibroblast Cell Systems). FBM then was removed and cells were washed once with Dulbecco's Modified Eagle Medium (DMEM; Gibco, Life Technologies, cat. no. 11880) to remove growth factors. Cells were then incubated for 7 hours in DMEM media. Antibodies or scFvs and rhIL-1 beta were pre-incubated in DMEM for 1 hour at 37° C. The mixture was added, to the cells at a final concentration of 10 pg/ml of IL-1 beta. As negative control, 10 pg/ml of IL-1 beta was added to cells without any anti-IL-1 beta antibody. As positive control, a mouse monoclonal antibody against IL-1 beta was applied (R&D systems, USA, cat. no. MAB201). The cells were incubated with the IL-1 beta/anti-IL-1 beta antibody mixture for 18-24 hours, and cell culture supernatants were analyzed for IL-6 release using the Human IL-6 DuoSet ELISA Kit according to the manufacturer's instructions (R&D Systems, USA, cat. no. DY206). The $IC_{50}$ of DLX2323 was determined to be 3 pM±1.05 in eight independent assays.

Example 4

Figure 3A:
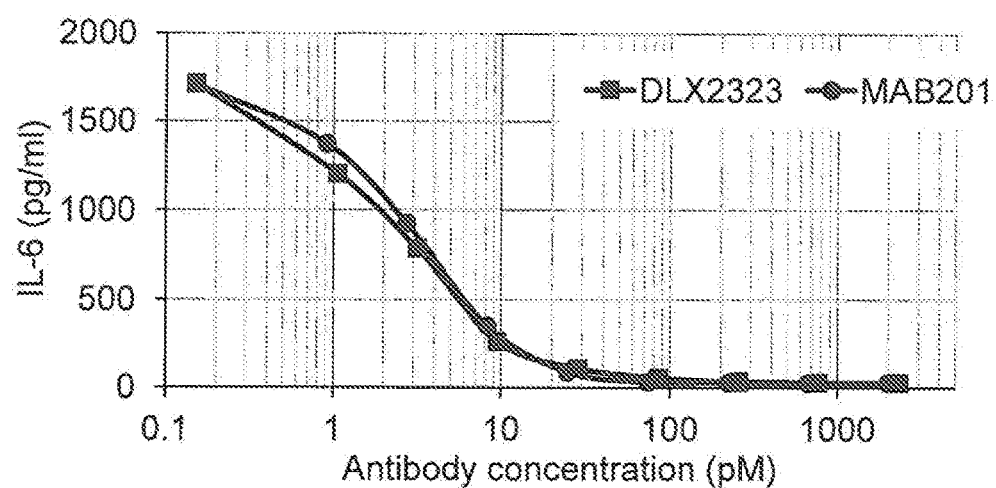
FIGS. 3A and 3B show comparisons of DLX2323 with several commercially available IL-1 beta inhibitors for neutralization of rhIL-1 beta in a human fibroblast assay from two independent experiments. Panel A shows the results for DLX2323 and MAB201, and Panel B summarizes data for DLX2323, rhIL-1 receptor antagonist (ra) and canakinumab (ILARIS®).
Figure 3B:
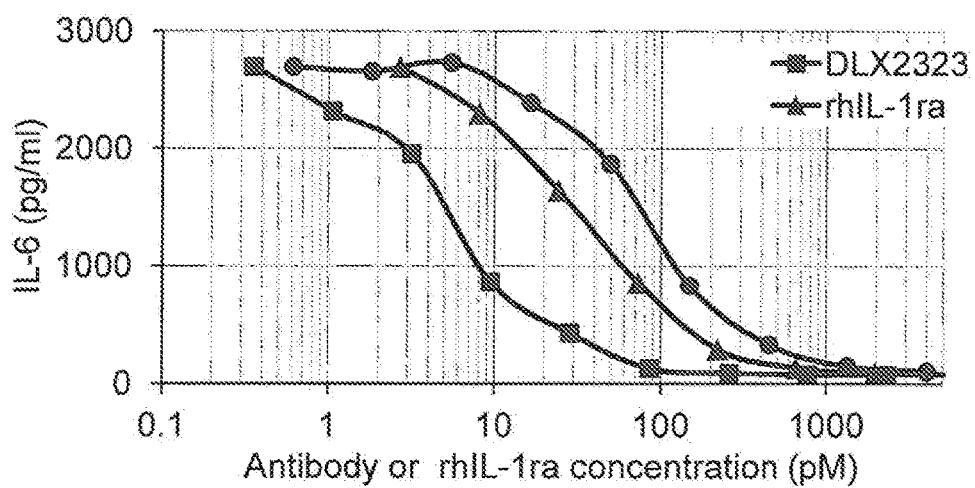

Comparison of Neutralization Potency with Commercially Available IL-1 Beta Inhibitors DLX2323 was identified as an IL-1 beta neutralizing scFv. The biological potency of DLX2323 and other inhibitors was assessed in the human dermal fibroblast assay as described in Example 3. Recombinant human IL-1 beta was pre-incubated with increasing concentrations of the scFv DLX2323, the anti-human IL-1 beta monoclonal IgG antibody MAB201, the IL-1 beta receptor antagonist (rhIL-1ra) (R&D systems, cat. no. 280-RA-010/CF) or the FDA approved, marketed canakinumab IgG (Novartis, ILARIS®) prior to addition to the wells. Two independent experiments were performed: FIG. 3, Panel A depicts the comparison of DLX2323 with MAB201, whereas FIG. 3, Panel B shows the comparison of DLX2323 with rhIL-1ra and canakinumab. The following $IC_{50}$ values were determined; MAB201: 2-3 pM; DLX2323: 2-4 pM; rhIL-1ra: 40 pM and Canakinumab: 90 pM. In conclusion, the monovalent monomeric scFv DLX2323 is almost as potent as the bivalent monoclonal mouse antibody MAB201. It shows distinctly higher potency in neutralizing human IL-1 beta than the marketed inhibitor Canakinumab and the rhIL-1ra. Furthermore, DLX2323 could fully block IL-1 beta-induced IL-6 release.

Example 5

Solubility

DLX2323 was stored in PBS buffer pH 7.2 (Phosphate Buffered Saline 1×, Gibco, LIFE TECHNOLOGIES™, cat. no. 20012). To determine its maximum solubility, DLX2323 was concentrated using Vivaspin 20 centrifuge concentrators (Sartorius Stedim Biotech, cat. no, VS2001) at room temperature. The concentration process was stopped at 71 mg/ml due to the high viscosity of the sample. The obtained DLX2323 protein solution was viscous, clear, and no precipitates were observed by visual inspection.

Example 6

Stability

Regarding the stability of scFvs, two different processes can be observed that contribute to their instability. Firstly, the scFv could be prone to dimerization, often followed by oligomerization and eventually aggregation. Secondly, scFv degradation, leading to smaller fragments, can occur over time. To judge whether DLX2323 is stable, HPLC (Dionex, Summit system) size exclusion chromatography (Tosoh, TSKgel G2000SWxl, cat. no. 08540) was deployed to determine the percentage of monomeric, non-degraded scFv protein at certain time points at different protein concentrations and temperatures (e.g., 4° C., RT and 37° C.). The percentage of monomer was measured at the starting point of the study (T0) and after one month for 1 mg/ml of DLX2323, and, in another experiment, after two weeks for a 50 mg/ml solution of DLX2323. The protein was formulated in PBS, pH 7.2. The results of the stability study are listed in tables 1 and 2.

TABLE 1

| | monomer content after 1 month | Observation |
|---|---|---|
| DLX2323, 1 mg/ml, T0 | 97% | |
| DLX2323, 1 mg/ml, stored at RT | 98% | |
| DLX2323, 1 mg/ml, stored at 37° C. | 93% | Very low levels of degradation |

TABLE 2

| | monomer content after 2 weeks | Observations |
|---|---|---|
| DLX2323, 50 mg/ml, T0 | 97% | |
| DLX2323, 50 mg/ml, stored at 4° C. | 78% | dimerization |
| DLX2323, 50 mg/ml, stored at RT | 76% | oligomerization |
| DLX2323, 50 mg/ml, stored at 37° C. | 43% | oligomerization |

DLX2323's thermal stability was assessed by differential scanning fluorimetry (DSF). For this measurement a real-time PCR device (Corbett, Rotor-Gene) heated DLX2323 in a temperature gradient from 30° C. to 95° C. (raising in 1° C. steps, waiting 5 seconds per step). The protein sample contained 0.5 mg/ml of DLX2323 and 20× SYPRO® Orange (Sigma-Aldrich, cat. no. 5692, 5000×) in PBS. As soon as the protein started melting, Sypro Orange turned fluorescent. This fluorescence was online measured (excitation wavelength of 470 nm; emission wavelength of 555 nm) during the gradient run. Using Rotor-Gene 6000 Series Software 1.7 the midpoint melting temperature (Tm) of DLX2323 was calculated to be 74° C.

Example 7

Cross-Reactivity

Cross-reactivity of DLX2323 to IL-1 beta homologs of other species than human beings was assessed in ELISA. Binding to the recombinantly expressed IL-1 beta proteins of the following species was investigated: cynomolgus (Sino Biological Inc., USA, cat. no. 90010-CNAE), rhesus macaque (R&D Systems, USA, cat. no. 1318-RL/CF), swine (Kingfisher Biotech, USA, cat. no, RP0297S-025), canine (Kingfisher Biotech, USA, cat. no. RP0085D-025), guinea pig (Kingfisher Biotech, cat. no. RP0343GP-025), rat (Peprotech, cat no. 400-01B) and mouse (BioLegend, cat. no. 575102). Binding of DLX2323 was compared to ELISA-positive control antibodies (R&D Systems, USA, goat anti-human IL-1 beta polyclonal IgG, cat. no. AB-201-NA; BioLegend, Inc., USA, biotin anti-mouse/rat IL-1 beta antibody, cat. no. 503505). Briefly, proteins were coated at a concentration of 2 mcg/ml over night at 4° C. on Maxisorp 96-well microplates in PBS. After blocking with 5% non-fat dry milk, increasing concentrations (0.1 mcg/ml, 0.3 mcg/ml and 1.0 mcg/ml) of DLX2323 were added to the wells. Successful coating of every protein was separately confirmed exploiting IL-1 beta-specific control antibodies. Whereas DLX2323 was detected by Protein L-HRP (Sigma-Aldrich, USA, cat. no. P3226), the control antibodies were detected by either Streptavidin-HRP (BD Pharmingen, USA, cat, no. 554060) or other eligible secondary antibodies labelled with HRP. The ELISA was developed with BM Blue POD substrate (Roche Applied Science) and the absorbance was measured at 450 nm. DLX2323 recognized four species orthologs of IL-1 beta, namely human, cynomolgus, rhesus macaque and rat IL-1 beta. No cross-reactivity could be observed for porcine, guinea pig, canine and mouse IL-1 beta.

Besides the cross-reactivity of DLX2323 to IL-1 beta homologs of other species than human beings, the recognition pattern of DLX2323 regarding various human IL-1 family members and other cytokines was measured: rhIL-1ra (R&D systems, USA, cat. no. 280-RA-010/CF), rhIL-1 alpha (PeproTech, cat. no. 200-01A), rhIL-18 (BioVision, cat. no. 4179-25), rhIL-33 (Peprotech, cat. no. 200-33), IL-36ra (R&D Systems, cat. no, 1275-IL/CF), rhTNF alpha (Peprotech, Hamburg, Germany cat. no. 300-01A) and rhIL-6 (Peprotech, cat. no. 200-06). In the applied ELISA assay the following antibodies served as positive controls: biotin anti-human IL-1ra (BioLegend, cat, no. 509501), biotin anti-human IL-1 alpha (BioLegend, cat. no. 515703), anti-human IL-18 polyclonal antibody (BioVision, cat. no. 5179-100), biotin anti-human IL-33 antibody (Peprotech, cat. no. 500-P261Bt), anti-human TNF alpha scFv DLX105 (Delenex propriety antibody described in WO 2006/131013 A), biotin anti-human IL-6 (R&D systems, DY206, cat. no. 840114), anti-human IL-36ra (R&D systems, cat. no. AF1275). The ELISA was carried out essentially as described above. No cross-reactivities of DLX2323 for any of these tested human IL-1 family members and cytokines could be detected.

Example 8

In vivo Efficacy

Figure 4:
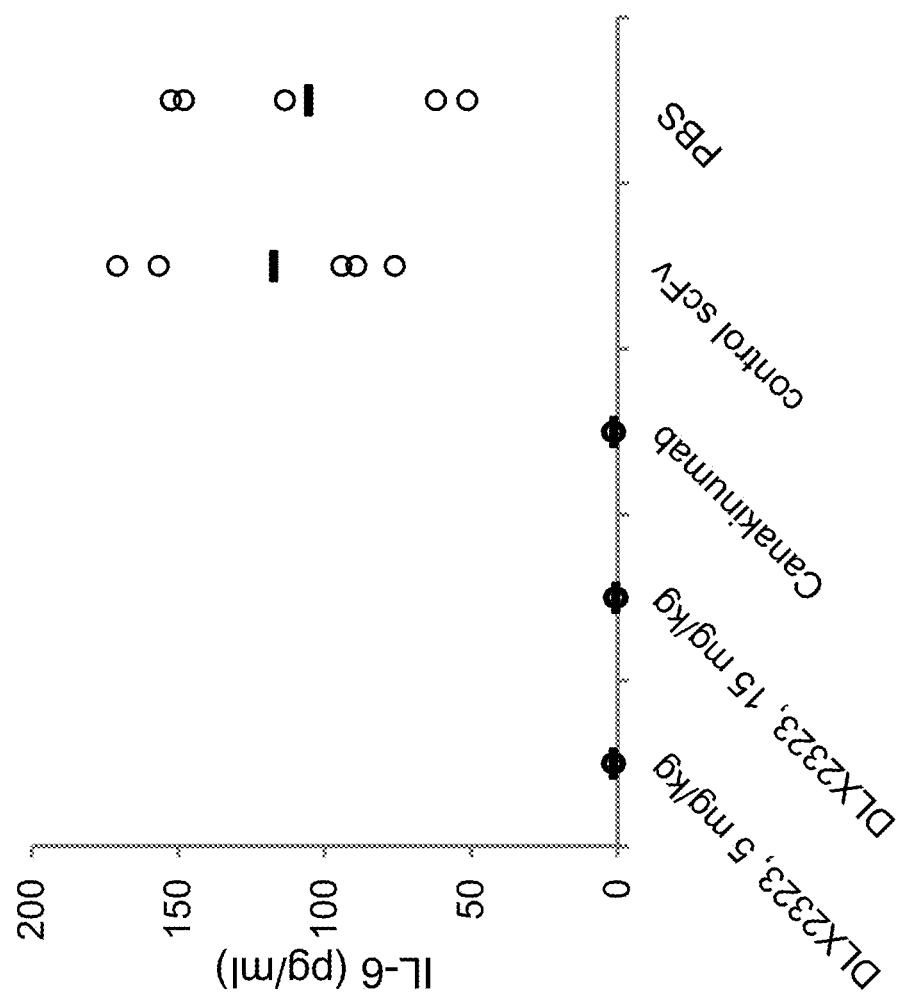
FIG. 4 shows the in vivo efficacy of DLX2323 in a human IL-1 beta-induced mouse inflammation model.

In this example, the in vivo inhibition of human IL-1 beta activity by DLX2323 is demonstrated. Human IL-1 beta can bind and activate the mouse IL-1 receptor thereby inducing an inflammatory response in the mouse in vivo. The inflammation leads to elevated levels of cytokines in the serum including mouse IL-6 (mIL-6). Recombinant human IL-1 beta (Peprotech, cat, no. 200-01B) was administered subcutaneously at a dose of 1.5 mcg/kg body weight to 8 weeks old male BALB/c mice (Charles River, Germany). After 2 hours mL-6 levels were significantly elevated in serum. To test the neutralization capacity of DLX2323 in vivo, it was intraperitoneally (i.p.) injected two hours prior to the IL-1 beta dosing. One group of mice was injected with a 5 mg/kg dose of DLX2323, the second group was injected with a 15 mg/kg dose of DLX2323. Negative control groups were treated with either PBS i.p. or scFvs of irrelevant specificity. A fifth group of mice was intravenously injected with 10 mg/kg of canakinumab (Novartis, ILARIS®) as a positive control. Two hours after the rhIL-1 beta application blood samples were taken and serum levels of mIL-6 were measured using the Mouse IL-6 DuoSet ELISA kit according to the manufacturer's instructions (R&D Systems, cat. no. DY406). For the groups of mice treated with DLX2323 and canakinumab only very low amounts of mIL-6 or even no mIL-6 could be detected (0.0-2 pg/ml of mIL-6; FIG. 4). Mice receiving PBS or control scFv showed significantly elevated IL-6 levels of 50 to 170 pg/ml. DLX2323 was very efficiently neutralizing human IL-1 beta in an in vivo setting, even at a 5 mg/kg dose.

Example 9

CDR Libraries

To better characterize the association of DLX2323 with human IL-1 beta, amino acid mutations were designed and site-specifically inserted into the CDR regions of DLX2323. CDR positions were chosen for mutagenesis based on their surface exposure, anticipated interaction with human IL-1 beta as deduced from homology models or sequence comparisons with antecedent rabbit IgGs. In the light chain, the motif DNW in CDR-L1 (SEQ ID No: 14), the amino acid residues R and T in CDR-L2 (SEQ ID No: 15), the threonine in CDR-43 as well as the motif GGVS were selected (SEQ ID No: 16) for the design of variants of DLX2323. In the heavy chain, the motif SA was chosen in CDR-H1 (SEQ ID No: 11), in the CDR-H2 the motif YD and the following tyrosine (SEQ ID No: 12). In CDR-H3, all positions were selected for substitution (SEQ ID No: 13) except for the N-terminal glutamic acid (E). All said positions are indicated with an X in SEQ ID Nos. 11-16, respectively. Site directed mutagenesis, sequencing of clones and library assembly were carried out by GeneArt (LIFE TECHNOLOGIES™, Regensburg, Germany).

The resulting scFv mutants are expressed in 96-well format in 1 ml cultures in *E. coli* BL21 (DE3) (Novagen, USA, cat. no. 69450-3). During expression in this system most of the scFv proteins form insoluble inclusion bodies within the cell but a considerable amount of protein can be retrieved from the soluble fractions after cell lyses, which was found to be sufficient for the analysis by the rhIL-1 beta ELISA (see example 2 for details). Cells were lysed in lysis buffer (1 mM EDTA, 0.1 mg/ml lysozyme, PBS pH 7.2) in a 96-well format by freezing and subsequent thawing. Derived crude extracts were cleared by centrifugation. Supernatants were added to wells of a microtiterplate coated with 50 ng/ml of rhIL-1 beta (Peprotech) per well. After washing, bound scFvs are detected by ProteinL-HRP and binding to rhIL-1 beta quantified by BM Blue POD Substrate (Roche Applied Science).

Table 3 lists single-site mutations that clearly permit binding of rhIL-1 beta as defined by an ELISA signal at least 2-fold over the negative control, but not smaller than 0.1 optical units.

TABLE 3

| Residue position | amino acid substitutions |
| --- | --- |
| CDR-L1_D32 | A, C, E, F, G, H, I, K, L, M, N, P, Q, R, S, T, V, W, Y |
| CDR-L1_N33 | A, C, D, E, F, G, H, I, K, L, M, P, Q, S, T, V, W, Y |
| CDR-L1_W40 | E, F, G, M, N, Q, S, Y |
| CDR-L2_R58 | A, C, D, E, F, G, H, I, K, L, M, N, P, Q, S, T, W, Y |
| CDR-L2_T69 | A, C, D, E, F, G, H, I, K, L, M, N, P, Q, R, S, V, W, Y |
| CDR-L3_T109 | A, C, I, N, S, V |
| CDR-L3_G111 | A, P, S |
| CDR-L3_G112 | A, C, D, E, F, H, I, K, L, M, N, P, Q, R, S, T, V, W, Y |
| CDR-L3_V135 | A, C, D, E, F, G, H, I, K, L, M, N, P, Q, R, S, T, W, Y |
| CDR-L3_S136 | A, C, D, E, F, G, H, I, L, M, N, P, Q, R, T, V, W, Y |
| CDR-H1_S33 | A, C, D, E, F, G, H, I, K, L, M, N, P, Q, R, T, V, W, Y |
| CDR-H1_A39 | C, D, E, F, G, H, I, K, L, M, N, Q, R, S, T, V, W, Y |
| CDR-H2_Y59 | A, C, G, M |
| CDR-H2_D60 | N, P |
| CDR-H2_Y69 | A, D, E, G, F, H, I, K, L, M, N, P, S, T, W |
| CDR-H3_R110 | A, C, D, E, F, G, H, I, K, L, M, N, Q, S, T, V, W, Y |
| CDR-H3_A111 | C, D, F, G, H, I, K, M, N, P, Q, R, S, T, V, W, Y |
| CDR-H3_I112 | A, C, F, H, L, M, N, Q, S, T, V, Y |
| CDR-H3_F113 | I |
| CDR-H3_S114 | A, C, E, G, T, V |
| CDR-H3_G115 | A, M, N, |
| CDR-H3_D135 | A, E, H, N, S, T |
| CDR-H3_F136 | A, C, G, H, I, L, M, N, Q, S, T, V, W, Y |
| CDR-H3_V137 | A, C, D, E, F, G, H, I, K, L, M, N, P, Q, R, S, T, W, Y |
| CDR-H3_L138 | A, C, D, E, F, G, H, I, K, M, N, P, Q, R, S, T, V, W, Y |

These binding data have predictive value also concerning the neutralization of rhIL-t beta biological function as verified by the expression of five exemplary single-site mutants in large scale format, purified to homogeneity, and subjected to cell-based analysis alongside with likewise purified DLX2323 protein.

DLX2323_CDR-H1_A39N (SEQ ID No. 45 with X=N), DLX2323_CDR-H3_A111N (SEQ ID No.: 50 with X=N), DLX2323_CDR-H3_F136N (SEQ ID No. 56 with X=N), DLX2323_CDR-H3_V137D (SEQ ID No.: 57 with X=D), and DLX2323_CDR-H3_L38D (SEQ ID No.: 58 with X=D) and the corresponding parental scFv, DLX2323, were expressed in *E. coli* BL21(DE3) (Novagen) cells at a 2 liter scale. Following cell lysis by sonication, inclusion bodies were enriched by centrifugation, washed, protein solubilized in guanidine buffer (6 M guanidine/HCl, 100 mM Tris, 1 mM EDTA, pH 8.5), refolded in urea buffer (4 M urea, 50 mM glycine, 2 mM cystine, 2 mM cysteine, pH10), concentrated in 50 mM glycine, 50 mM NaCl, pH10, and purified to homogeneity by size exclusion chromatography. Monomeric peak fractions of this procedure were concentrated to a final protein content of approximately 0.5-5 mg/ml, passed over a sterile filter unit, and as such subjected to cell-based analyses as described in Example 3. Table 4 shows the neutralization potency $IC_{50}$ of each of the mutants as determined in two independent runs.

TABLE 4

| Clone ID | $IC_{50}$ |
| --- | --- |
| DLX2323 | 2-4 pM |
| DLX2323_CDR-H1_A39N | 10 pM |
| DLX2323_CDR-H3_A111N | 2-4 pM |
| DLX2323_CDR-H3_F136N | 2-4 pM |
| DLX2323_CDR-H3_V137D | 5 pM |
| DLX2323_CDR-H3_L138D | 10 pM |

In overall good agreement with the preceding ELISA results, an $IC_{50}$ value in the low pM range was observed for all five single-site mutants selected. Each member of the selected mutant subset had a neutralizing capacity towards rhIL-1 beta comparable to that of the parental scFv DLX2323. Accordingly, the binding of DLX2323 and its variants to rhIL-1 beta shows that a significant degree of sequence variability is allowed while concomitantly preserving key functional features.

Example 10

Generation of Combinatorial Variants

Based on the above, combinatorial mutants of DLX2323 were designed combining 3 to 9 of the previously investigated CDR singles-site changes. Individual residue changes were selected on basis of; (i) strong ELISA binding results comparable to or better than that of the parent antibody DLX2323; (ii) combinations of far-spread single site changes that would simultaneously affect multiple CDR regions, alone; and (iii) a cumulative modulation of CDR-H3, alone. The designed mutants were expressed in large scale format and purified as described above for the single mutants, before the neutralization capacity was assessed in the human fibroblast assay of Example 3. Individual amino acid changes per sequence and $IC_{50}$ data of corresponding scFv proteins are detailed in Table No.: 5. All these isolated scFv proteins had neutralizing activity towards rhIL1-beta in vitro. The five best candidates displayed $IC_{50}$ values in the low picomolar range, and are thus highly comparable to the parental scFv DLX2323.

TABLE 5

| scFv | Amino acid changes (AHo annotation) | IC50 |
| --- | --- | --- |
| DLX2464 | VL: parental<br>VH: A111Q, F136M, V137A, L138G | 4 pM |
| DLX2465 | VL: parental<br>VH: A111N, F136M, V137D | 4 pM |
| DLX2466 | VL: D32G, N33K, W40Y, T109A<br>VH: A39D, A111N, F136M, V137A, L138G | 300 pM |
| DLX2467 | VL: D32H, T69N, V135S<br>VH: S33R, A111M | 25 pM |
| DLX2468 | VL: D32G, W40Y, T109A, V135T<br>VH: A39S, A111N, F136M | 15 pM |
| DLX2475 | VL: N33K, R58Q, S136H<br>VH: A39Y, V137K | 200 pM |
| DLX2476 | VL: D32S, N33S<br>VH: A111D, L138G | 100 pM |
| DLX2480 | VL: V135I, S136N<br>VH: S33D, A111Q | 5 pM |

Variants carrying more than 6 amino acid substitutions in the CDR and flanking framework regions of the variable light and/or the variable heavy chain were designed. In total, combinatorial candidates (four VL and six VH mutant sequences) were generated, expressed, and functionally analysed for rhIL1-beta binding (ELISA) and neutralization (human fibroblast assay) in vitro as described in Example 3. Table 6 summarizes the respective point mutations as well as the neutralization potency as measured in two independent experiments of each clone.

TABLE 6

| ScFv | Amino acid changes (AHo annotation) | IC50 |
| --- | --- | --- |
| DLX2543 | VL: I20T, D32S, N33S, R58K, A87T, T109A<br>VH: parental | 3-4 pM |
| DLX2529 | VL: Q24R, D32G, T69N, D99E, V135I, S136N<br>VH: parental | 1-2 pM |
| DLX2547 | VL: E1D, I20T, D32S, N33S, W40Y, V135I, S136N, T146E, V147I, L148K, G149R<br>VH: parental | 30 pM |
| DLX2528 | VL: I20T, D32G, S42A, R58Q, T69N, A87T, E88D, T109A, G112A, V135T, S136T<br>VH: parental | 8 pM |
| DLX2585 | VL: parental<br>VH: A25V, A39Y, A42S, R82K, V137D, L138Y | 1-2 pM |
| DLX2545 | VL: parental<br>VH: V55I, V89L, Y105F, A111N, F136M, L144T | 7 pM |
| DLX2531 | VL: parental<br>VH: L12N, S33N, A39S, T84N, V103T, V137A | 0.6-1 pM |
| DLX2586 | VL: parental<br>VH: A25V, A39Y, A42S, V55I, R82K, Y105F, A111Q, F136M, V137D, L138G | 2 pM |
| DLX2530 | VL: parental<br>VH: L12N, S33D, Y69F, T84N, V89L, V103T, A111N, F136M, V137A, L144T | 1-2 pM |
| DLX2548 | VL: parental<br>VH: A25V, A39Y, A42S, V55I, R82K, V89L, Y105F, A111Q, F136M, V137D, L138G, L144T | 1-2 pM |

All 10 scFv proteins were found to effectively neutralize rhIL1-beta in the human fibroblast assay in vitro with $IC_{50}$ values in the high femtomolar to low picomolar range. Clones DLX2531, DLX2548, DLX2585, DLX2530, DLX2529, and DLX2586 reproducibly yielded lower $IC_{50}$ values than the parental scFv DLX2323.

Finally, the above VL and VH sequences were chain shuffled. Binding to rhIL1-beta was confirmed for cleared lysates of *E. coli* BL21 origami cells transformed with 19 chain shuffled VL and VH mutants. Table 7 summarizes the substitutions.

TABLE 7

| ScFv | VL-VH fusion | Amino acid substitutions |
| --- | --- | --- |
| DLX2676 | DLX2528_2530 | VL: I20T, D32G, S42A, R58Q, T69N, A87T, E88D, T109A, G112A, V135T, S136T<br>VH: L12N, S33D, Y69F, T84N, V89L, V103T, A111N, F136M, V137A, L144T |
| DLX2677 | DLX2528_2531 | VL: I20T, D32G, S42A, R58Q, T69N, A87T, E88D, T109A, G112A, V135T, S136T<br>VH: L12N, S33N, A39S, T84N, V103T, V137A |
| DLX2678 | DLX2528_2548 | VL: I20T, D32G, S42A, R58Q, T69N, A87T, E88D, T109A, G112A, V135T, S136T<br>VH: A25V, A39Y, A42S, V55I, R82K, V89L, Y105F, A111Q, F136M, V137D, L138G, L144T |

TABLE 7-continued

| ScFv | VL-VH fusion | Amino acid substitutions |
|---|---|---|
| DLX2679 | DLX2528_2585 | VL: I20T, D32G, S42A, R58Q, T69N, A87T, E88D, T109A, G112A, V135T, S136T<br>VH: A25V, A39Y, A42S, R82K, V137D, L138Y |
| DLX2680 | DLX2529_2530 | VL: Q24R, D32G, T69N, D99E, V135I, S136N<br>VH: L12N, S33D, Y69F, T84N, V89L, V103T, A111N, F136M, V137A, L144T |
| DLX2681 | DLX2529_2531 | VL: Q24R, D32G, T69N, D99E, V135I, S136N<br>VH: L12N, S33N, A39S, T84N, V103T, V137A |
| DLX2682 | DLX2529_2548 | VL: Q24R, D32G, T69N, D99E, V135I, S136N<br>VH: A25V, A39Y, A42S, V55I, R82K, V89L, Y105F, A111Q, F136M, V137D, L138G, L144T |
| DLX2683 | DLX2529_2585 | VL: Q24R, D32G, T69N, D99E, V135I, S136N<br>VH: A25V, A39Y, A42S, R82K, V137D, L138Y |
| DLX2684 | DLX2543_2530 | VL: I20T, D32S, N33S, R58K, A87T, T109A<br>VH: L12N, S33D, Y69F, T84N, V89L, V103T, A111N, F136M, V137A, L144T |
| DLX2685 | DLX2543_2531 | VL: I20T, D32S, N33S, R58K, A87T, T109A<br>VH: L12N, S33N, A39S, T84N, V103T, V137A |
| DLX2686 | DLX2543_2548 | VL: I20T, D32S, N33S, R58K, A87T, T109A<br>VH: A25V, A39Y, A42S, V55I, R82K, V89L, Y105F, A111Q, F136M, V137D, L138G, L144T |
| DLX2687 | DLX2543_2585 | VL: I20T, D32S, N33S, R58K, A87T, T109A<br>VH: A25V, A39Y, A42S, R82K, V137D, L138Y |
| DLX2689 | DLX2544_2531 | VL: BID, I20T, D32S, N33S, W40Y, R58K, A87T, E88D, D99E, T109A, V135I, S136N, L145V, T146E, V147I, L148K, G149R<br>VH: L12N, S33N, A39S, T84N, V103T, V137A |
| DLX2690 | DLX2544_2548 | VL: E1D, I20T, D32S, N33S, W40Y, R58K, A87T, E88D, D99E, T109A, V135I, S136N, L145V, T146E, V147I, L148K, G149R<br>VH: A25V, A39Y, A42S, V55I, R82K, V89L, Y105F, A111Q, F136M, V137D, L138G, L144T |
| DLX2691 | DLX2544_2585 | VL: E1D, I20T, D32S, N33S, W40Y, R58K, A87T, E88D, D99E, T109A, V135I, S136N, L145V, T146E, V147I, L148K, G149R<br>VH: A25V, A39Y, A42S, R82K, V137D, L138Y |
| DLX2692 | DLX2547_2530 | VL: E1D, I20T, D32S, N33S, W40Y, V135I, S136N, T146E, V147I, L148K, G149R<br>VH: L12N, S33D, Y69F, T84N, V89L, V103T, A111N, F136M, V137A, L144T |
| DLX2693 | DLX2547_2531 | VL: E1D, I20T, D32S, N33S, W40Y, V135I, S136N, T146E, V147I, L148K, G149R<br>VH: L12N, S33N, A39S, T84N, V103T, V137A |
| DLX2694 | DLX2547_2548 | VL: E1D, I20T, D32S, N33S, W40Y, V135I, S136N, T146E, V147I, L148K, G149R<br>VH: A25V, A39Y, A42S, V55I, R82K, V89L, Y105F, A111Q, F136M, V137D, L138G, L144T |
| DLX2695 | DLX2547_2585 | VL: E1D, I20T, D32S, N33S, W40Y, V135I, S136N, T146E, V147I, L148K, G149R<br>VH: A25V, A39Y, A42S, R82K, V137D, L138Y |

Binding was considered specific if an ELISA signal of ≥0.1 optical units was obtained which was at least 2-fold higher than the negative control. Results are shown in FIG. 6. For example, DLX2690 and DLX2691 slightly passed the cut-off filter, but are tested positive. The remaining collective VL and VH chain-shuffled mutants bind rhIL1-beta with absolute ELISA signals comparable to or even higher than DLX2323.

The $IC_{50}$ values of DLX2681 and DLX2693 were determined in the human fibroblast assay as described above. DLX2681 was found to neutralize rhIL1-beta with an $IC_{50}$ value of 0.6 pM and the $IC_{50}$ value of DLX2693 was determined to be 12.5 pM.

While there are shown and described presently preferred embodiments of the invention, it is to be understood that the invention is not limited thereto but may be otherwise variously embodied and practiced within the scope of the following claims. Since numerous modifications and alternative embodiments of the present invention will be readily apparent to those skilled in the art, this description is to be construed as illustrative only and is for the purpose of teaching those skilled in the art the best mode for carrying out the present invention. Accordingly, all suitable modifications and equivalents may be considered to fall within the scope of the following claims.

What is claimed:

1. A method for inhibiting IL-1 beta in a subject in need thereof, comprising administering a therapeutically effective amount of an antibody or a fragment thereof against IL-1 beta comprising:
   a. the variable heavy chain (VH) CDR sequences CDR-H1, CDR-H2, and CDR-H3 as set forth in: SEQ ID Nos.: 1, 2 and 3, respectively, and
   b. the variable light chain (VL) CDR sequences CDR-L1, CDR-L2, and CDR-L3 as set forth in: SEQ ID Nos.: 4, 5, and 6, respectively.

2. The method of claim 1, wherein the antibody or fragment thereof has a potency (IC50) with regard to inhibiting the biological effect of human IL-1 beta of lower than 50 pM as determined by inhibiting IL-1 beta stimulated release of IL-6 from human fibroblasts.

3. The method of claim 2, wherein said $IC_{50}$ is lower than about 30 pM.

4. The method of claim 2, wherein said $IC_{50}$ is lower than about 1 pM.

5. The method of claim 1, wherein the antibody or fragment thereof is a Fab, a Fab', a scFv, a Fv fragment, a nanobody, a VHH or a minimal recognition unit.

6. The method of claim 1, wherein the antibody or fragment thereof is a full-length immunoglobulin or a bivalent antibody fragment.

7. The method of claim 1, wherein the antibody or fragment thereof comprises the light chain variable framework region FR-L1 of SEQ ID No. 18, the light chain variable framework region FR-L2 of SEQ ID No.: 19, the light chain variable framework region FR-L3 of SEQ ID No.: 20 and/or the light chain variable framework region FR-L4 of SEQ ID No.: 21.

8. The method of claim 1, wherein the antibody or fragment thereof comprises the heavy chain variable framework region FR-H1 of SEQ ID Nos.: 22; the heavy chain variable framework region FR-H2 of SEQ ID Nos.: 23; the heavy chain variable framework region FR-H3 of SEQ ID Nos.: 24; and/or the heavy chain variable framework region FR-H4 of SEQ ID Nos.: 25.

9. The method of claim 1, wherein the antibody or fragment thereof comprises:
   a. a VH sequence of SEQ ID No.: 7; and
   b. a VL sequence of SEQ ID No.: 8.

10. The method of claim 1, wherein the antibody or fragment thereof has the sequence of SEQ ID No.: 10.

11. The method of claim 1, wherein the antibody or fragment thereof is humanized.

12. The method of claim 1, wherein the antibody or fragment thereof is cross-reactive with cynomolgus IL-1 beta, rhesus monkey IL-1 beta and/or rat IL-1 beta.

13. The method of claim 1, wherein the antibody or fragment thereof is modified to extend the half-life residence time in vivo in serum.

14. The method of claim 1, wherein the subject has proliferative diabetic retinopathy, gouty arthritis, Schnitzler syndrome, systemic juvenile idiopathic arthritis, rheumatoid arthritis, acute gouty arthritis, chronic gouty arthritis, urticaria, vasculitis, type 1 diabetes, type 2 diabetes, ankylosing spondylitis, recurrent multifocal osteomyelitis, relapsing polychondritis, cyropyrin-associated periodic syndrome (CAPS), Behçet's disease, familial mediterranean fever, chronic obstructive pulmonary disease, polymyalgia rheumatic, NALP3-mutations, pyoderma gangrenosum, chronic idiopathic urticarial, osteoarthritis, wet age-related macular degeneration, dry eye syndrome, pustular psoriasis, synovitis-acne-pustulosis-hyperostosis-osteitis syndrome, macrophage activation syndrome, periodic fever adenitis pharyngitis aphthous ulcer syndrome, adult-onset Still's disease, mevalonate kinase deficiency, atherosclerosis, TNF-receptor associated periodic syndrome (TRAPS), acne vulgaris and/or acne inversa.

15. The method of claim 1, wherein the subject is a human being.

16. The method of claim 1, wherein the antibody or fragment thereof is provided in a pharmaceutical composition.

17. The method of claim 1, wherein said antibody or fragment thereof is administered parenterally; orally; rectally; urogenitally; topically; intravitreally; intravenously; intraocularly; oticly; intranasally; by inhalation; dermally; sublingually; or buccally.

18. The method of claim 1, wherein said antibody or fragment thereof is provided with at least one further therapeutically effective compound.

19. The method of claim 18, wherein said compound is administered simultaneously or sequentially with said antibody or fragment thereof.

20. A method for inhibiting IL-1 beta in a subject in need thereof, comprising administering a therapeutically effective amount of a binding member against IL-1 beta comprising:
   a. the variable heavy chain (VH) CDR sequences CDR-H1, CDR-H2, and CDR-H3 as set forth in SEQ ID Nos.: 1, 2 and 3, respectively; and
   b. the variable light chain (VL) CDR sequences CDR-L1, CDR-L2, and CDR-L3 as set forth in SEQ ID Nos.: 4, 5, and 6, respectively.

21. The method of claim 20, wherein the binding member is monovalent or multivalent.

22. The method of claim 21, wherein the binding member is monovalent and is a Fab, a Fab', a scFv, or a Fv fragment.

23. The method of claim 21, wherein the binding member is multivalent and multispecific.

24. The method of claim 21, wherein the binding member is multivalent and is a full-length immunoglobulin, a diabody, or a bis-scFv.

* * * * *

UNITED STATES PATENT AND TRADEMARK OFFICE
CERTIFICATE OF CORRECTION

PATENT NO. : 10,077,302 B2
APPLICATION NO. : 15/202982
DATED : September 18, 2018
INVENTOR(S) : Grabulovski et al.

It is certified that error appears in the above-identified patent and that said Letters Patent is hereby corrected as shown below:

On the Title Page

Item (30) Foreign Application Priority Data: Please correct "12007503" to read -- 12007503.1 --

Column 2, Item (56) References Cited, FOREIGN PATENT DOCUMENTS, Line 11:
Please correct "WO 2009156725" to read -- WO 2009155725 --

Column 2, Item (56) References Cited, FOREIGN PATENT DOCUMENTS, Line 12:
Please correct "WO 2009156726" to read -- WO 2009155726 --

Page 2, Column 1, Item (56) References Cited, OTHER PUBLICATIONS, Line 4, Rudikoff et al. cite:
Please correct "*Aced.*" to read -- *Acad.* --

Page 2, Column 1, Item (56) References Cited, OTHER PUBLICATIONS, Line 9, Alten, R., et al. cite: Please correct "Arthrins" to read -- Arthritis --

Page 2, Column 1, Item (56) References Cited, OTHER PUBLICATIONS, Line 22, Owyang, A. M., et al. cite: Please correct "Modsi" to read -- Model --

Page 2, Column 1, Item (56) References Cited, OTHER PUBLICATIONS, Line 43, Gundluru, M. K., et al. cite: Please correct "pladlenolide" to read -- pladienolide --

Page 2, Column 1, Item (56) References Cited, OTHER PUBLICATIONS, Line 48, Paterson, I., et al. cite: Please correct "459-1473" to read -- 459-473 --

Page 2, Column 2, Item (56) References Cited, OTHER PUBLICATIONS, Line 7, Cheng, Y., et al. cite: Please correct "1975, pp. 3009-3108" to read -- 1973, pp. 3099-3108 --

Page 2, Column 2, Item (56) References Cited, OTHER PUBLICATIONS, Line 12, Zhen, J., et al. cite: Please correct "radiollgands" to read -- radioligands --

Signed and Sealed this
Twelfth Day of February, 2019

Andrei Iancu
*Director of the United States Patent and Trademark Office*

CERTIFICATE OF CORRECTION (continued)
U.S. Pat. No. 10,077,302 B2

Page 2, Column 2, Item (56) References Cited, OTHER PUBLICATIONS, Line 16, Dinarello, C. A. cite: Please correct "disease" to read -- diseases --

Page 2, Column 2, Item (56) References Cited, OTHER PUBLICATIONS, Line 24, Honegger, A., et al. cite: Please correct "immunoglobulln variable domains: An automatic modelling and analysis too" to read -- immunoglobulin variable domains: An automatic modelling and analysis tool --

Page 2, Column 2, Item (56) References Cited, OTHER PUBLICATIONS, Line 27, Needleman, S. B., et al. cite: Please correct "applicabie" to read -- applicable --

Page 2, Column 2, Item (56) References Cited, OTHER PUBLICATIONS, Line 33, Borras, L., et al. cite: Please correct "9054-906" to read -- 9054-9066 --

Page 2, Column 2, Item (56) References Cited, OTHER PUBLICATIONS, Line 40, Hou, J., et al. cite: Please correct "to loal" to read -- topical --

Page 2, Column 2, Item (56) References Cited, OTHER PUBLICATIONS, Line 49, Luanay, D., et al. cite: Please correct "Cytokinas" to read -- Cytokines --

Page 2, Column 2, Item (56) References Cited, OTHER PUBLICATIONS, Line 54, Vanderschueren, S., et al. cite: Please correct "413-8" to read -- 413-6 --

In the Specification

Column 1, Lines 8-9: Please correct "benefit t of" to read -- benefit of --

Column 3, Line 62: Please correct "IL-11" to read -- IL-1 --

Column 4, Line 1: Please correct "Panel A" to read -- FIG. 3A --

Column 4, Line 2: Please correct "Panel B" to read -- FIG. 3B --

Column 4, Line 36: Please correct "(Fe region)" to read -- (Fc region) --

Column 4, Line 46: Please correct "nanobodles" to read -- nanobodies --

Column 5, Line 65: Please correct "(150)" to read -- (I50) --

Column 7, Line 25: Please correct "NEEDILEMAN" to read -- NEEDLEMAN --

Column 9, Line 30: Please correct "CDR-112" to read -- CDR-H2 --

Column 12, Line 29: Please correct "more 0.5 preferably" to read -- more preferably --

Column 14, Line 42: Please correct "(Vii)" to read -- (vii) --

CERTIFICATE OF CORRECTION (continued)
U.S. Pat. No. 10,077,302 B2

Column 14, Line 45: Please correct "(Viii)" to read -- (viii) --

Column 16, Line 16: Please correct "VI" to read -- VH --

Column 16, Line 23: Please correct "VI" to read -- VH --

Column 16, Line 50: Please correct "VI" to read -- VH --

Column 20, Line 56: Please correct "C6000.03" to read -- C6000-03 --

Column 27, Line 15: Please correct "IYDSASTYYASWAKGRFTISRDTSKNTVYLQIVfN" to read -- IYDSASTYYASWAKGRFTISRDTSKNTVYLQMN --

Column 47, Line 42: Please correct "GQGTKVEKR" to read -- GQGTKVEIKR --

Column 48, Line 48: Please correct "21.0212" to read -- 210212 --

Column 50, Line 48: Please correct "FIG. 3, Panel A" to read -- FIG. 3A --

Column 50, Line 49: Please correct "FIG. 3, Panel B" to read -- FIG. 3B --

Column 51, Line 54: Please correct "5692" to read -- S5692 --

Column 53, Line 36: Please correct "CDR-43" to read -- CDR-L3 --

Column 56, Lines 3-4: Please correct "In total, combinatorial" to read -- In total, 10 combinatorial --